US012741079B2

(12) United States Patent
Hernandez

(10) Patent No.: US 12,741,079 B2
(45) Date of Patent: Sep. 22, 2026

(54) ORAL PHLEGM EXTRACTION SYSTEM AND METHOD OF USING SAME

(71) Applicant: PostOp Therapeutics LLC, Roswell, GA (US)

(72) Inventor: Jeffrey M. Hernandez, Roswell, GA (US)

(*) Notice: Subject to any disclaimer, the term of this patent is extended or adjusted under 35 U.S.C. 154(b) by 0 days.

(21) Appl. No.: 18/759,455

(22) Filed: Jun. 28, 2024

(65) Prior Publication Data

US 2026/0000823 A1 Jan. 1, 2026

(51) Int. Cl.

| | |
|---|---|
| ***A61M 1/00*** | (2006.01) |
| ***A61G 15/00*** | (2006.01) |
| ***A61G 15/12*** | (2006.01) |
| ***A61M 13/00*** | (2006.01) |

(52) U.S. Cl.

CPC ............ *A61M 1/87* (2021.05); *A61G 15/007* (2013.01); *A61G 15/125* (2013.01); *A61M 1/74* (2021.05); *A61M 1/77* (2021.05); *A61M 13/003* (2013.01); *A61M 2202/0466* (2013.01); *A61M 2210/0625* (2013.01)

(58) Field of Classification Search

CPC ........... A61M 1/87; A61M 1/74; A61M 1/77; A61M 13/003; A61M 2202/0466; A61M 2210/0625; A61G 15/007; A61G 15/125

See application file for complete search history.

(56) References Cited

U.S. PATENT DOCUMENTS

| | | | | |
|---|---|---|---|---|
| 3,731,675 A * | 5/1973 | Kelly | A61C 17/0211 | 601/164 |
| 5,104,315 A * | 4/1992 | McKinley | A61C 17/0211 | 433/80 |
| 5,509,801 A * | 4/1996 | Nicholson | A61C 19/06 | 601/165 |
| 9,907,633 B2 * | 3/2018 | Wolpo | A46B 15/0012 | |
| 11,191,624 B2 * | 12/2021 | Van Dijk | A46B 15/0051 | |
| 11,234,801 B2 * | 2/2022 | Hanuschik | A46B 11/00 | |
| 11,284,978 B2 * | 3/2022 | Bergheim | A61C 1/0007 | |
| 11,622,751 B2 * | 4/2023 | Fougere | A61C 17/0202 | 600/582 |
| 11,744,933 B2 * | 9/2023 | Altounian | A61M 1/77 | 604/30 |
| 2004/0107960 A1 * | 6/2004 | Wu | A61M 1/60 | 128/200.14 |

(Continued)

FOREIGN PATENT DOCUMENTS

| | | | |
|---|---|---|---|
| DE | 202011104169 U1 * | 12/2011 | A61C 19/063 |
| KR | 20180118323 A | 4/2017 | |

(Continued)

*Primary Examiner* — Tarla R Patel

(57) ABSTRACT

Described are oral phlegm extraction systems having a mouth insertion apparatus, a misting apparatus, and a suction apparatus. The mouth insertion apparatus includes a bite platform with at least one suction aperture positioned on a proximal end of the platform and directed toward an entrance to the patient's throat. A tongue positioner may also be included with at least one suction aperture positioned on a proximal end of the tongue positioner and directed toward an entrance to the patient's throat. The mouth insertion apparatus is also shaped to direct a flow of moist gas toward the entrance to the patient's throat.

15 Claims, 69 Drawing Sheets

(56) References Cited

U.S. PATENT DOCUMENTS

| | | | | |
|---|---|---|---|---|
| 2005/0037315 | A1* | 2/2005 | Inoue | A61C 17/0211 433/91 |
| 2006/0282010 | A1* | 12/2006 | Martin | A61B 5/415 600/560 |
| 2009/0123886 | A1* | 5/2009 | Vaska | A61F 5/566 433/91 |
| 2010/0288288 | A1* | 11/2010 | Hegde | A61F 5/566 128/848 |
| 2011/0220124 | A1* | 9/2011 | Vaska | A61M 16/0463 128/848 |
| 2012/0017917 | A1* | 1/2012 | Podmore | A61F 5/566 128/848 |
| 2017/0216085 | A1* | 8/2017 | Vaska | A61M 16/0495 |
| 2022/0061972 | A1 | 3/2022 | Javid | |
| 2022/0133452 | A1* | 5/2022 | Ko | A61C 17/0208 433/80 |

FOREIGN PATENT DOCUMENTS

| | | | | |
|---|---|---|---|---|
| KR | 101894231 B1 | 5/2017 | | |
| KR | 101995572 B1 | 12/2017 | | |
| KR | 102392722 B1 | 1/2020 | | |
| KR | 102371721 B1 | 11/2020 | | |
| KR | 102472793 B1 | 3/2021 | | |
| WO | WO-2006040018 A1 * | 4/2006 | | A61C 17/0211 |

* cited by examiner 10 126 124 120 182 139 122 132 130 134 184 180 137 136 124 128 186 138 135

FIG. 60

ORAL PHLEGM EXTRACTION SYSTEM AND METHOD OF USING SAME

FIELD OF THE INVENTION

To improve patient oral and oropharyngeal comfort post-surgical and non-surgical treatment (chemoradiation therapy) of head and neck malignancy. In addition, this device will provide post-surgical therapy for other surgical indications, including obstructive sleep apnea and chronic pharyngitis. For post operative therapy of cancer and non-cancer surgery, radiation and/or chemotherapy involving the head, nose, or throat.

BACKGROUND

As of 2023, an estimated 66,920 people will be diagnosed with head and neck cancer in the United States alone. (Worldwide, an estimated 562,328 people were diagnosed with head and neck cancer in 2020.) In addition, patients going through non-cancer treatment for palatine tonsillectomies (adult tonsil removal), obstructive sleep apnea (OSA) or chronic pharyngitis will benefit from this device too. These non-cancer operational treatments experience similar issues of severe sore throats and excessive phlegm. The estimates for these groups of patients are 297,000 and 30,000 respectively.

Patients in the midst of chemoradiation for head and neck cancer as well as post-operative surgical oncology patients experience severe sore throat combined with dysphagia, which results in an increase of mucus in the oral cavity and pharynx. Further, patients undergoing radiation experience desiccation of their mucus (xerostomia), making clearance more difficult. Radiation patients also typically develop a moderate to severe mucositis (inflammation of the mucus membrane lining), which further exacerbates dysphagia and mucus retention. Depending on the intensity of the treatment and patient factors, this typically lasts for 3 to 8 weeks. In addition, this underlying dysphagia increases patient's risk of aspiration, secondary to reduced function and retained mucus in the oral cavity and oropharynx. While a patient can provide oral hygiene during the day using a suction device or via expectoration, but this is extremely difficult during times the patient is trying to sleep. The need to suction excess mucus often will keep a patient awake throughout the night impacting their ability to have restful sleep. This ultimately negatively impacts their healing, well-being and ability to function throughout the day.

Apart from patients with head and neck cancer, patients who are post-surgical from surgery of the pharynx or oral cavity for obstructive sleep apnea (OSA) or chronic pharyngitis, experience much of the similar issues with dysphagia, excess mucus and impaired sleep as head and neck cancer patients; albeit on a more limited scale. In the United States, 297,000 palatine tonsillectomies are performed on adults each year (CDC, 2006) and about 30,000 other procedures for OSA. Surgical procedures for OSA include lingual tonsil ablation/resection, uvulopalatopharyngoplasty (UPPP) and other pharyngeal reduction procedures. The ability to ameliorate these devastating treatment related issues for both cancer patients and these other surgical patients is a major unmet need in our healthcare system. Patients recovering from head, nose or throat surgery, radiation and/or chemotherapy treatment generally experience excessive sore throat and phlegm for a period of 3 to 8 weeks. In addition, aspiration (aspirating . . . the action of drawing a breathe having the phlegm go into the lungs and choking) will require the patient to sit up vertically for this period of time. Excessive phlegm can be managed and expelled during the day, but this becomes an issue at night when the patient tries to sleep. The constant use of physical extraction requires the patient to be awake throughout the entire night. For the first 1 to 2 nights, the patient may have to physically extract the mucus/phlegm every minute. For the next 3 to 4 days, the physical extraction may take place every couple of minutes. This process may continue until the second or third week when the physical extraction takes place five to six times per hour. For the most part, the patients are awake, suffer from exhaustion, lack of hunger, and loss of weight from lack of sleep. The side effects from the underlying treatment may cause the patient to go back to the hospital and have a feeding tube inserted for proper nutrition, or worse.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The claim for this device/apparatus/solution is to minimize the need to physically exert effort in removing the excessive mucus from the oral cavity and oropharynx and provide a means for the patient to rest through the process. It will also provide a means to mist the mouth and throat (providing medication if necessary) to avoid dry mouth while suctioning both the mist and phlegm. The objective is to provide a way for the patient to sleep longer through the night, potentially avoid hemorrhage-related complications by humidifying the post-surgical site and provide a better quality of life.

Embodiments of an oral phlegm extraction system may include one or more of the following features: a mouth insertion apparatus having: a platform shaped to engage with a patient's teeth when worn and having at least one suction aperture positioned on a proximal end of the platform and directed toward an entrance to the patient's throat; a tongue positioner joined to the platform, where the tongue positioner may include: at least one suction aperture positioned on a proximal end of the tongue positioner and directed toward an entrance to the patient's throat; and a region shaped to direct a flow of moist gas toward the entrance to the patient's throat; a hollow interior region in open communication with the at least one platform suction aperture and the at least one tongue positioner suction aperture; a misting apparatus having a nozzle coupled to a distal end of the platform that is programmable to control at least one of frequency, duration, or content of a moist gas stream that is introduced into the patient's mouth and throat; where the nozzle is positioned so that the moist gas stream flows out of the nozzle and is directed toward the shaped region of the tongue positioner; and/or a suction apparatus having a vacuum pump coupled to the distal end of the platform and in open communication with the hollow interior region of the platform and tongue positioner to remove collected substances from the patient's mouth and throat. Other embodiments include corresponding computer systems, apparatus, and computer programs recorded on one or more computer storage devices, each configured to perform the actions of the methods.

Embodiments may include one or more of the following features: a plurality of nubs positioned on at least one of an upper surface or a lower surface of the platform; a plurality of suction apertures positioned on at least one of an upper surface or a lower surface of the platform; a plurality of suction apertures positioned on at least one of an upper surface or a lower surface of the tongue positioner, where the at least one suction aperture positioned on the proximal end of the platform and the at least one suction aperture positioned on the proximal end of the tongue positioner are larger than the plurality of suction apertures positioned on the at least one upper surface or lower surface of the platform and the plurality of suction apertures positioned on the at least one upper surface or lower surface of the tongue positioner; where a patient's tongue is positionable above or below the tongue positioner; a head positioning apparatus that utilizes at least one strap to immobilize the patient's head in a position that balances collection of the substances from the patient's mouth and throat with application of the moist gas to desired locations in the patient's mouth and throat; an upper torso straps and leg supports, and/or having the mouth insertion apparatus positioned within the patient's mouth at an angle relative to a vertical axis within a range of +25 to −25 degrees. Implementations of the described techniques may include hardware, a method or process, or a computer tangible medium.

Embodiments of an oral phlegm extraction system may include a mouth insertion apparatus having a platform shaped to engage with a patient's teeth when worn and having at least one suction aperture positioned on a proximal end of the platform and directed toward an entrance to the patient's throat; a tongue positioner joined to the platform, where the tongue positioner may include a region shaped to direct a flow of moist gas toward the entrance to the patient's throat; and/or a hollow interior region in open communication with the at least one platform suction aperture. Embodiments may also include a misting apparatus having a nozzle coupled to a distal end of the platform that is programmable to control at least one of frequency, duration, or content of a moist gas stream that is introduced into the patient's mouth and throat, where the nozzle is positioned so that the moist gas stream flows out of the nozzle and is directed toward the shaped region of the tongue positioner; a suction apparatus having a vacuum pump coupled to the distal end of the platform and in open communication with the hollow interior region of the platform to remove collected substances from the patient's mouth and throat; and/or a head positioning apparatus that utilizes at least one strap to immobilize the patient's head in a position that balances collection of the substances from the patient's mouth and throat with application of the moist gas to desired locations in the patient's mouth and throat. Other embodiments of this aspect include corresponding computer systems, apparatus, and computer programs recorded on one or more computer storage devices, each configured to perform the actions of the methods.

Embodiments may include a plurality of nubs positioned on at least one of an upper surface or a lower surface of the platform, a plurality of suction apertures positioned on at least one of an upper surface or a lower surface of the platform and/or on at least one of an upper surface or a lower surface of the tongue positioner; where the at least one suction aperture positioned on the proximal end of the platform and the at least one suction aperture positioned on the proximal end of the tongue positioner are larger than the plurality of suction apertures positioned on the at least one upper surface or lower surface of the platform and the plurality of suction apertures positioned on the at least one upper surface or lower surface of the tongue positioner; and/or having the mouth insertion apparatus positioned within the patient's mouth at an angle relative to a vertical axis within a range of +25 to −25 degrees. Implementations of the described techniques may include hardware, a method or process, or a computer tangible medium.

According to certain embodiments of the present invention, a method of using an oral phlegm extraction system may include selecting a frequency for the timer to open the nozzle, selecting a duration for the timer to keep the nozzle open, selecting a flowrate of liquid to be provided to the nozzle via the liquid supply system when the nozzle is open, selecting a flowrate of moist gas to be provided to the nozzle via the gas supply system when the nozzle is open, positioning the mouth insertion apparatus into a patient's mouth, actuating the misting apparatus to begin operation, and actuating the suction apparatus to begin operation. Embodiments may include corresponding computer systems, apparatus, and computer programs recorded on one or more computer storage devices, each configured to perform the actions of the methods.

Embodiments may include attaching at least one strap to the patient's head to immobilize the patient's head at a desired angle, wherein the desired angle of the patient's head is one that balances collection of substances from the patient's mouth and throat with application of the moist gas to desired locations in the patient's mouth and throat; attaching at least one strap to the patient's upper torso to immobilize the patient's upper torso posture; placing the patient's legs onto leg supports, where the head and body positioning devices are combined into a unitary apparatus; and/or performing the step of positioning the mouth insertion apparatus such that the mouth insertion apparatus is positioned at an angle relative to a vertical axis within a range of +25 to −25 degrees. Implementations of the described techniques may include hardware, a method or process, or a computer tangible medium.

BRIEF DESCRIPTION OF THE DRAWINGS

Figure 60:
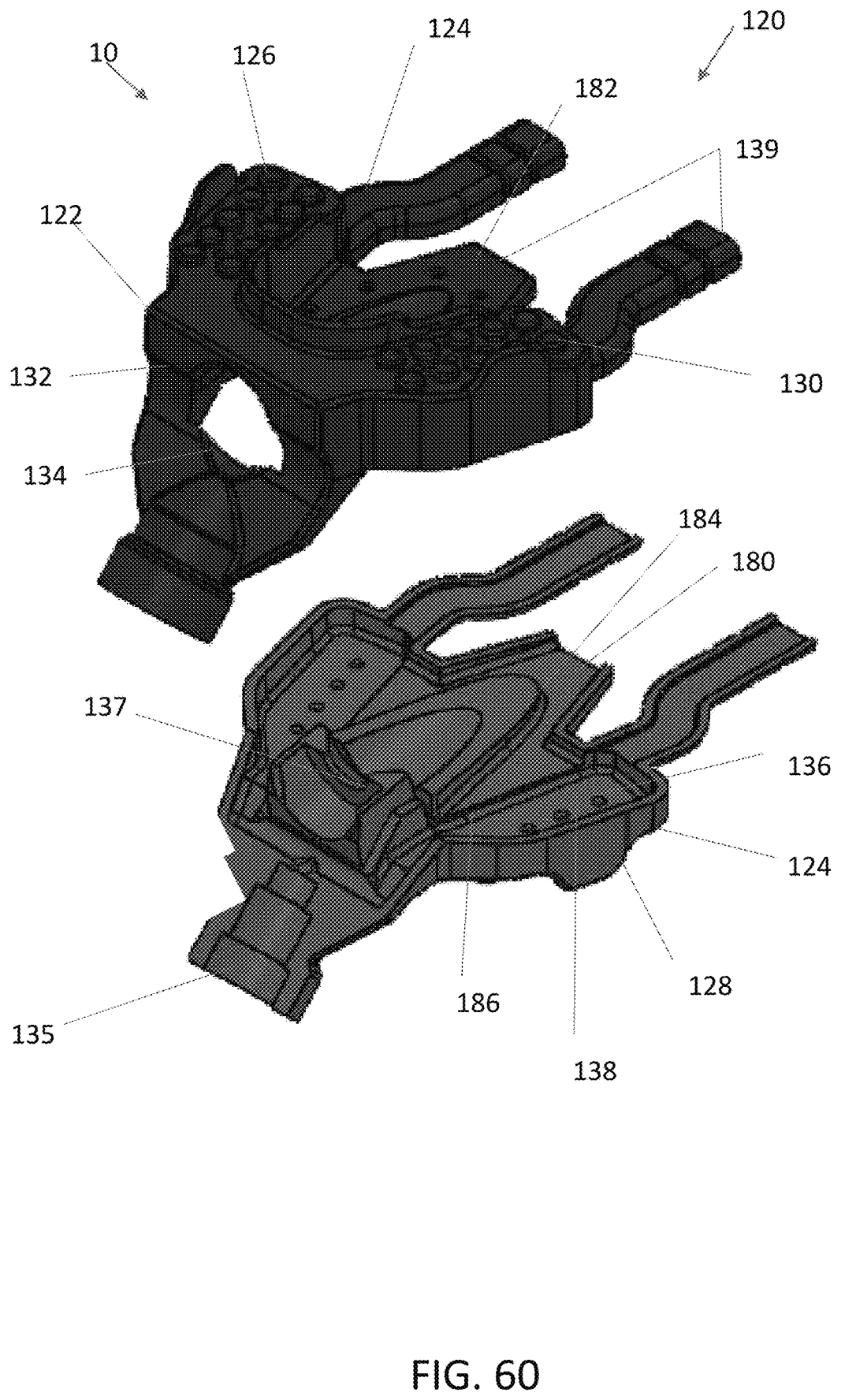

FIG. 60 is an exploded front perspective view of the oral phlegm extraction system of FIG. 59.

DETAILED DESCRIPTION

Figure 1:
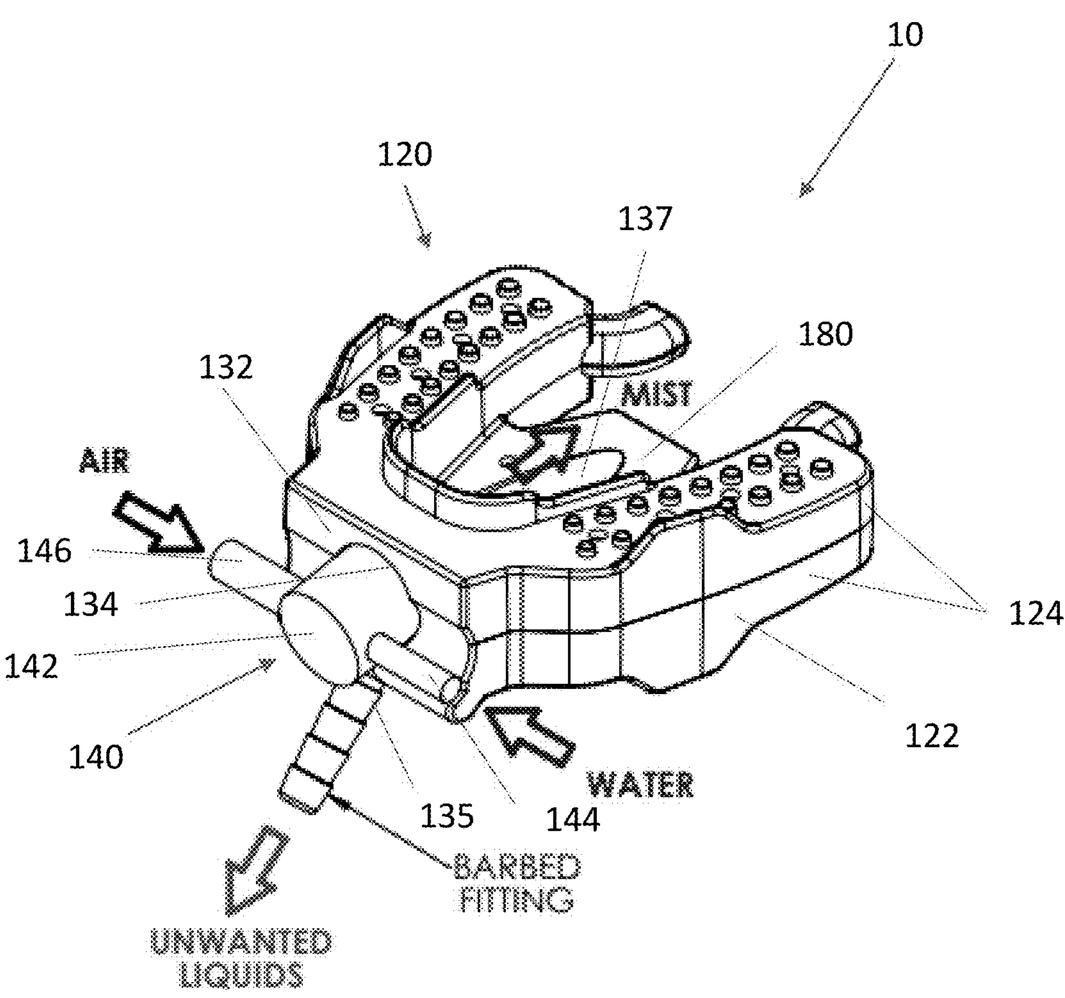
FIG. 1 is a front perspective view of an oral phlegm extraction system comprising a mouth insertion apparatus and portions of a misting apparatus, according to certain embodiments of the present invention.
Figure 2:
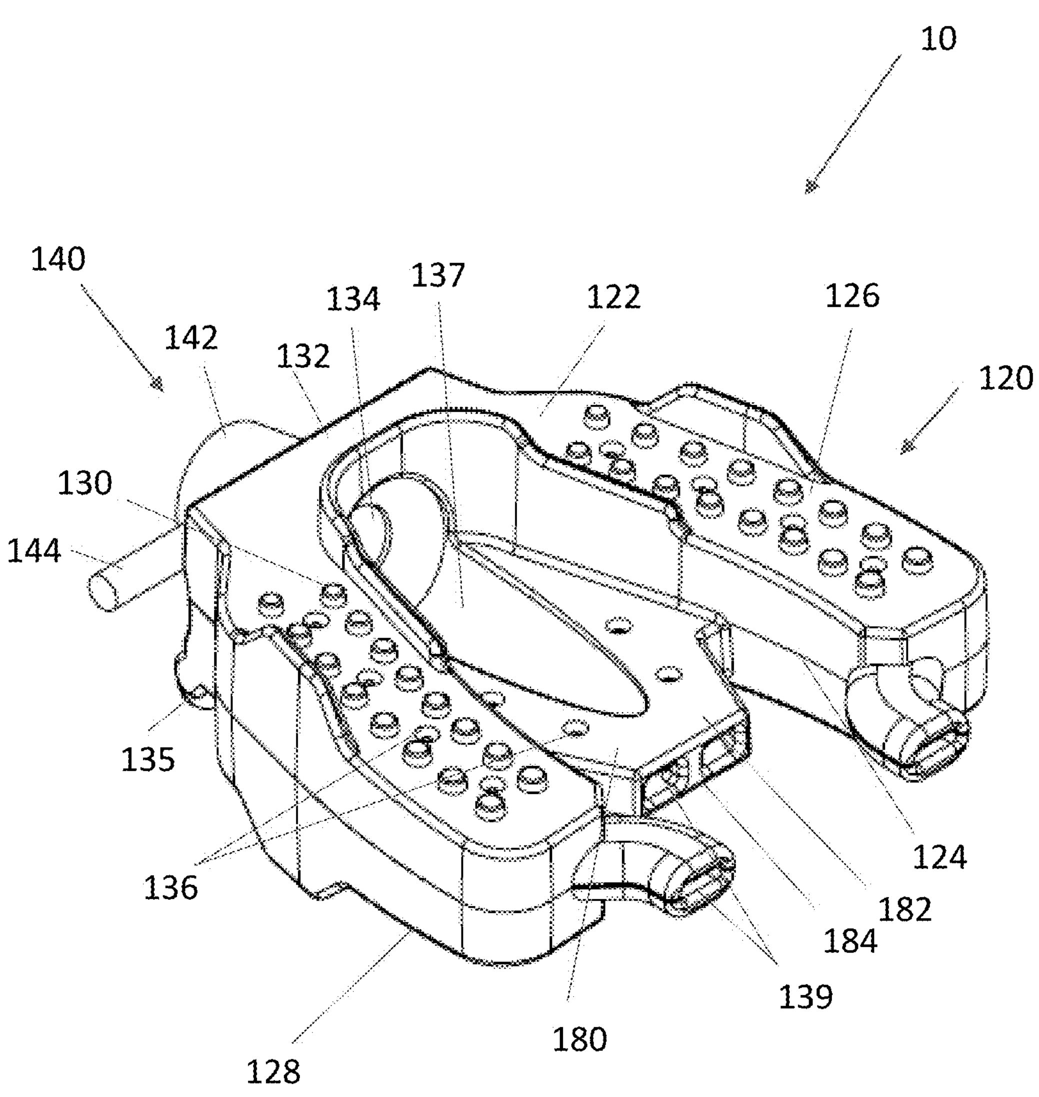
FIG. 2 is a rear perspective view of the oral phlegm extraction system of FIG. 1.
Figure 3:
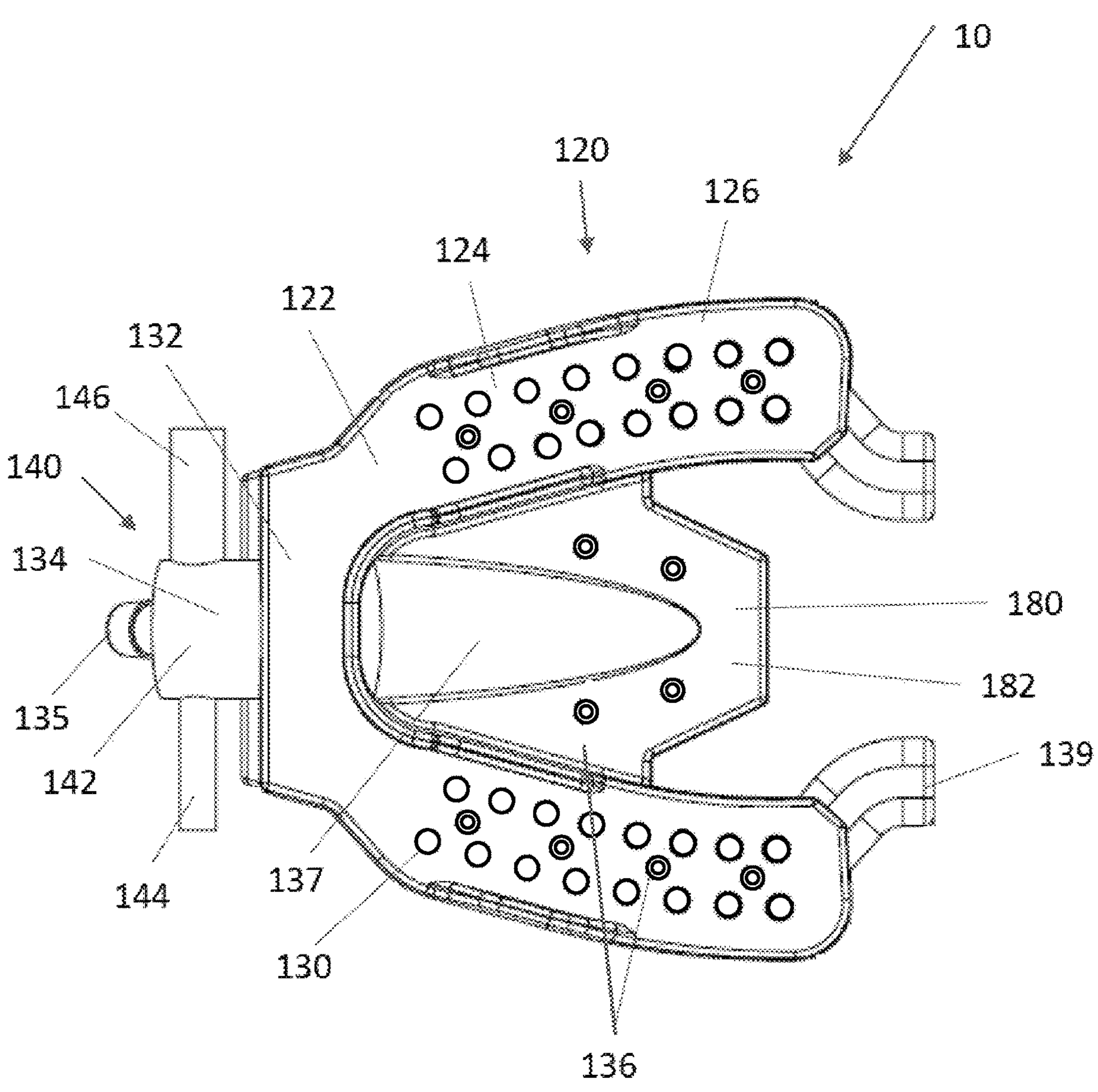
FIG. 3 is a top view of the oral phlegm extraction system of FIG. 1.
Figure 4:
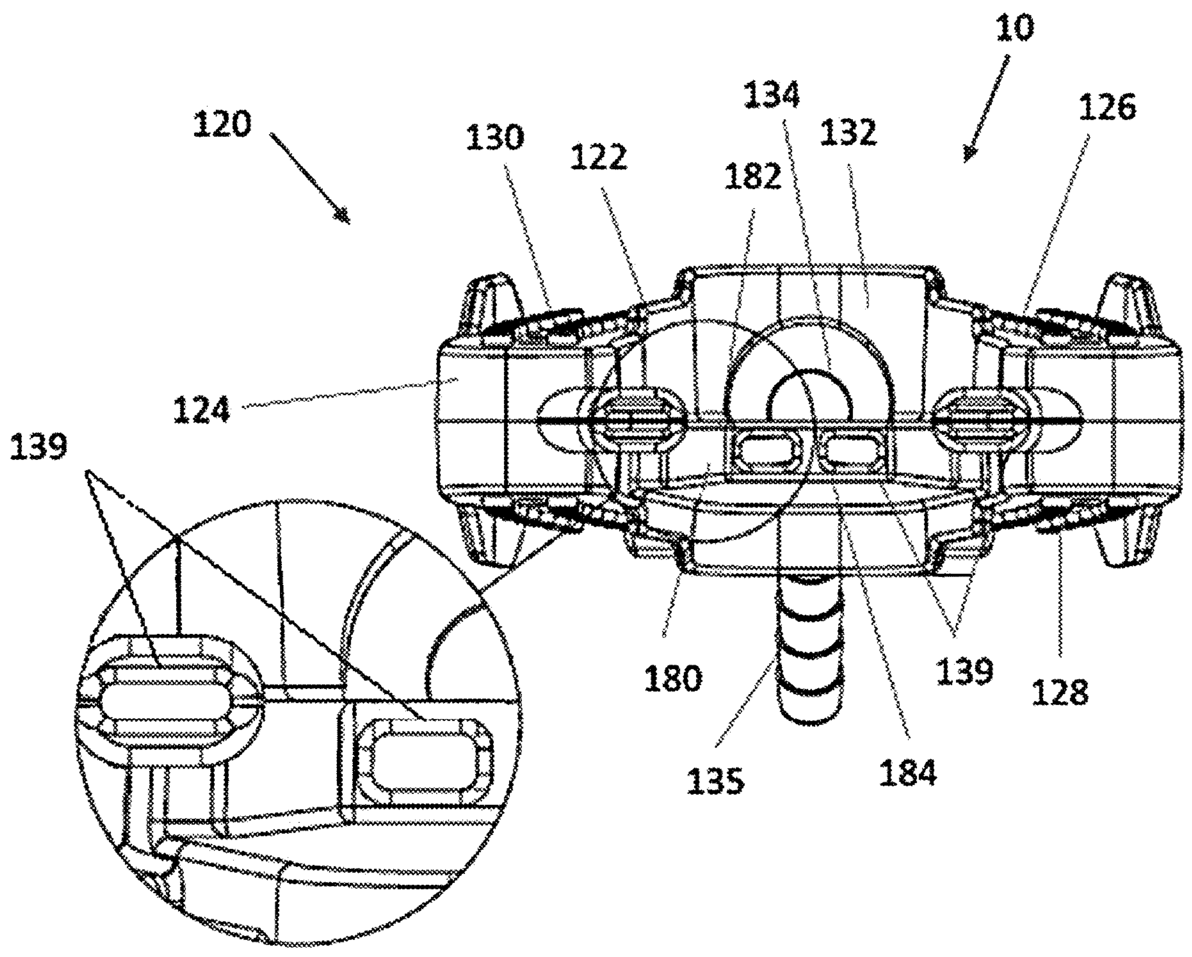
FIG. 4 is a rear view of the oral phlegm extraction system of FIG. 1.
Figure 5:
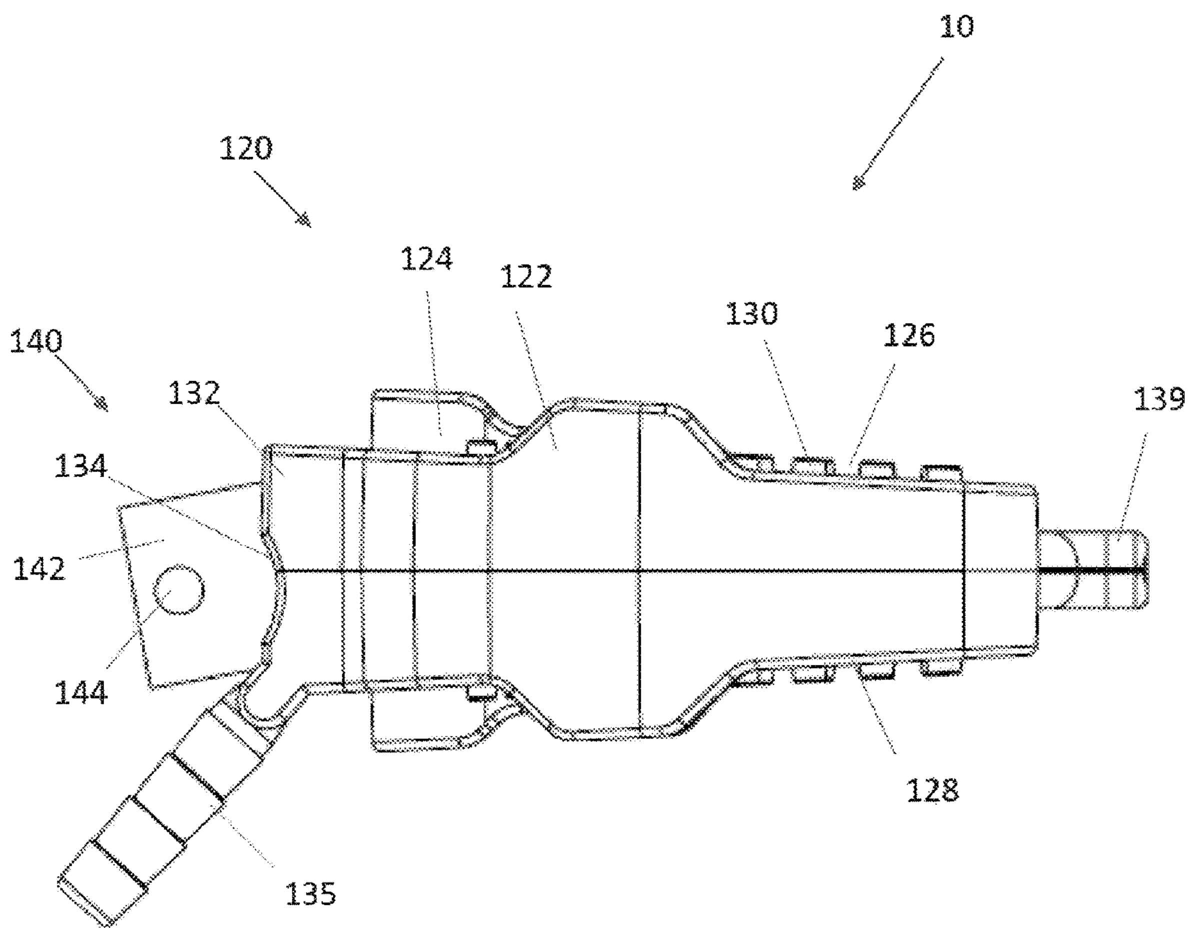
FIG. 5 is a side view of the oral phlegm extraction system of FIG. 1.
Figure 6:
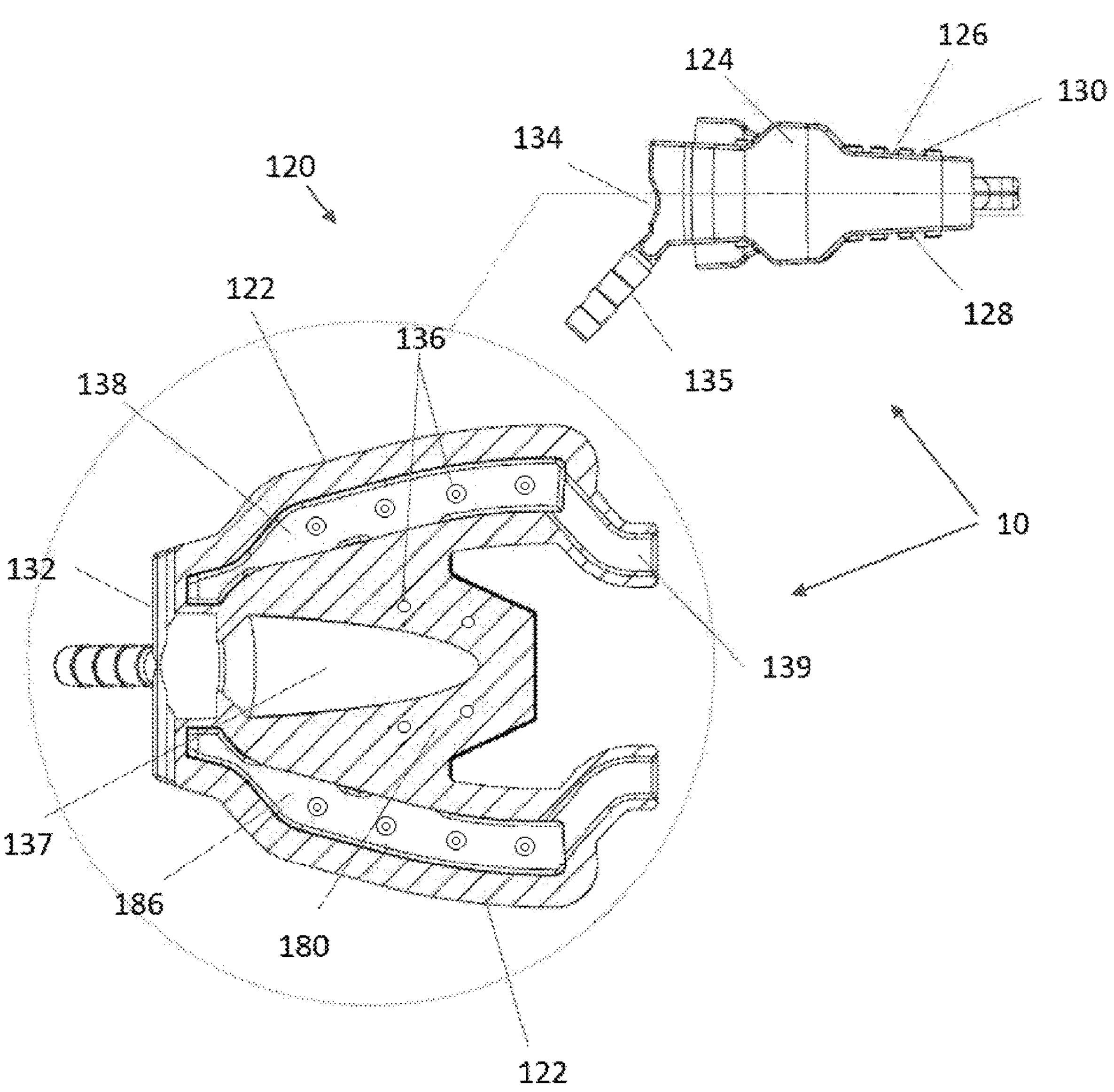
FIG. 6 is a first top cross-sectional view of the oral phlegm extraction system of FIG. 1 with the portions of the misting apparatus removed.
Figure 7:
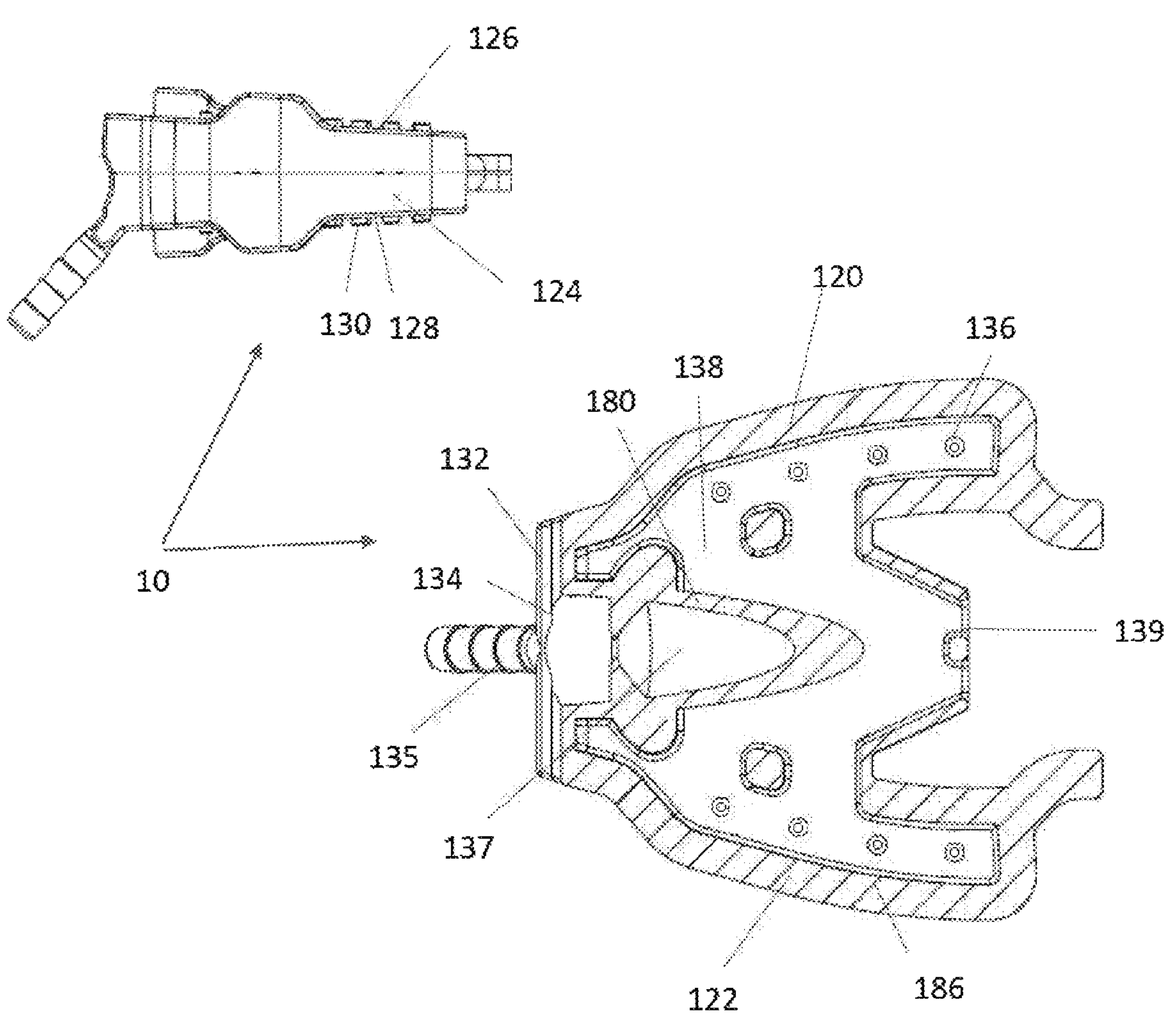
FIG. 7 is a second top cross-sectional view of the oral phlegm extraction system of FIG. 1 with the portions of the misting apparatus removed.
Figure 8:
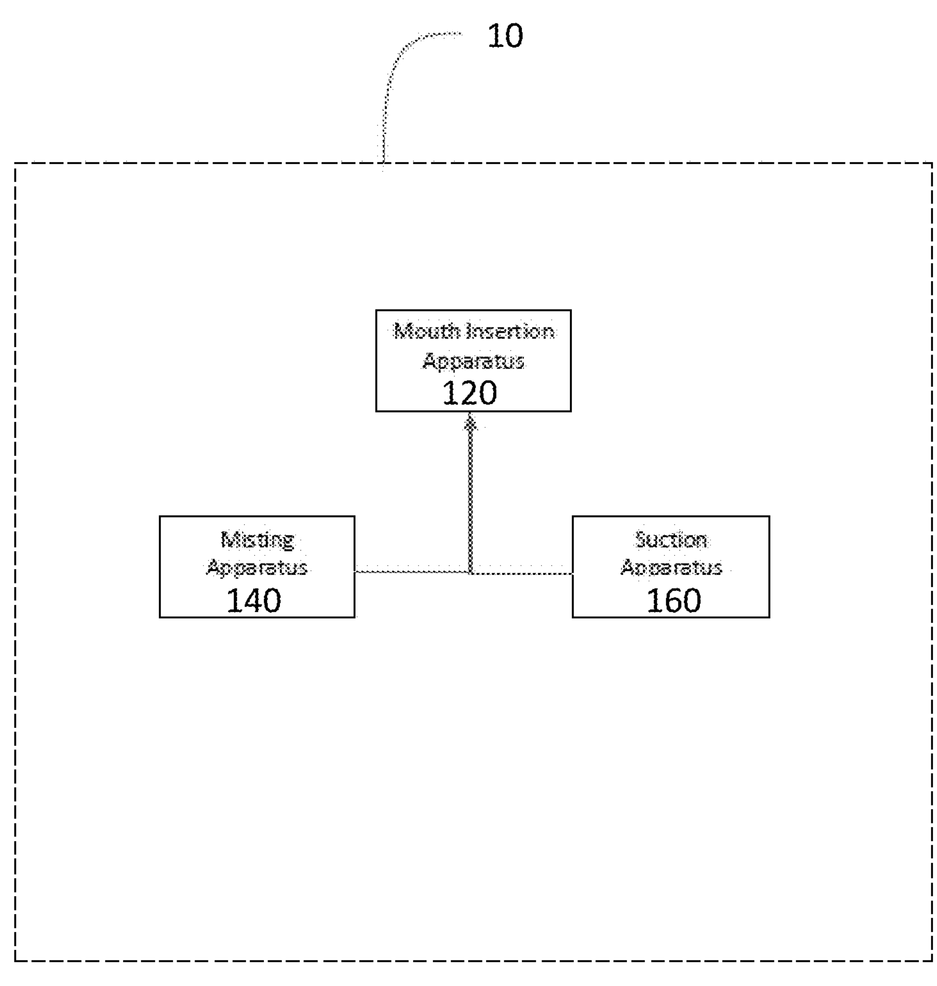
FIG. 8 is a flow diagram of an oral phlegm extraction system, according to certain embodiments of the present invention.

The subject matter of embodiments of the present invention is described here with specificity to meet statutory requirements, but this description is not necessarily intended to limit the scope of the claims. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. This description should not be interpreted as implying any particular order or arrangement among or between various steps or elements except when the order of individual steps or arrangement of elements is explicitly described. The claimed subject matter may be used in conjunction with other existing or future technologies.

Other technical advantages may become readily apparent to one of ordinary skill in the relevant art after review of the following figures and description. Moreover, those of ordinary skill in the relevant art will recognize and appreciate that many changes can be made to the various examples of the invention described herein, while still obtaining the beneficial results of the invention.

As used throughout this document, "each" refers to each member of a set or each member of a subset of a set. Moreover, the singular forms "a," "an" and "the" include plural references unless the context clearly dictates otherwise. Thus, for example, reference to "a fastener" can include two or more such fasteners unless the context indicates otherwise. Ranges can be expressed herein as from "about" one particular value and/or to "about" another particular value. When such a range is expressed, another example includes from the one particular value and/or to the other particular value. Similarly, when values are expressed as approximations, by use of the antecedent "about," the particular value forms another example. Moreover, the endpoints of each of the ranges are significant both in relation to the other endpoint, and independently of the other endpoint.

As used herein, the terms "optional" or "optionally" mean that the subsequently described feature may or may not be present, and that the description includes instances where said feature is present and instances where it is not. The word "or" as used herein means any one member of a particular list and also includes any combination of members of that list.

Further, conditional language, such as, among others, "may," "can," "could," or "might," unless specifically stated otherwise or otherwise understood within the context as used, is generally intended to convey that certain examples include, while other examples do not include, certain features, elements and/or steps. Thus, such conditional language is not generally intended to imply that features, elements and/or steps are in any way required for one or more particular examples.

Directional references such as "up," "down," "top," "bottom," "left," "right," "front," "back," "rear," and "corners," among others, are intended to refer to the orientation as illustrated and described in the figure (or figures) to which the components and directions are referencing. Unless otherwise specifically noted, articles depicted in the drawings are not necessarily drawn to scale.

To aid the Patent Office and any readers of any patent issued on this application in interpreting the claims appended hereto, applicants wish to note that they do not intend any of the appended claims or claim elements to invoke 35 U.S.C. 112 (f) unless the words "means for" or "step for" are explicitly used in the particular claim.

According to certain embodiments of the present invention, as best shown in FIGS. 8-15, the oral phlegm extraction system 10 comprises a mouth insertion apparatus 120, a misting apparatus 140, and a suction apparatus 160.

I. Mouth Insertion Apparatus

In some embodiments, the mouth insertion apparatus 120 comprises a base 122. The base 122 has an overall shape that resembles a mouth protector. In other embodiments, the base 122 may have any suitable shape that allows the base 122 to engage with a patient's teeth and/or gums. For example, the base 122 may have a U-shaped configuration, as best illustrated in FIGS. 1-7, 11-13, 21-45, and 50-65. A person of ordinary skill in the relevant art will understand that the base 122 may have any suitable shape that allows the base 122 to comfortably fit within a patient's mouth and engage with a patient's teeth and/or gums, such as the embodiments illustrated in FIGS. 46-49.

A. Teeth/Gum Platform

For example, in some embodiments, the base 122 comprises a platform 124, wherein the platform 124 is shaped to fit between at least a portion of a patient's upper and lower teeth and/or gums. For example, as best illustrated in FIGS. 1-7 and 21-65, the platform 124 may comprise an upper surface 126 and a lower surface 128. A hollow interior region 138 within the platform 124 may be formed between the upper surface 126 and the lower surface 128.

B. Nubs/Suction Apertures

In some embodiments, as best illustrated in FIGS. 1-7 and 21-65, some or all of the surfaces 126, 128 may include a plurality of nubs 130 and/or suction apertures 136. The nubs 130 may be included to provide some comfort to the patient when biting down on the platform 124 and to also prevent over-suctioning that could occur between the suction apertures 136 located on the platform 124 and a patient's teeth and/or gums. In addition to the nubs 130 themselves, the platform 124 may be formed of a flexible and somewhat soft material for the patient's comfort. A suitable material may be the type of material used for a child's teething ring or similar object. A person of ordinary skill in the relevant art will understand that the choice of material may be any suitable material that provides the desired softness and tactile response for the patient. Examples of such materials include but are not limited to clear silicone, which may have a 40 on the Shore hardness scale.

C. Tongue Positioner

According to some embodiments, as best illustrated by FIGS. 1-7, 21-28, and 42-65, the base 122 comprises a tongue positioner 180, which may be positioned within an open region of the platform 124. Like the platform 124, the tongue positioner 180 may comprise an upper surface 182 and a lower surface 184. A hollow interior region 186 within the tongue positioner 180 may be formed between the upper surface 182 and the lower surface 184.

In some embodiments, some or all of the surfaces 182, 184 may include a plurality of nubs 130 and/or suction apertures 136.

The tongue positioner 180 may be used to keep a patient's tongue out of the way while moist gas is being introduced through the mouth insertion apparatus 120. That being said, in the event that an item becomes stuck or attached to a bottom of a patient's tongue, the patient has the ability to place the tongue on top of the upper surface 182 and use the apertures 136 and/or the upper surface 182 itself to scrub the bottom of his or her tongue without the need to remove or adjust the mouth insertion apparatus 120.

D. Suction Apertures/Openings

In some embodiments, a plurality of apertures 136 may be formed within one or more of the surfaces 126, 128, 182, and 184. For example, as best illustrated in FIGS. 1-7 and 21-65, each platform surface 126, 128, 182, 184 comprises four apertures 136. A person of ordinary skill in the relevant art will understand that the number of apertures 136 may vary along each surface 126, 128, 182, 184, and the number may range between 0-20, more specifically 0-16, even more specifically 0-10, and even more specifically 0-4 on each surface 126, 128, 182, 184. The diameter of the apertures 136 may also vary along each surface 126, 128, 182, 184, and the diameter may range between 0-0.1, more specifically 0-0.08, even more specifically 0-0.04, and even more specifically 0-0.02 on each surface 126, 128, 182, 184. The apertures 136 are configured to provide an opening for various fluids and smaller items to be introduced into the hollow interior regions 138, 186. Moreover, the hollow interior regions 138, 186 may be in open communication with each other, thus creating a hollow interior region that is located throughout the mouth insertion apparatus 120.

In some embodiments, the hollow interior regions 138, 186 may further comprise one or more larger openings 139. For example, one or more larger openings 139 may be positioned at the proximal ends of the hollow interior region 138, which are closer to the entrance of a patient's throat. Similarly, one or more larger openings 139 may be positioned at the proximal end of the tongue positioner 180, which are also closer to the entrance of a patient's throat. The larger openings 139 are configured to provide access for larger volumes of fluid, as well as mucus and phlegm (which may be too large or too far in the back of the throat to be removed by the smaller apertures 136) to be introduced into the hollow interior region 138.

E. Front Portion

The base 122 may further comprise a front portion 132, which is positioned in a front region of the platform 124 and distal to the tongue positioner 180. The front portion 132 comprises an inlet opening 134 and an outlet opening 135.

With respect to the inlet opening 134, it may include a region 137 along a central region of the upper surface 182 of the tongue positioner 180. The region 137 may be configured to help direct/introduce a flow of moist gas into a desired region of a patient's throat. A person of ordinary skill in the relevant art will understand that any suitable shape for the region 137 may be used that provides the desired treatment of a patient's throat.

With respect to the outlet opening 135, it may be positioned through the front portion 132 so that it is in open communication with the hollow interior regions 138, 186. As a result, all of the fluid, mucus, and phlegm that is collected by the mouth insertion apparatus 120 can drain through the outlet opening 135 so that these items do not pass down the patient's throat and irritate and/or harm the recent incisions therein. In certain embodiments, such as those best illustrated in FIGS. 1-7, 21-24, 29-33, and 38-49, the outlet opening 135 may include a barbed fitting for ease of attachment of a hose 162 or other similar device for connecting the mouth insertion apparatus 120 to the suction apparatus 160.

II. Misting Apparatus

In some embodiments, as best illustrated in FIGS. 1-5, 9, and 50-53, the misting apparatus 140 may be joined to the inlet opening 134 via a nozzle 142. The nozzle 142 may include at least one liquid inlet port 144 and at least one gas inlet port 146.

A. Liquid Supply System

Figure 9:
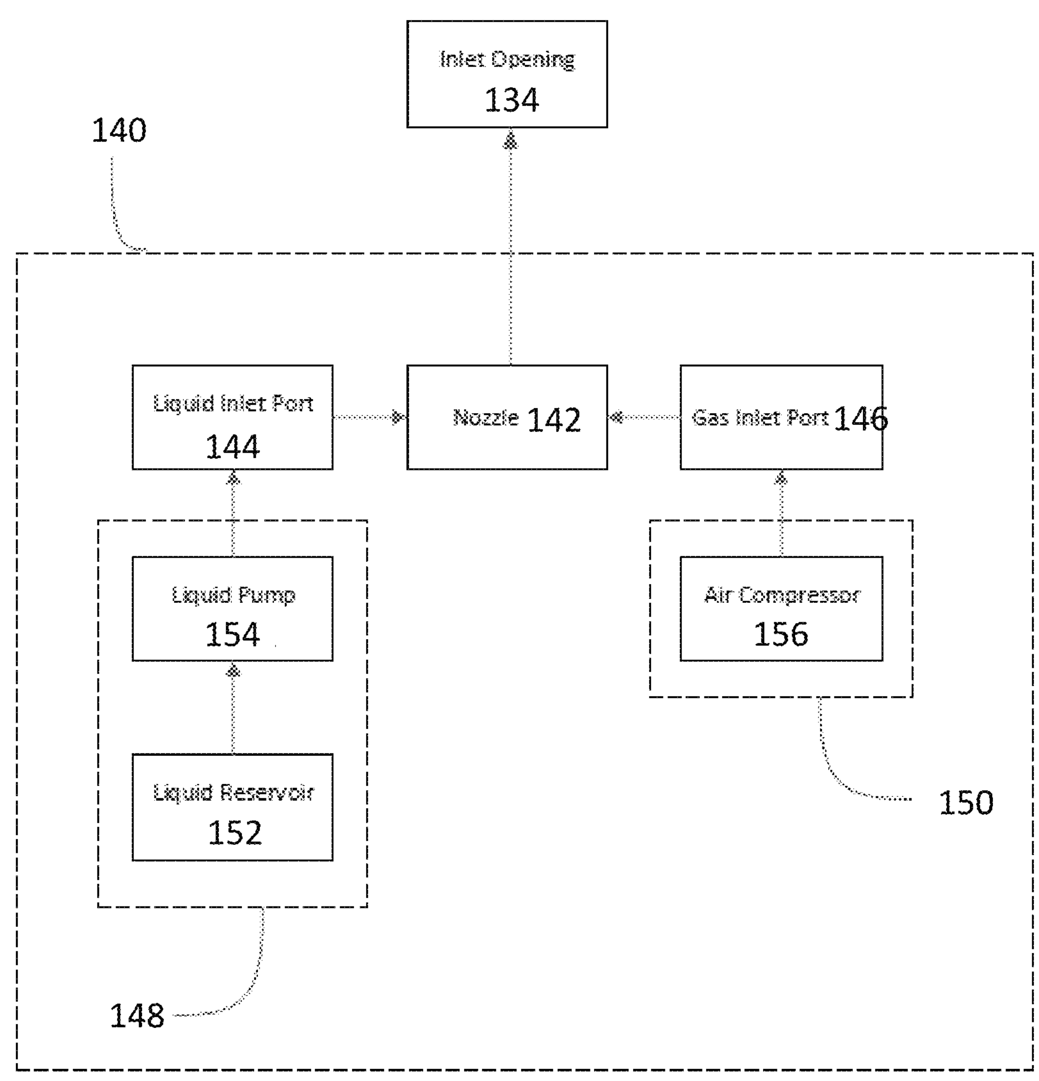
FIG. 9 is a flow diagram of a misting apparatus, according to certain embodiments of the present invention.
Figure 10:
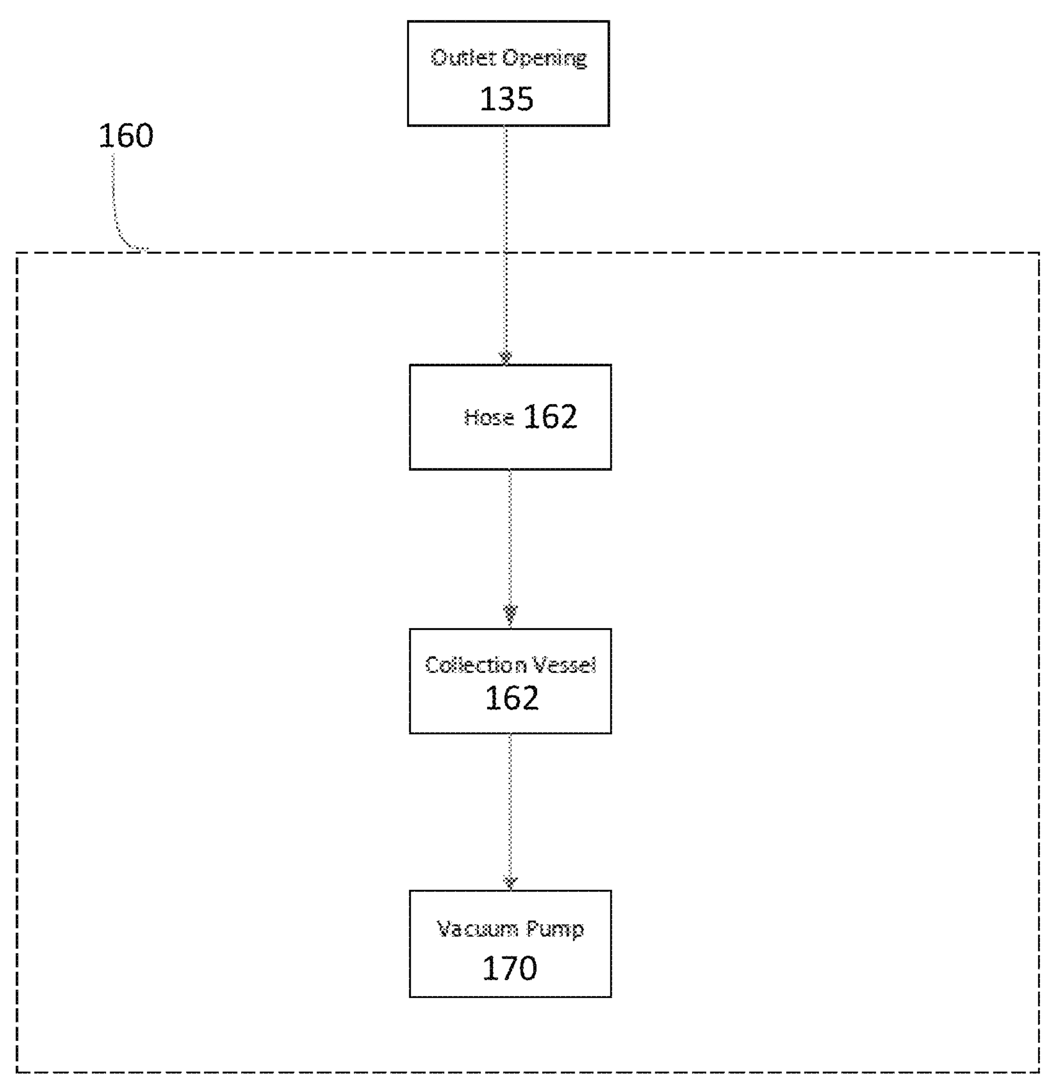
FIG. 10 is a flow diagram of a suction apparatus, according to certain embodiments of the present invention.
Figure 11:
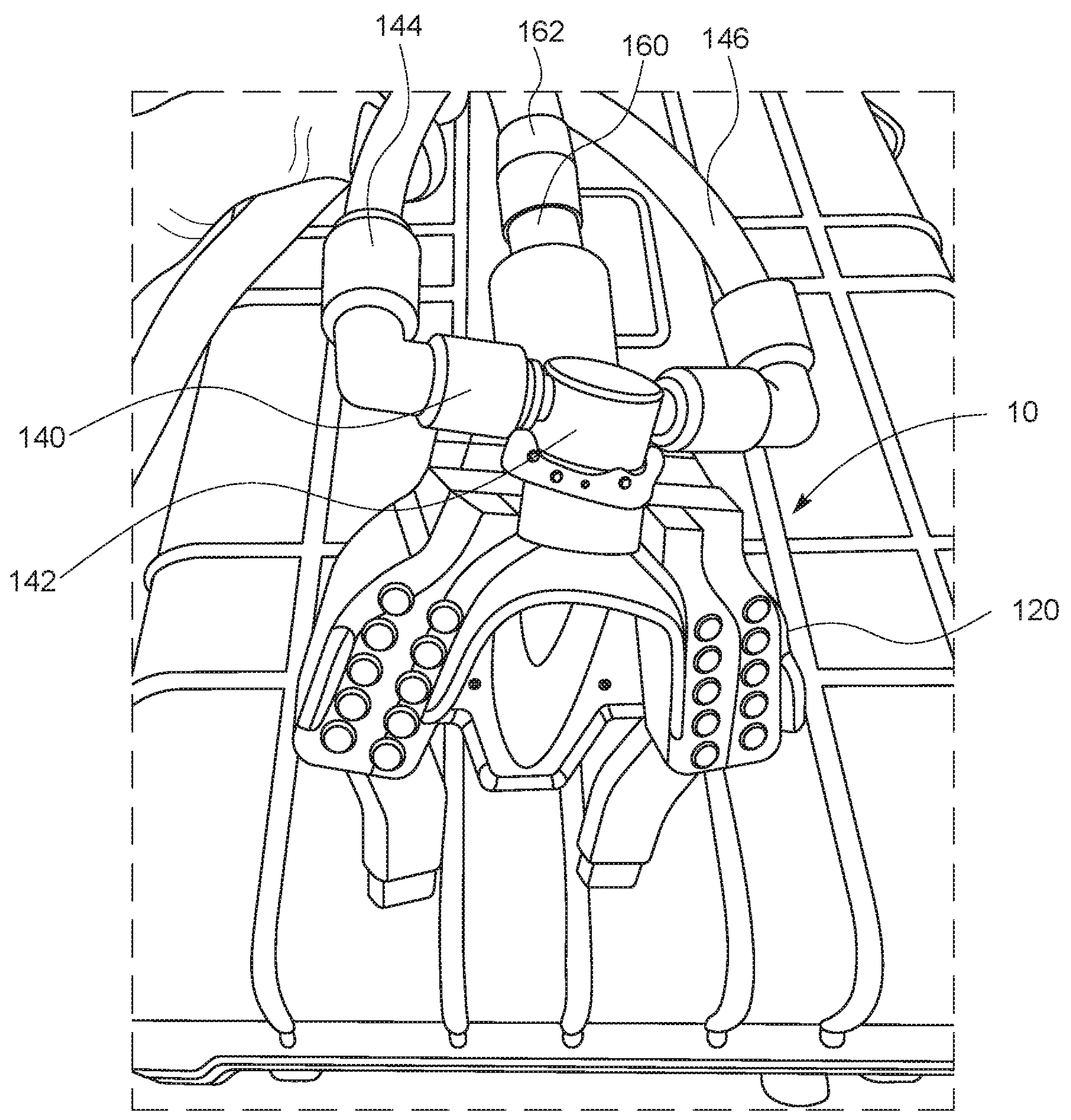
FIG. 11 is an image of an oral phlegm extraction system comprising a mouth insertion apparatus and portions of a misting apparatus, according to certain embodiments of the present invention.
Figure 12:
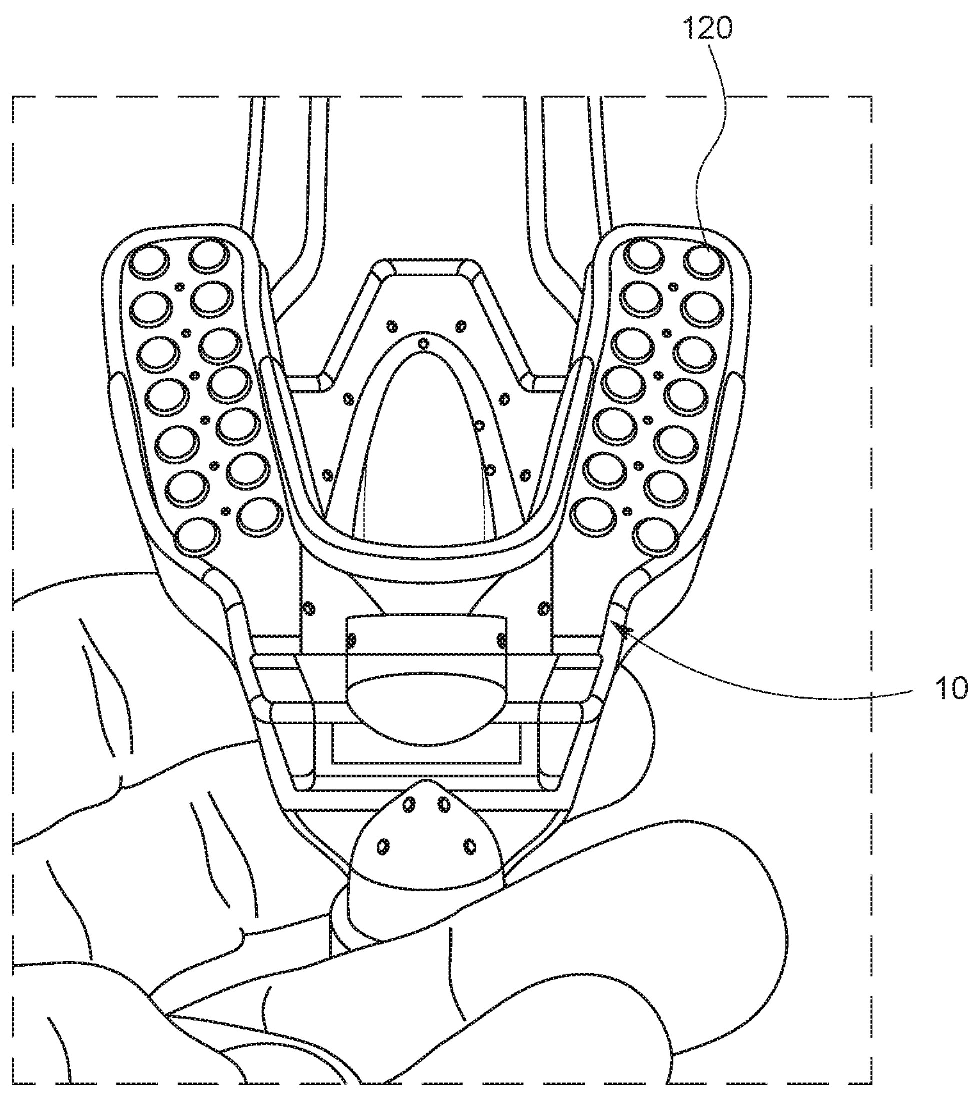
FIG. 12 is an image of the oral phlegm extraction system of FIG. 1 with portions of the misting apparatus removed.
Figure 13:
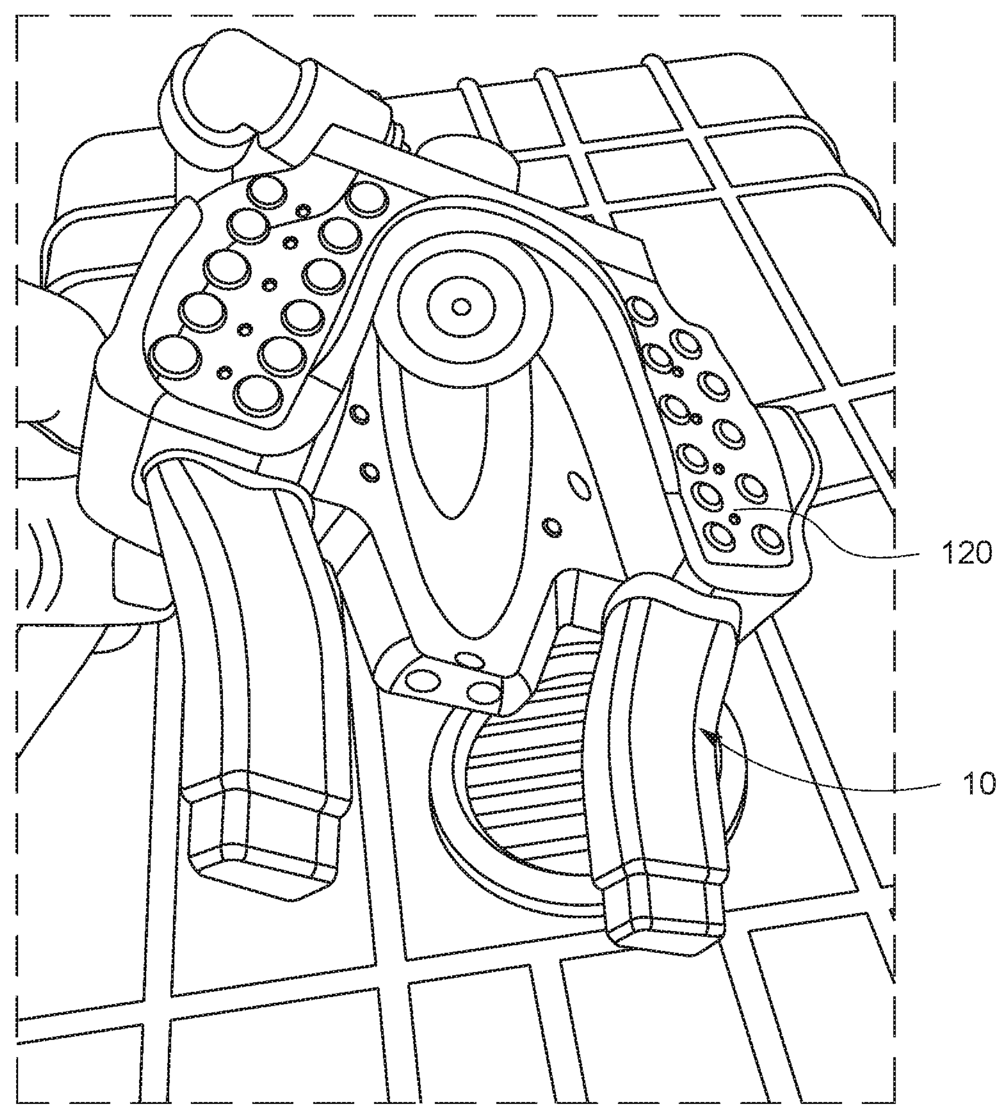
FIG. 13 is another image of the oral phlegm extraction system of FIG. 1.
Figure 14:
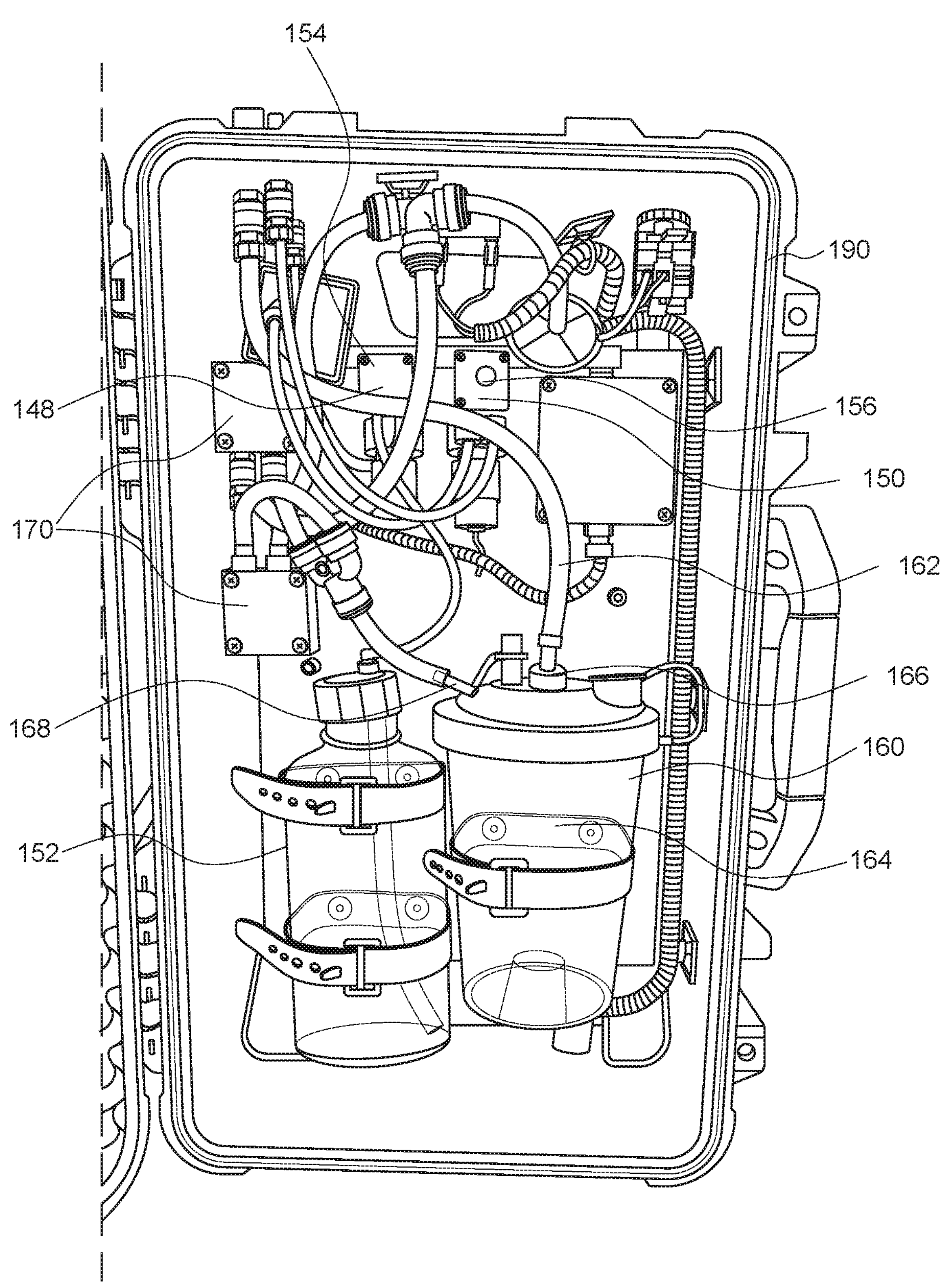
FIG. 14 is an image of portions of a misting apparatus and a suction apparatus housed within a carrying case, according to certain embodiments of the present invention.
Figure 15:
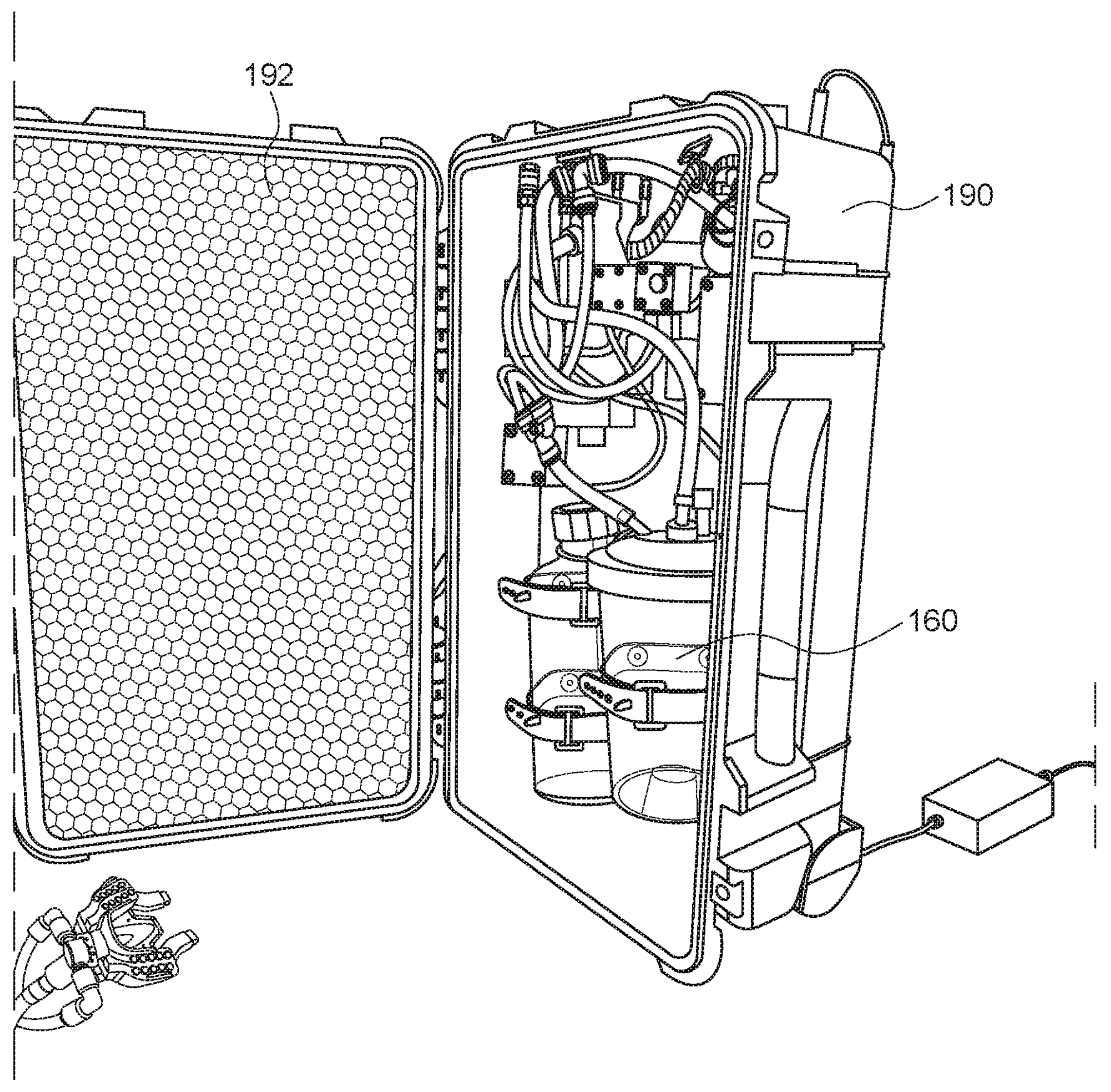
FIG. 15 is another image of the misting apparatus and the suction apparatus housed within the carrying case of FIG. 14.

In some embodiments, as best illustrated in FIGS. 9 and 14-15, a liquid is supplied to the liquid inlet port 144 via a liquid supply system 148. In this system 148, liquid is added to a liquid reservoir 152. As an example, a suitable reservoir may hold up to 2 quarts of liquid.

The reservoir 152 is coupled to an inlet side of a liquid pump 154. As an example, a suitable liquid pump 154 may comprise any pump having a flow rate of between 0.2-0.5 L/min. An outlet side of the liquid pump 154 is coupled to the liquid inlet port 144. The liquid used may be water, medicine, numbing solution, and/or a combination of any of the above or other suitable treatment solutions. Examples of medications that may be combined with water include but are not limited to medications that further soothe/relieve pain in the mouth and/or throat and/or kill bacteria.

B. Gas Supply System

In some embodiments, as best illustrated in FIGS. 9 and 14-15, a gas is supplied to the gas inlet port 146 via a gas supply system 150. In this system 150, an outlet side of a compressor 156 is coupled to the gas inlet port 146. As an example, a suitable compressor 156 may comprise any compressor that is approved for medical use (e.g., oil-free) having a flow rate of between 0.5-1.0 CFM. The gas used may be ambient air.

C. Nozzle

In some embodiments, as best illustrated in FIGS. 1-4, 9, 11, and 50-53, the nozzle 142 mixes the incoming gas and liquid into a moist gas flow that is introduced into the front portion 132 of the mouth insertion apparatus 120. As an example, a nozzle 142 may comprise any nozzle that is capable of handling the range of flowrates for the liquid and gas components described above and providing a generally homogeneous mixture of the gas and liquid prior to introduction into a patient's mouth.

D. Timer and Flowrate

In many embodiments, it is desirable for the gas and liquid to be intermittently introduced into the nozzle 142. The frequency, duration, and moisture concentration of the flow of moist gas is often adjusted over time as the patient recovers. For example, the following chart illustrates how these variables may be adjusted over time.

| | Frequency | Duration | Moisture Concentration |
|---|---|---|---|
| Day 1 | Every 30 seconds | 5-10 seconds | 10%-15% |
| Day 7 | Every 2 minutes | 30-45 seconds | 15%-20% |
| Day 14 | Every 5 minutes | 45-55 seconds | 20%-25% |

Figure 16:
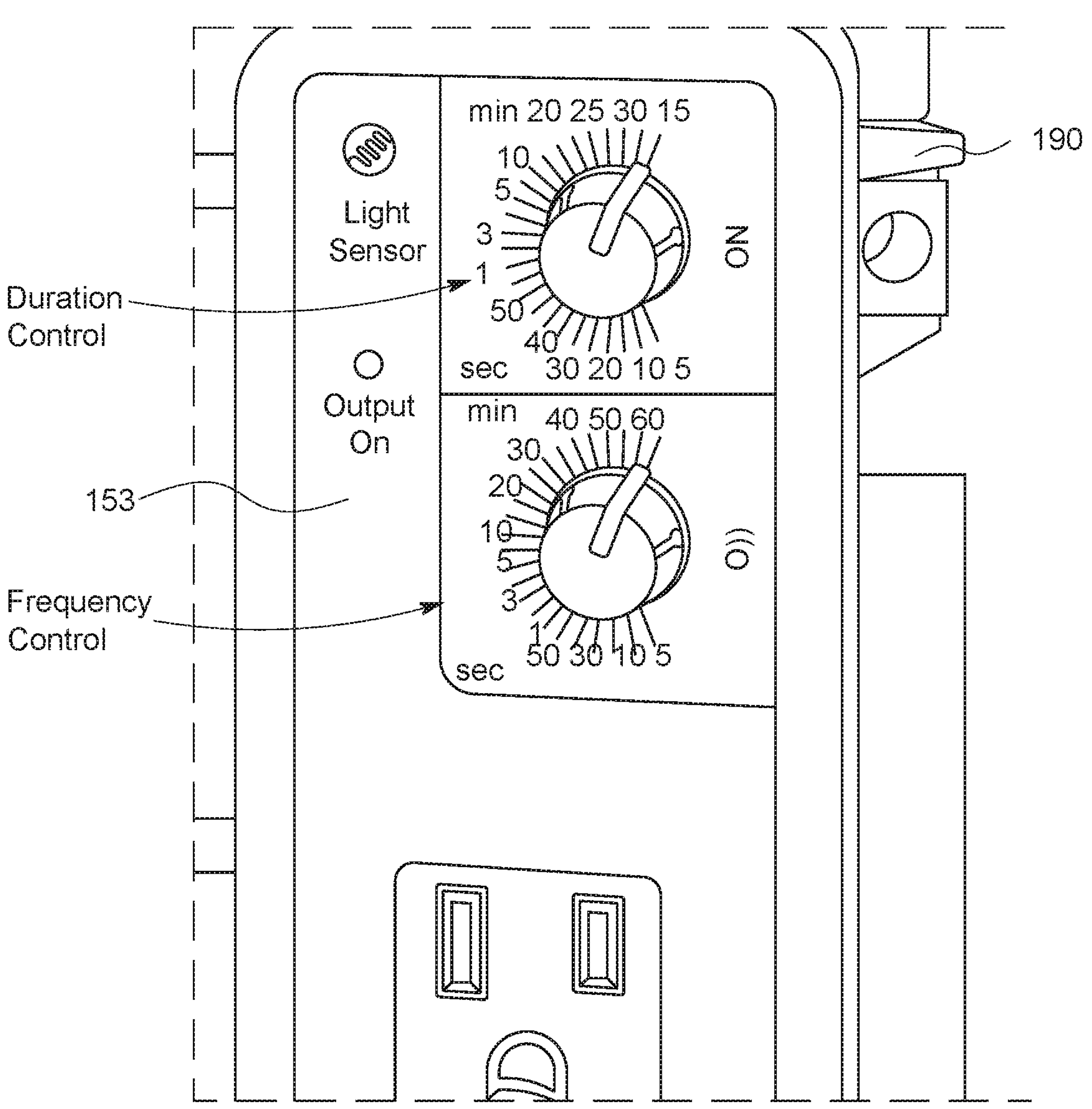
FIG. 16 is an image of a timer located on an exterior surface of a carrying case, according to certain embodiments of the present invention.
Figure 17:
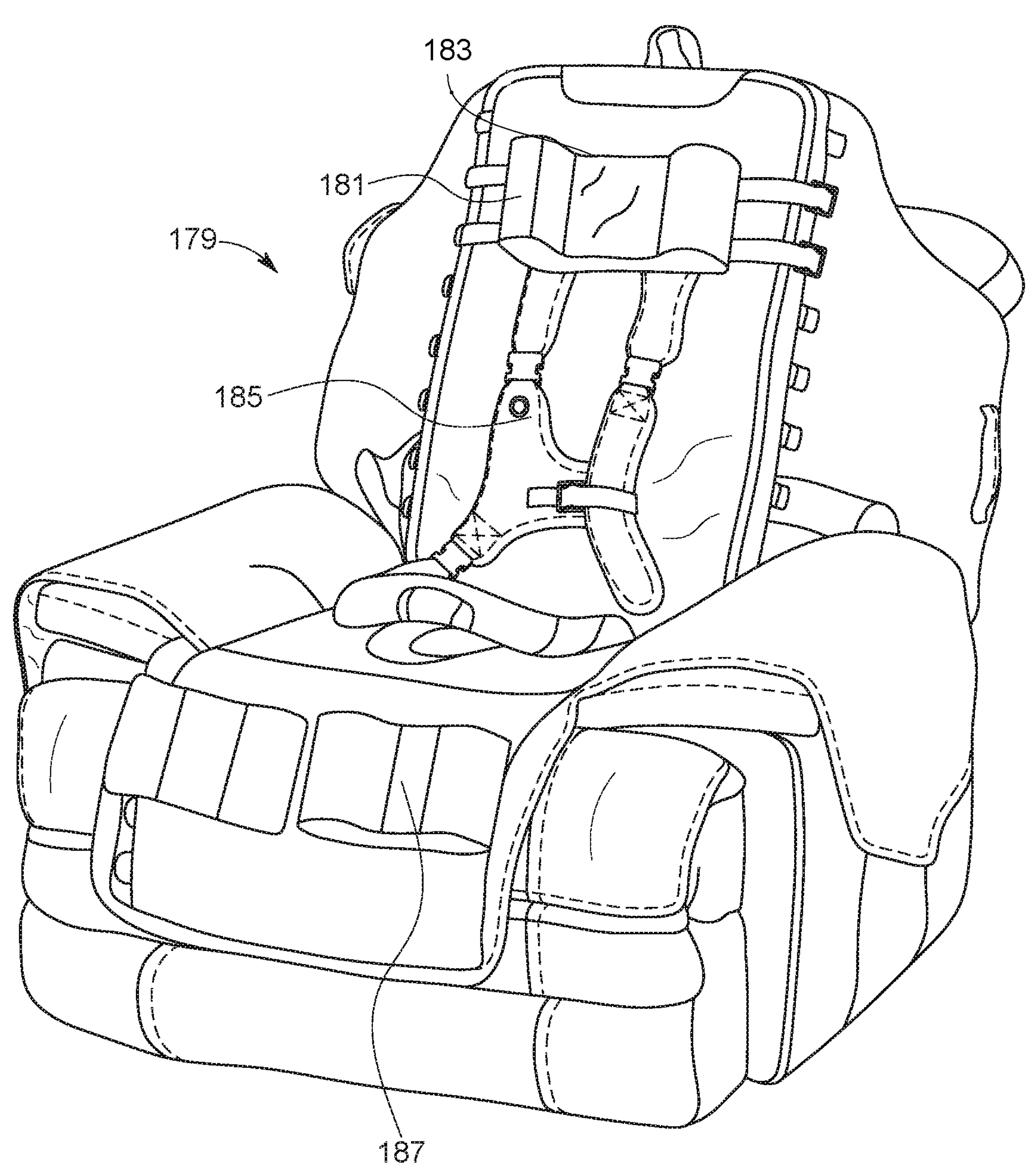
FIG. 17 is an image of a positioning apparatus, according to certain embodiments of the present invention.
Figure 18:
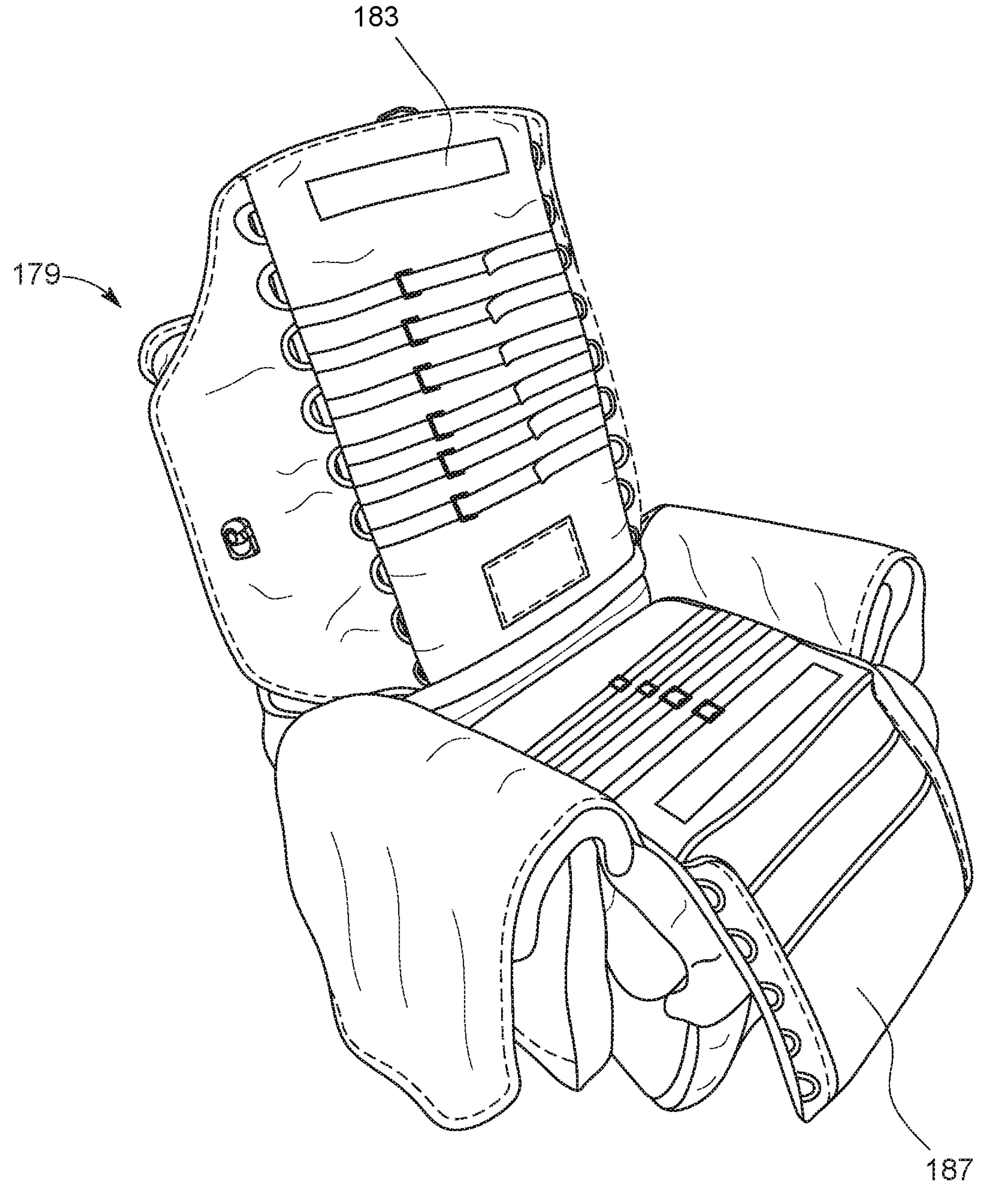
FIG. 18 is an image of a positioning apparatus, according to certain embodiments of the present invention.
Figure 19:
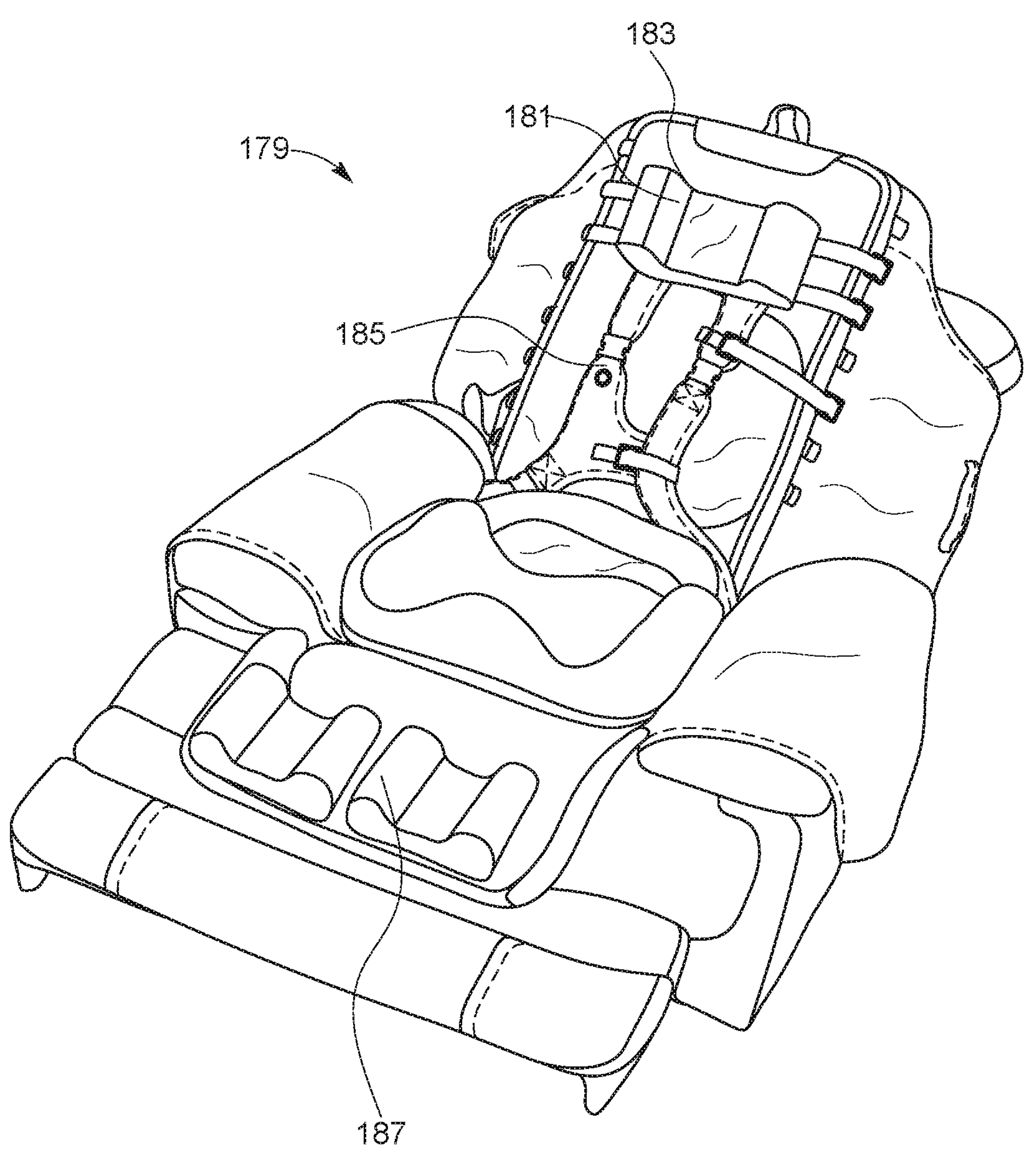
FIG. 19 is an image of a positioning apparatus, according to certain embodiments of the present invention.
Figure 20:
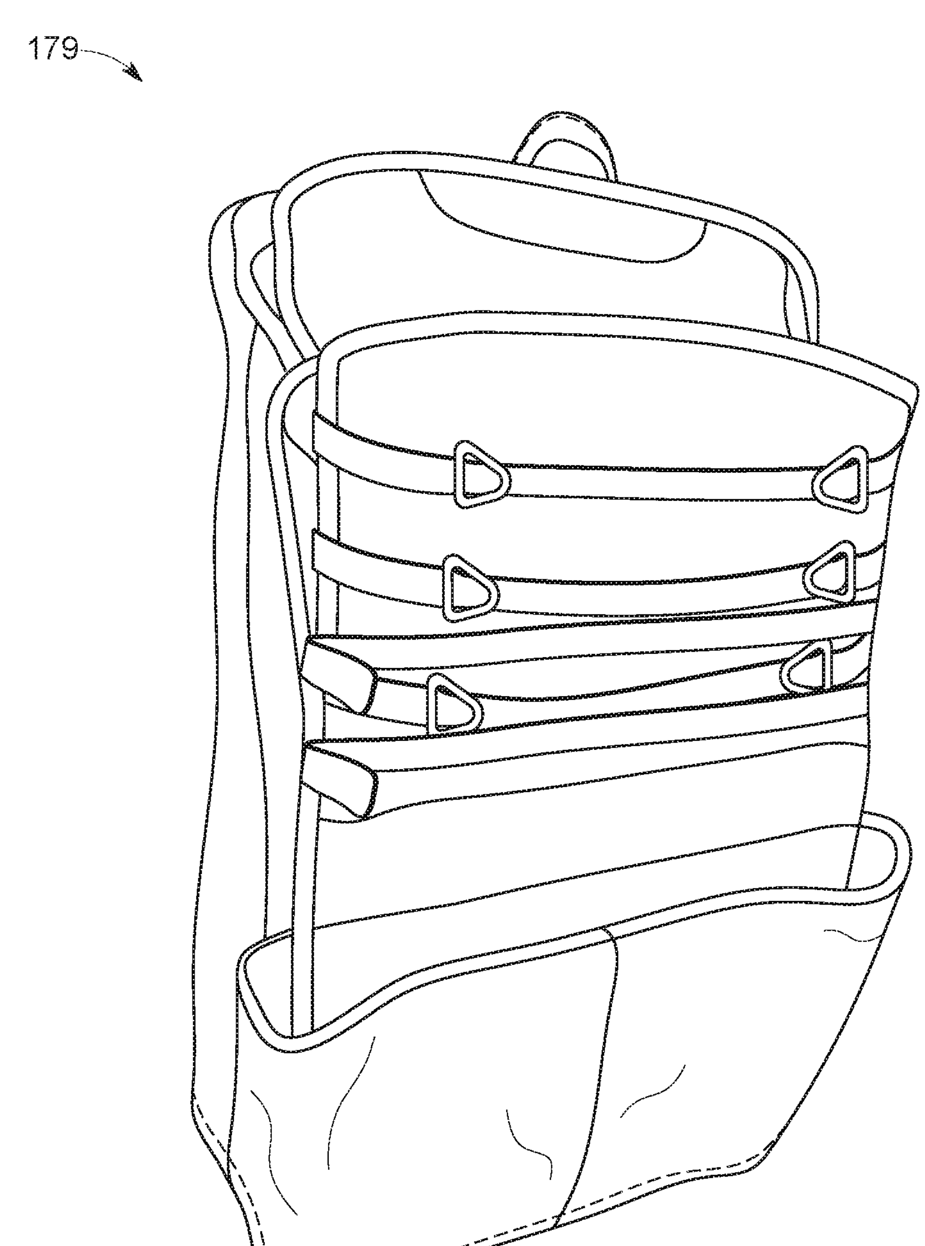
FIG. 20 is an image of a positioning apparatus in a folded position, according to certain embodiments of the present invention.
Figure 21:
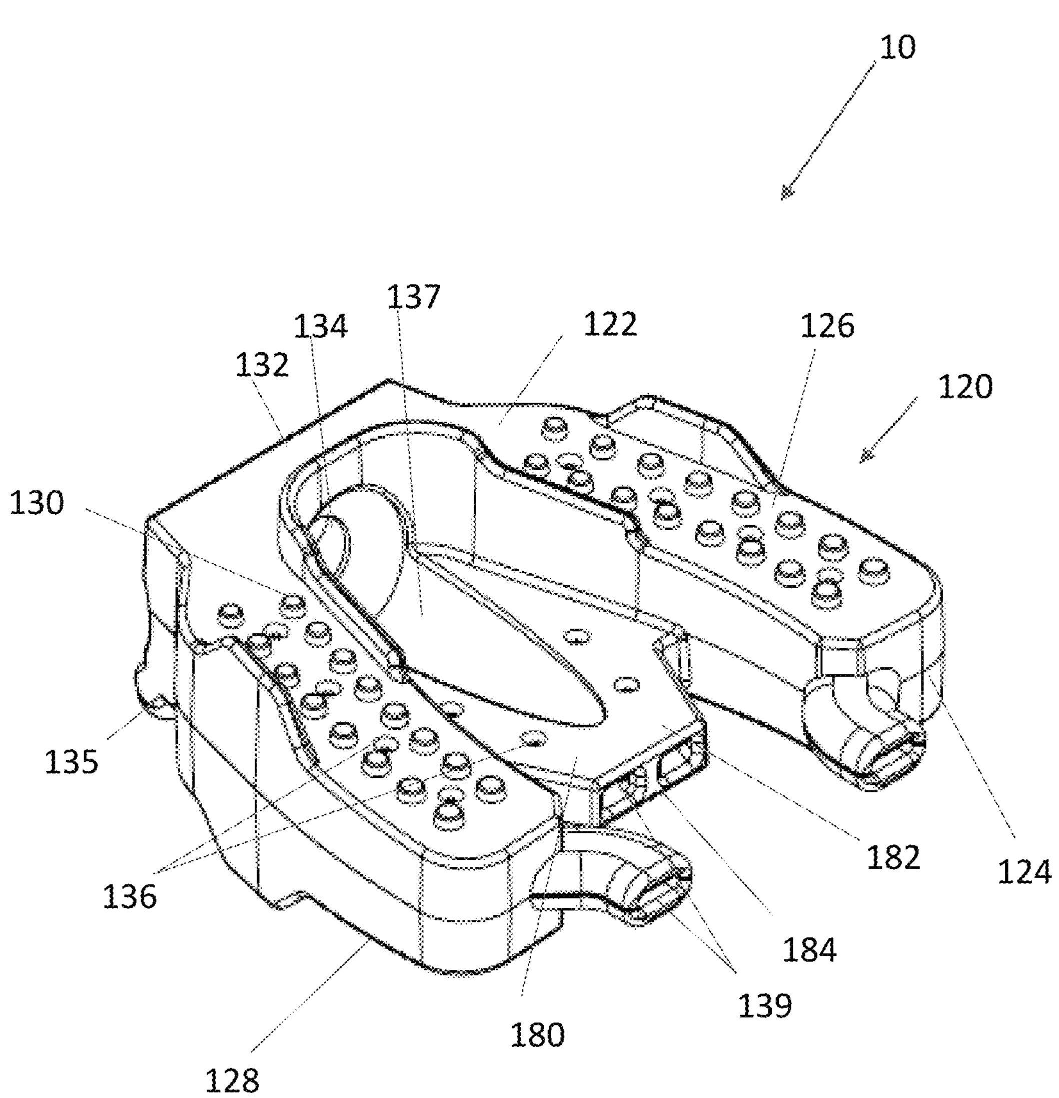
FIG. 21 is a rear perspective view of a mouth insertion apparatus, according to certain embodiments of the present invention.
Figure 22:
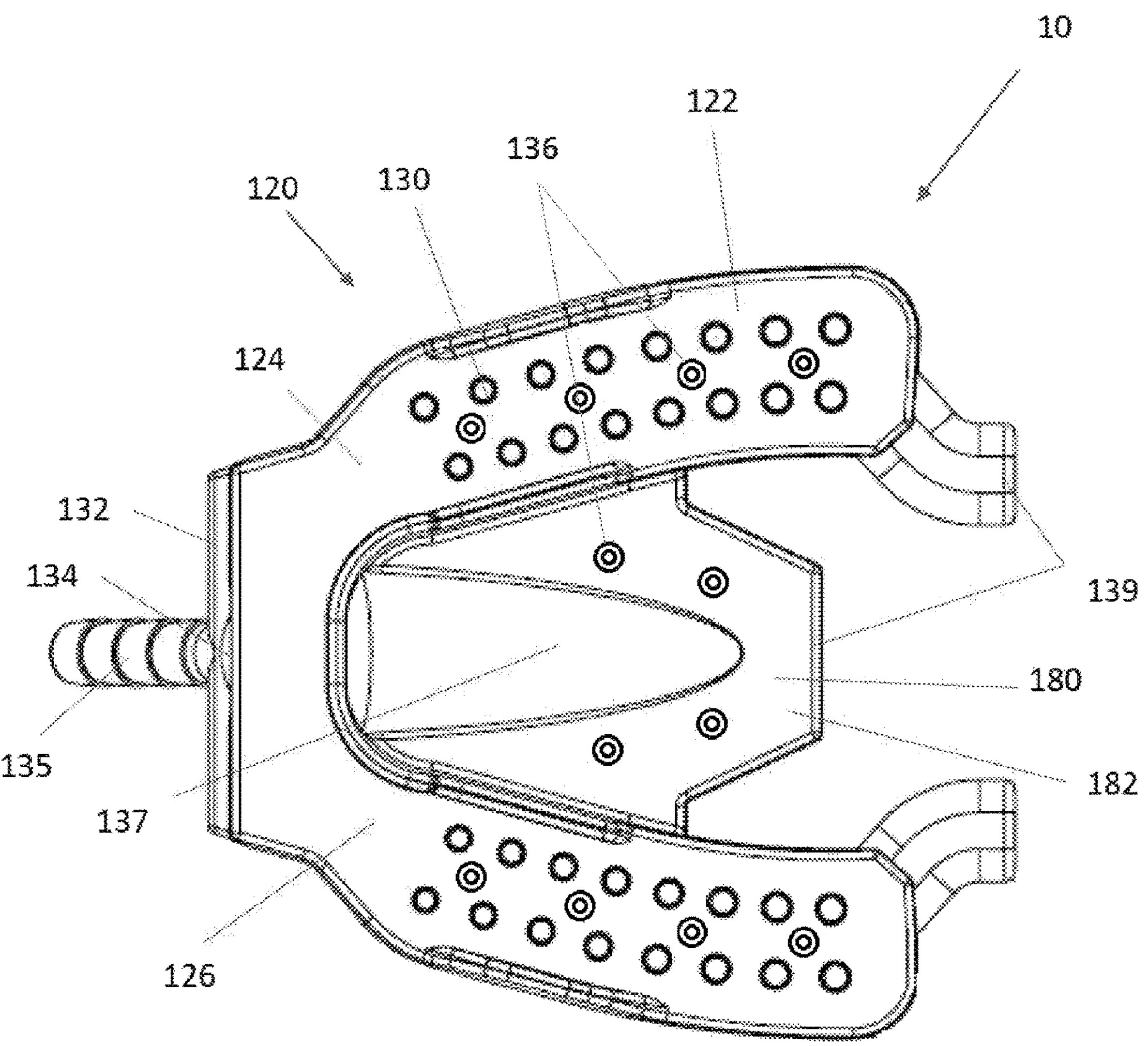
FIG. 22 is a top view of the mouth insertion apparatus of FIG. 21.
Figure 23:
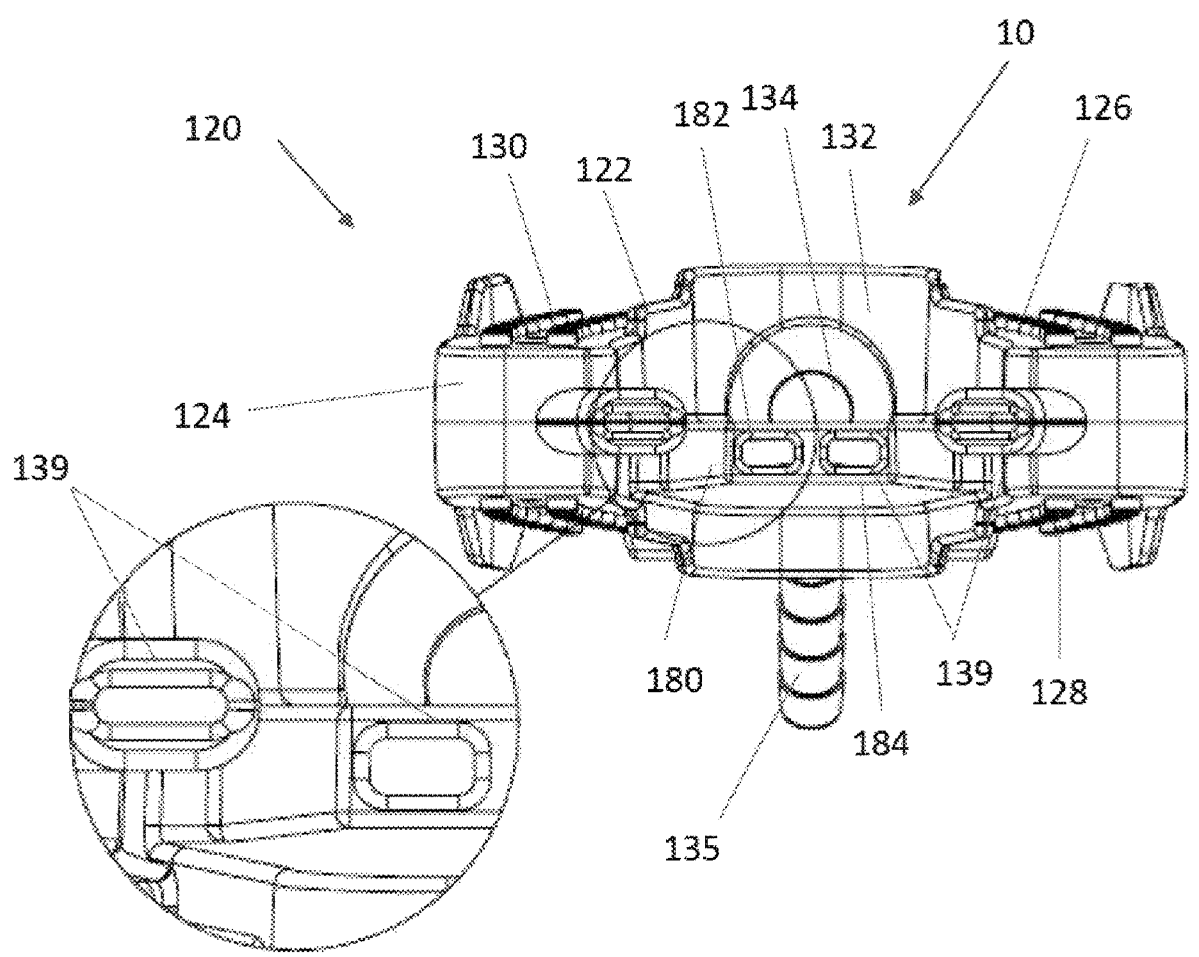
FIG. 23 is a rear view of the mouth insertion apparatus of FIG. 21.
Figure 24:
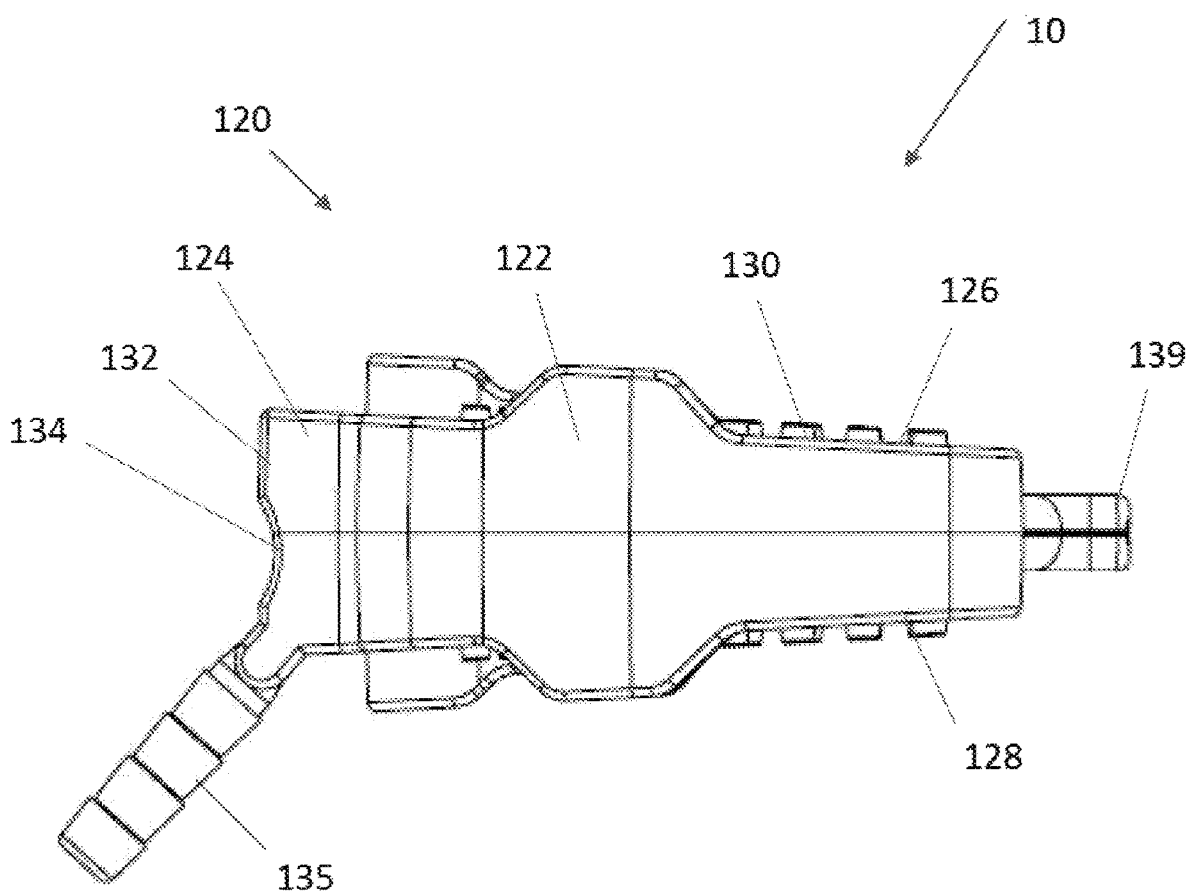
FIG. 24 is a side view of the mouth insertion apparatus of FIG. 21.
Figure 25:
FIG. 25 is a rear perspective view of a mouth insertion apparatus, according to certain embodiments of the present invention.
Figure 25:
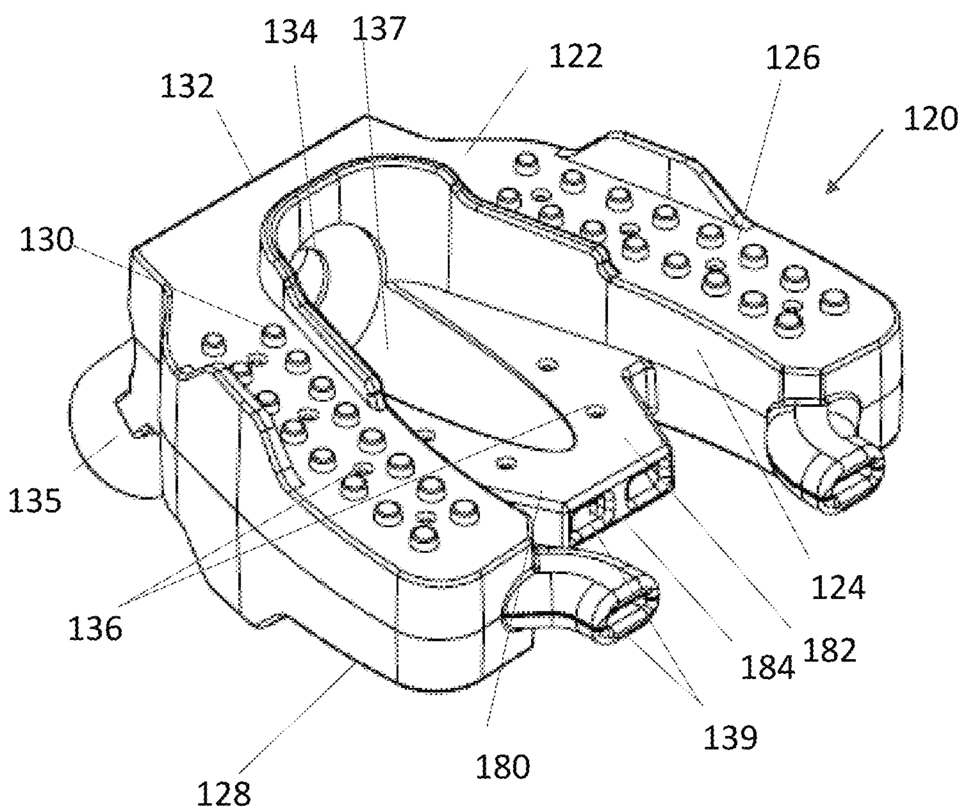
Figure 26:
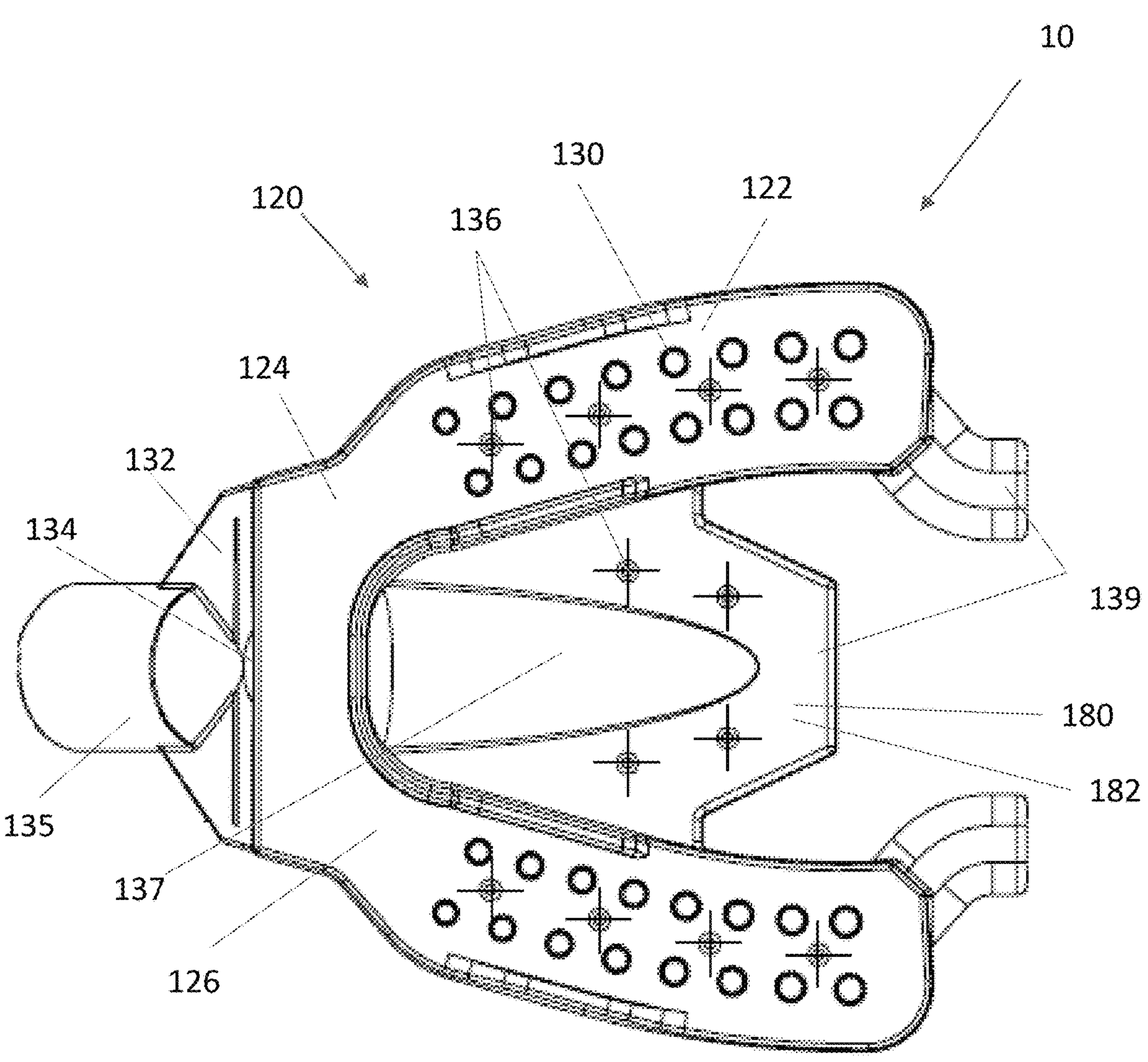
FIG. 26 is a top view of the mouth insertion apparatus of FIG. 25.
Figure 27:
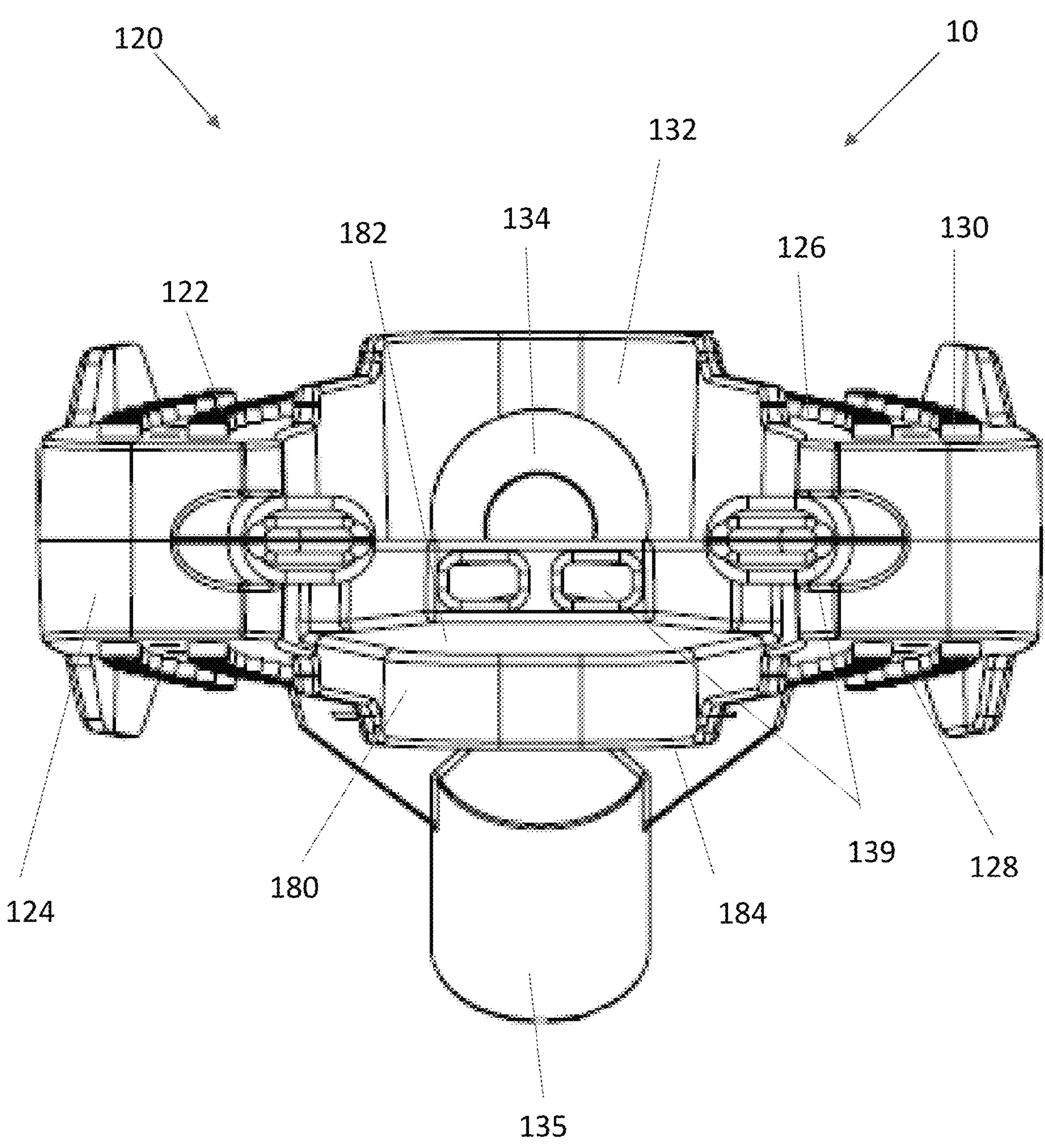
FIG. 27 is a rear view of the mouth insertion apparatus of FIG. 25.
Figure 28:
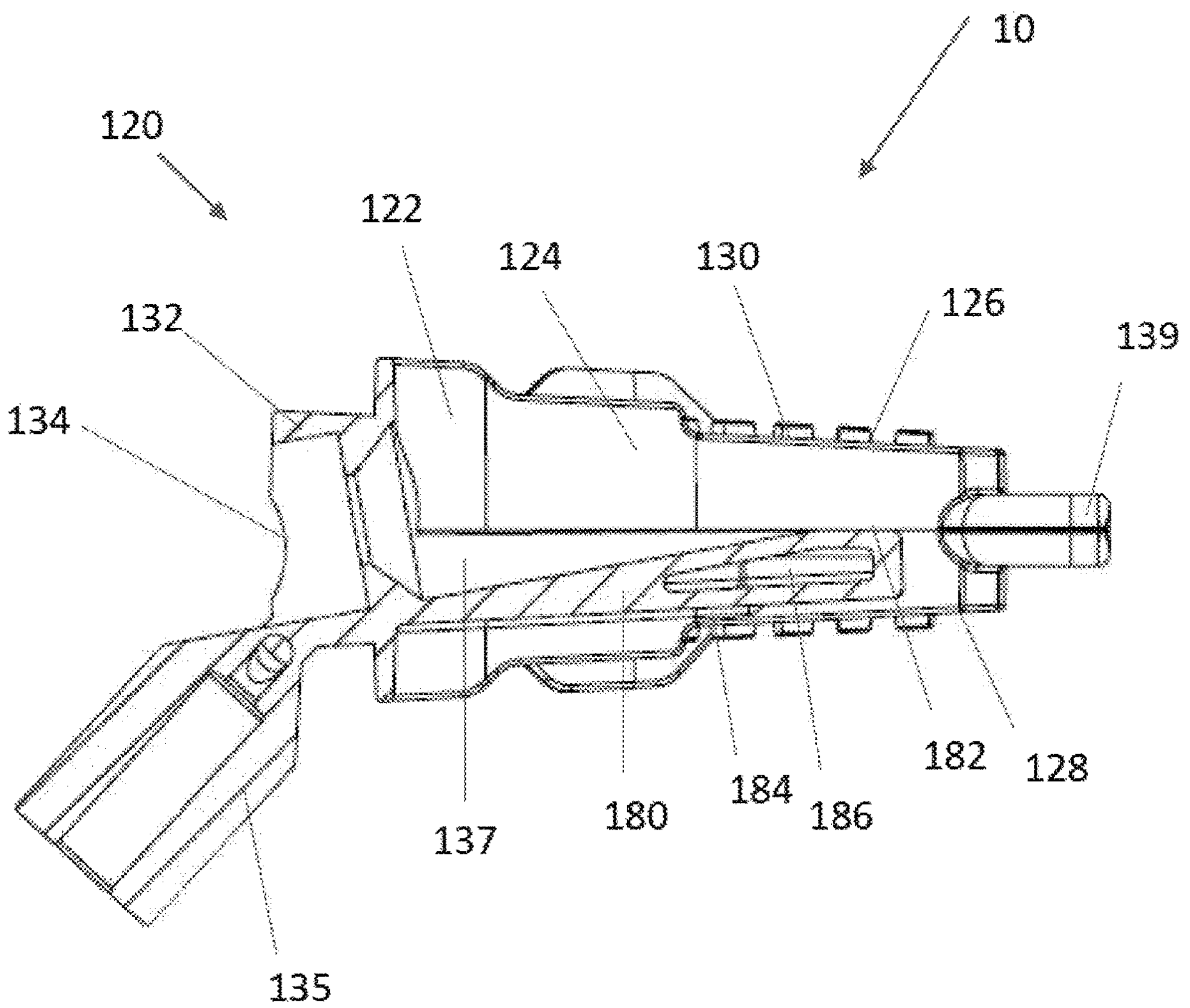
FIG. 28 is a side view of the mouth insertion apparatus of FIG. 25.
Figure 29:
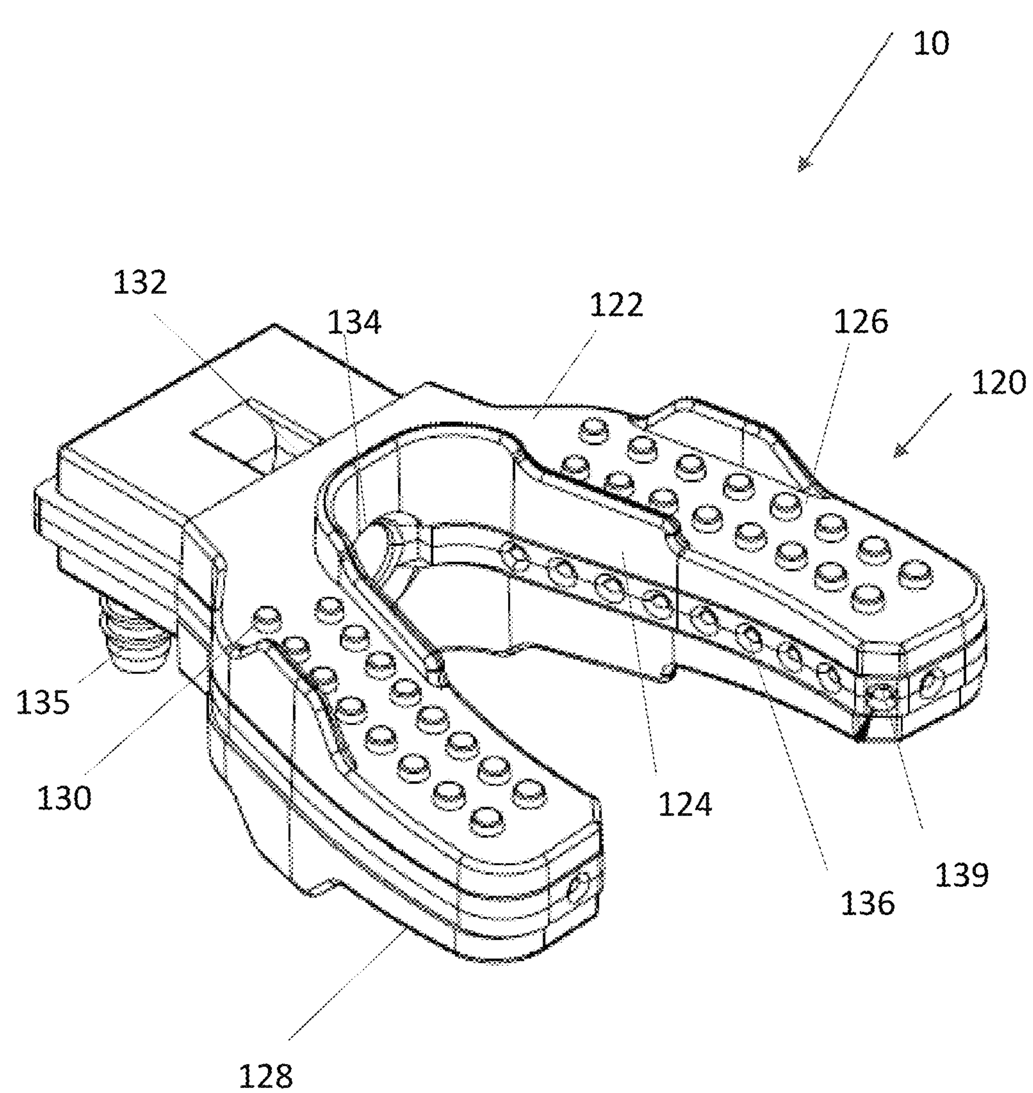
FIG. 29 is a rear perspective view of a mouth insertion apparatus, according to certain embodiments of the present invention.
Figure 30:
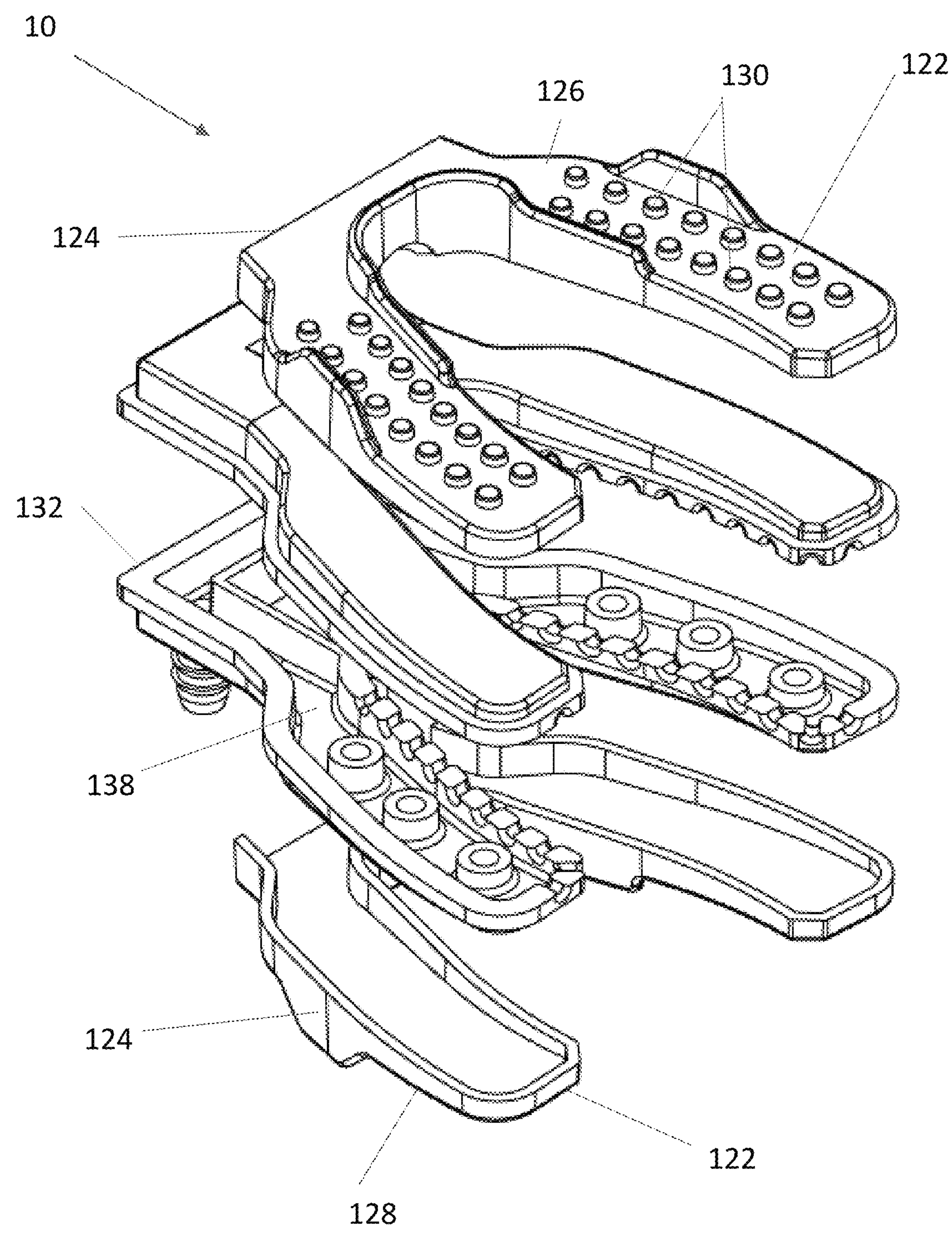
FIG. 30 is an exploded rear perspective view of the mouth insertion apparatus of FIG. 29.
Figure 31:
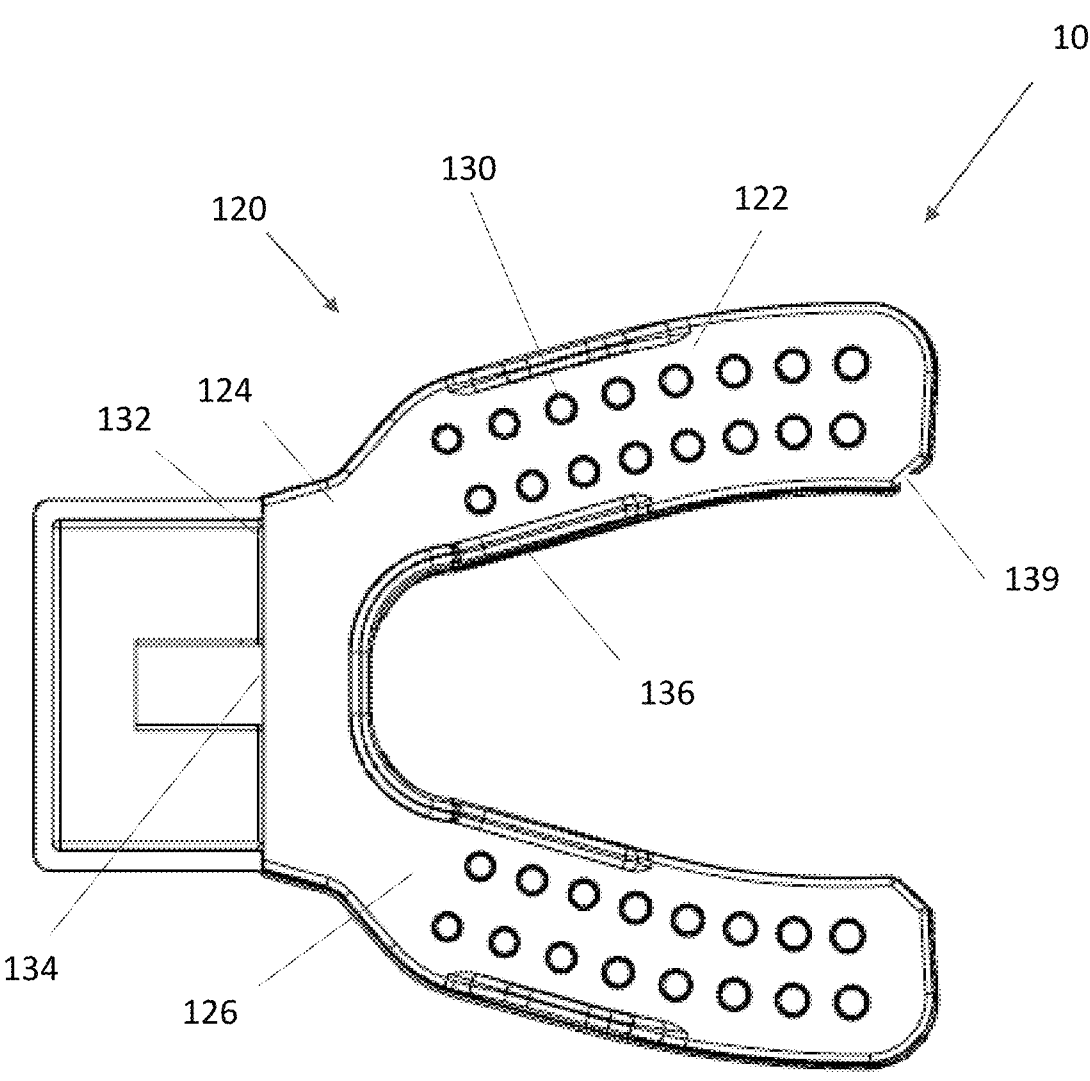
FIG. 31 is a top view of the mouth insertion apparatus of FIG. 29.
Figure 32:
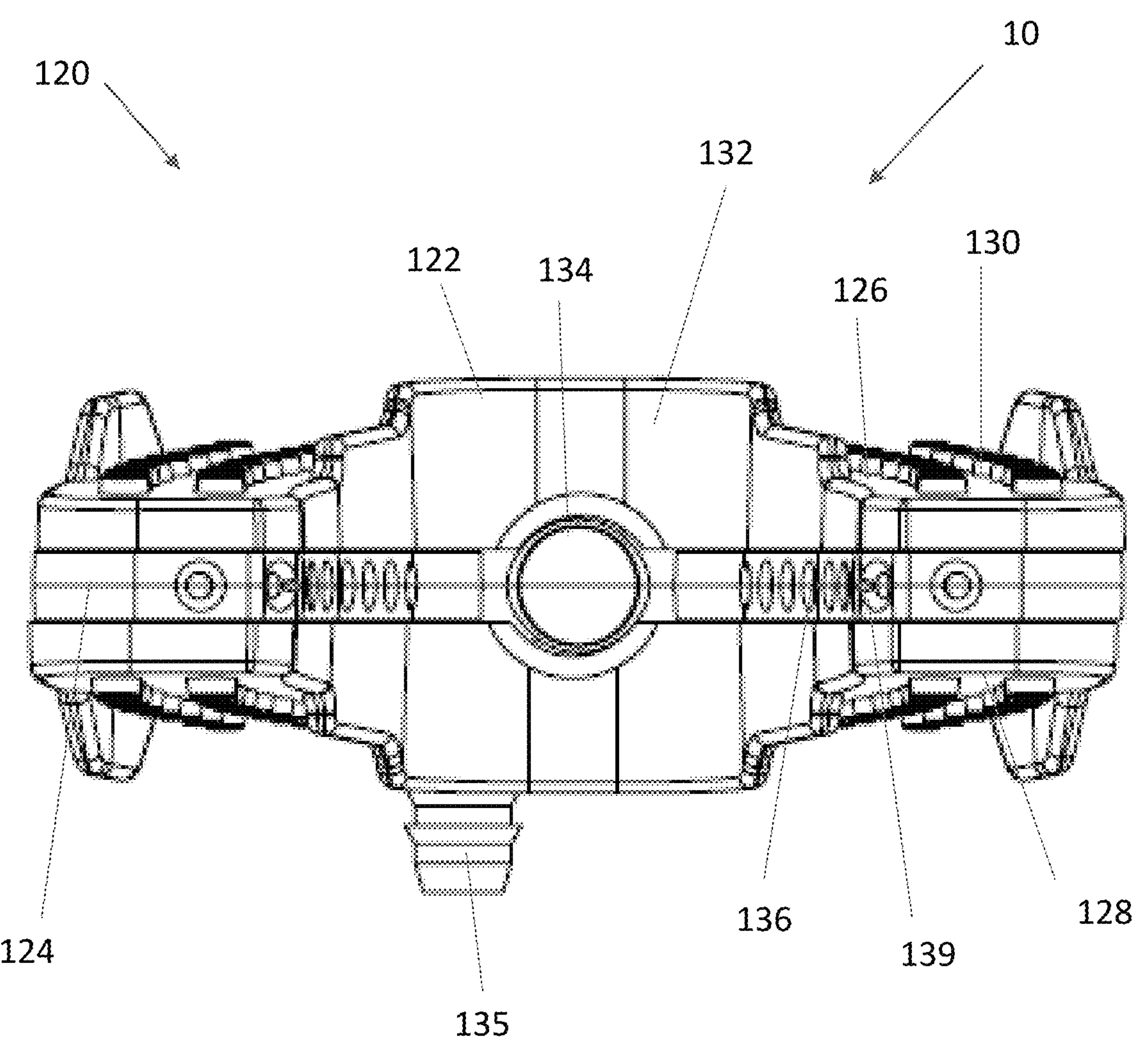
FIG. 32 is a rear view of the mouth insertion apparatus of FIG. 29.
Figure 33:
FIG. 33 is a side view of the mouth insertion apparatus of FIG. 29.
Figure 33:
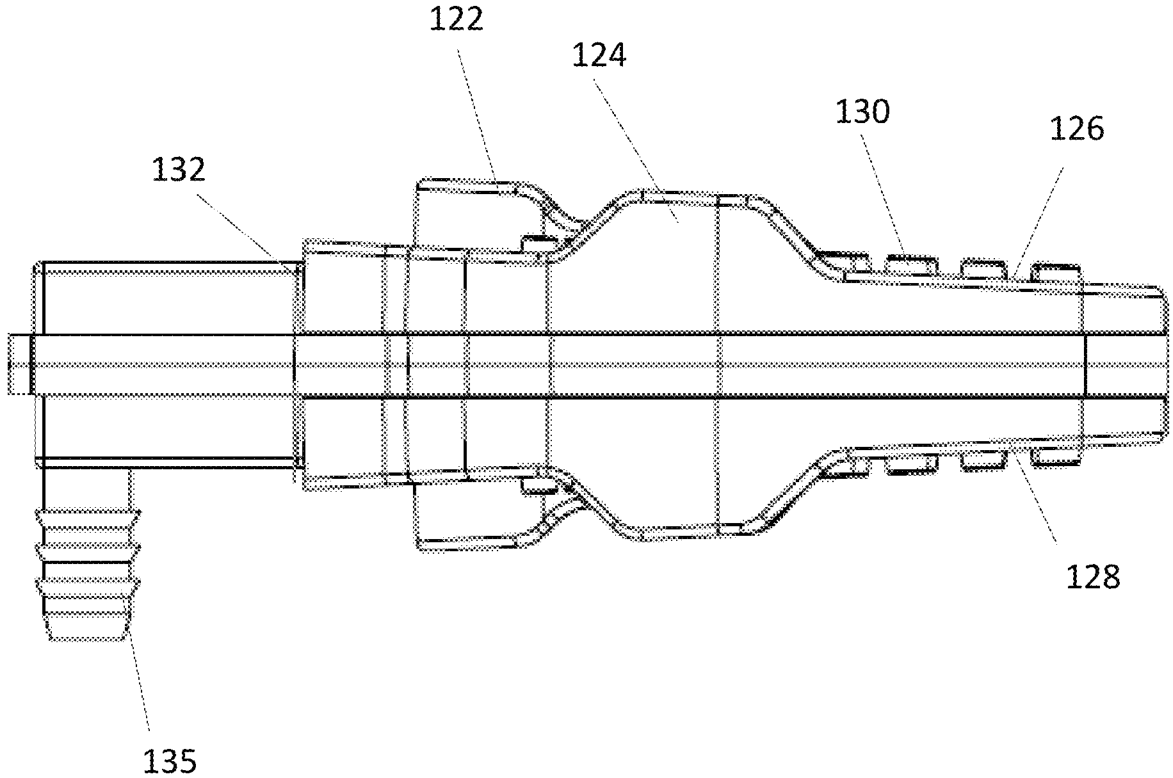
Figure 34:
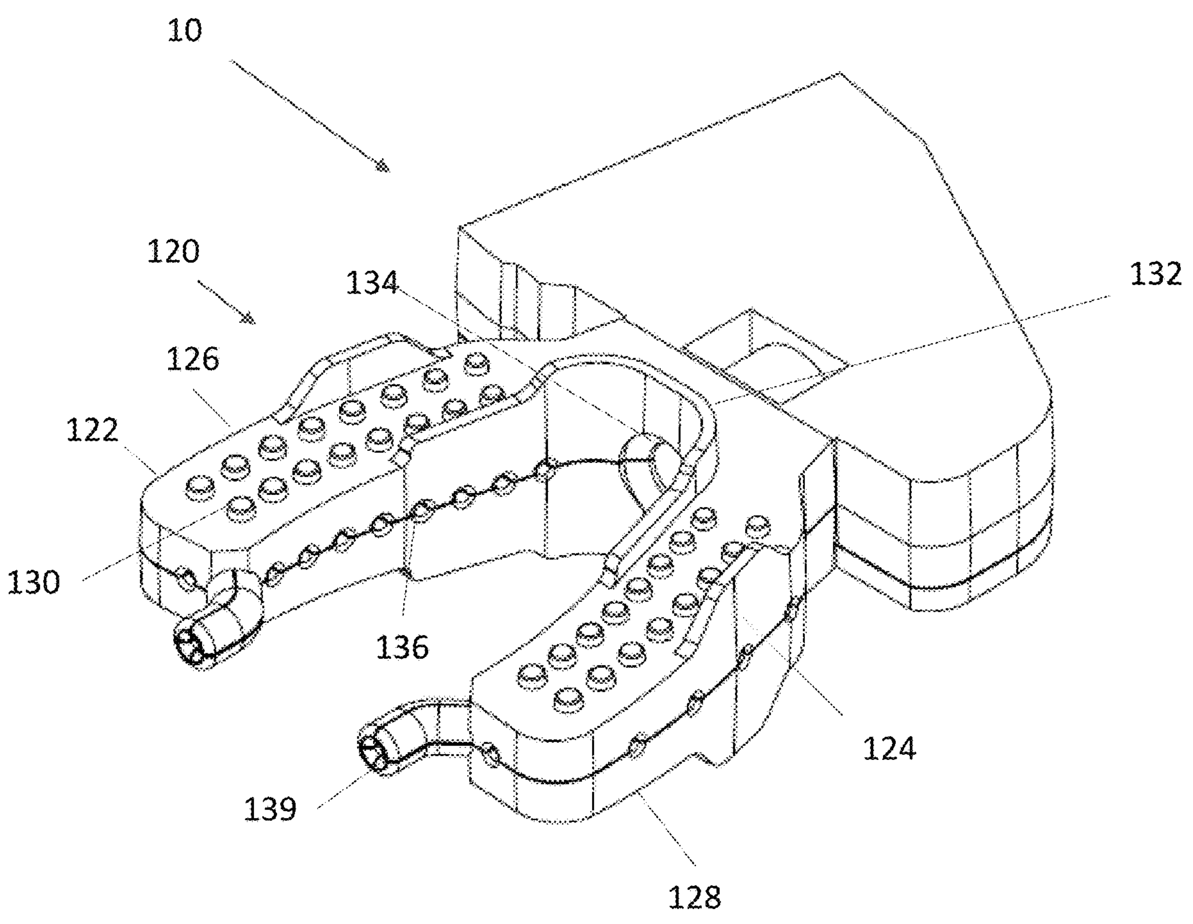
FIG. 34 is a rear perspective view of a mouth insertion apparatus, according to certain embodiments of the present invention.
Figure 35:
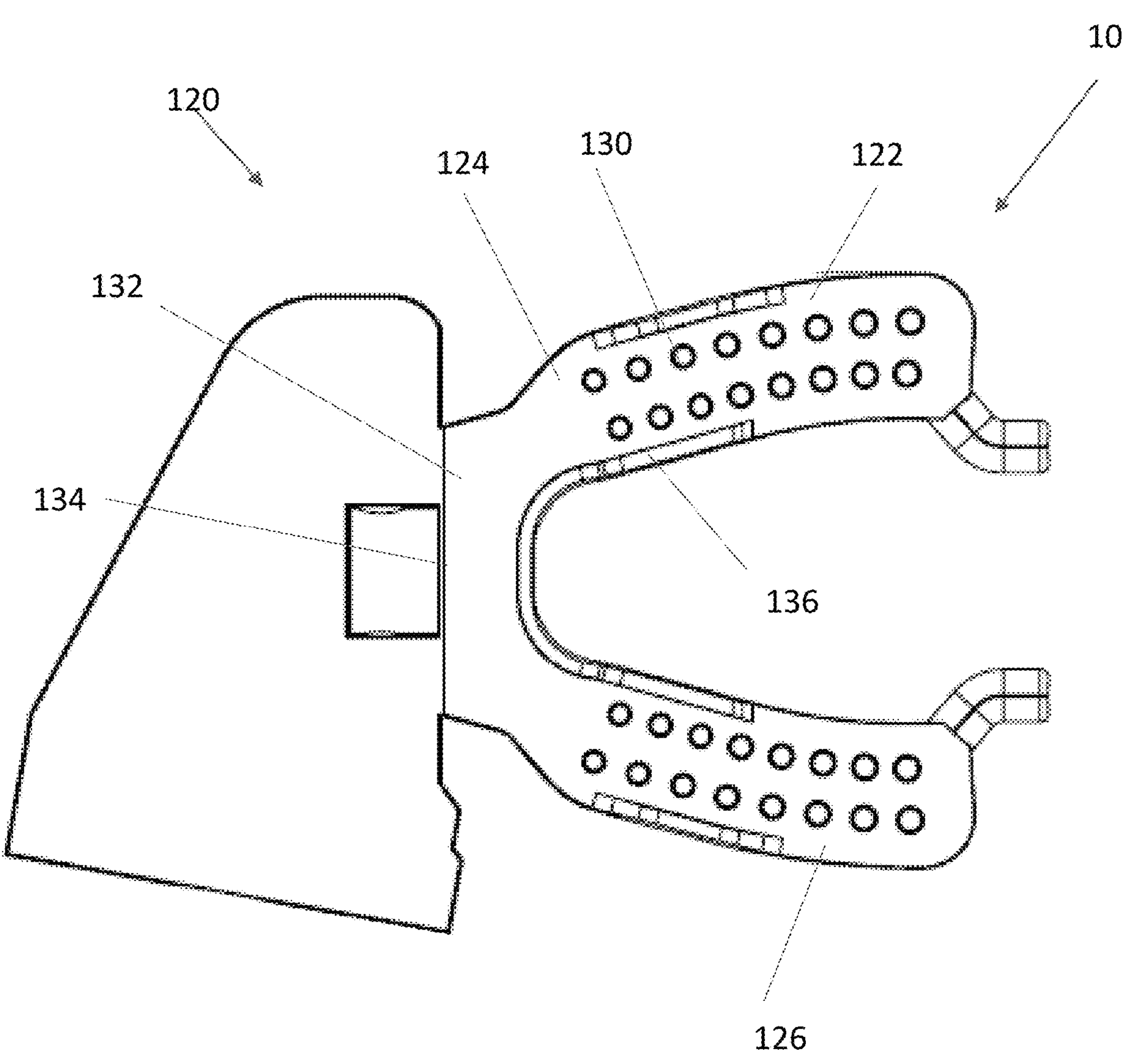
FIG. 35 is a top view of the mouth insertion apparatus of FIG. 34.
Figure 36:
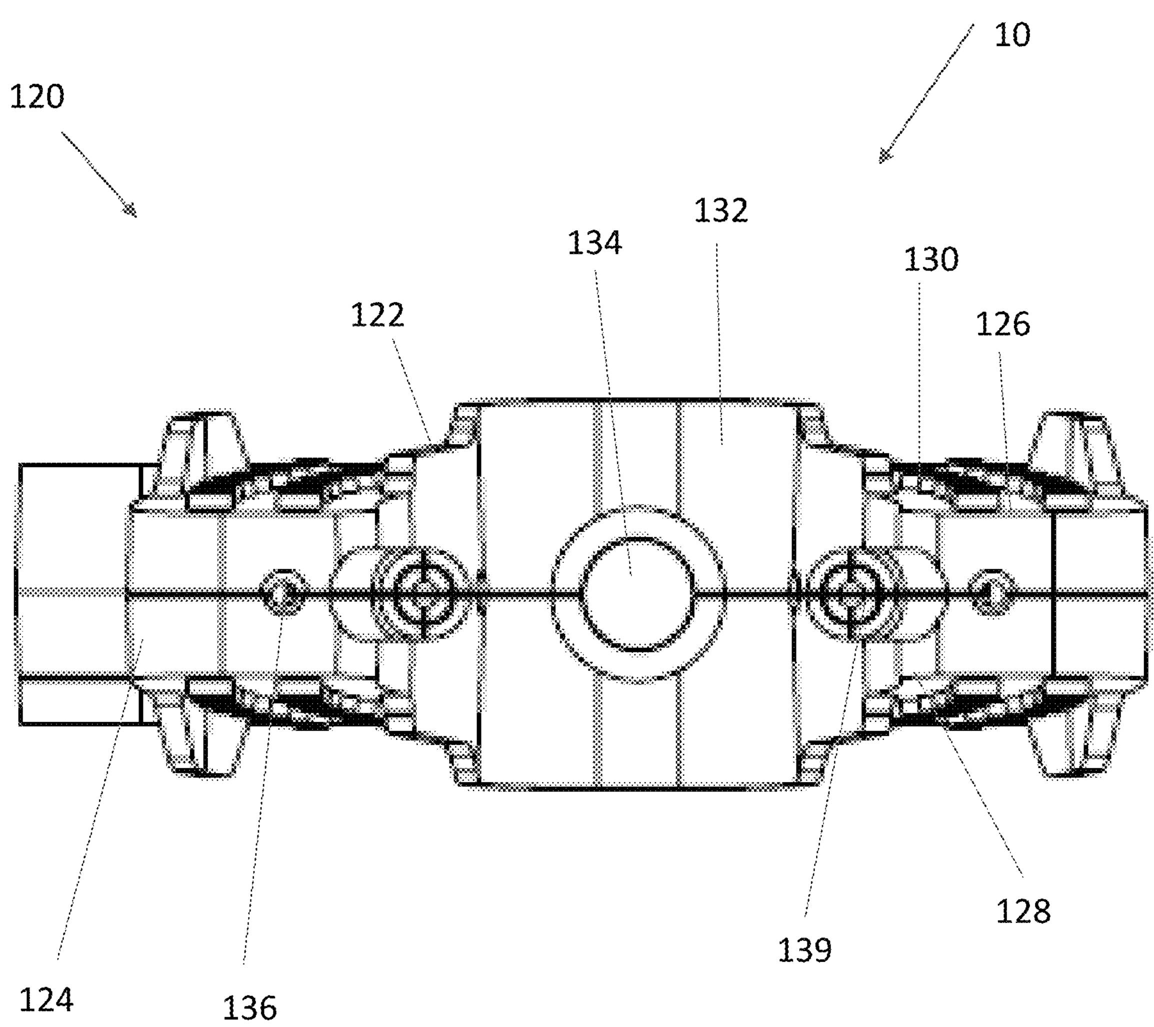
FIG. 36 is a rear view of the mouth insertion apparatus of FIG. 34.
Figure 37:
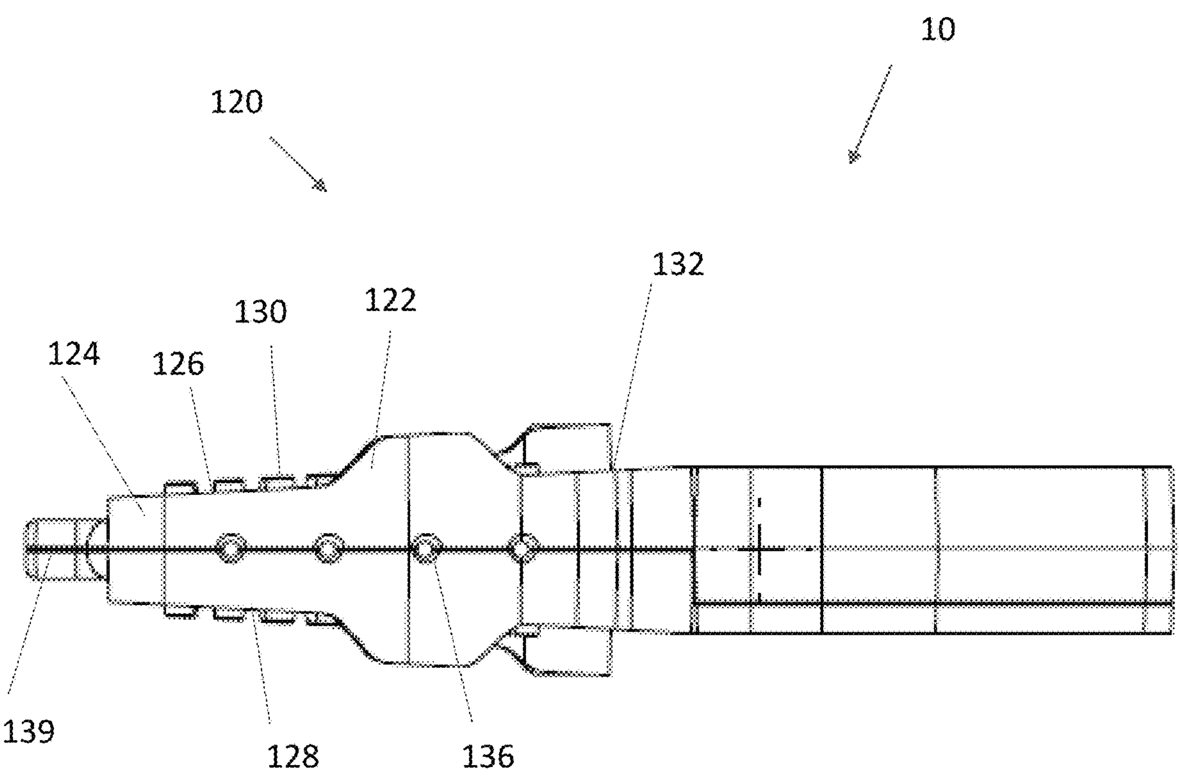
FIG. 37 is a side view of the mouth insertion apparatus of FIG. 34.
Figure 38:
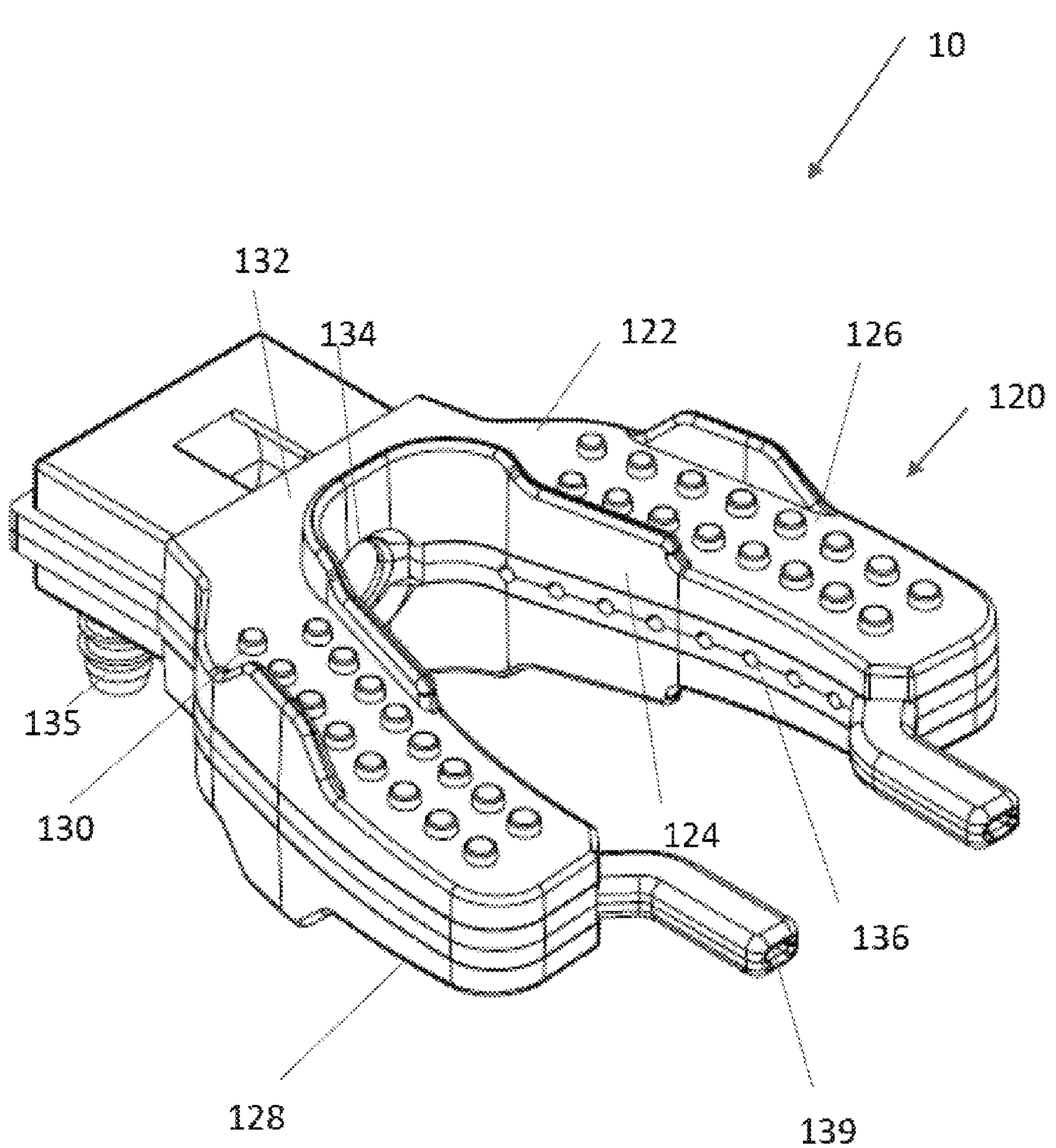
FIG. 38 is a rear perspective view of a mouth insertion apparatus, according to certain embodiments of the present invention.
Figure 39:
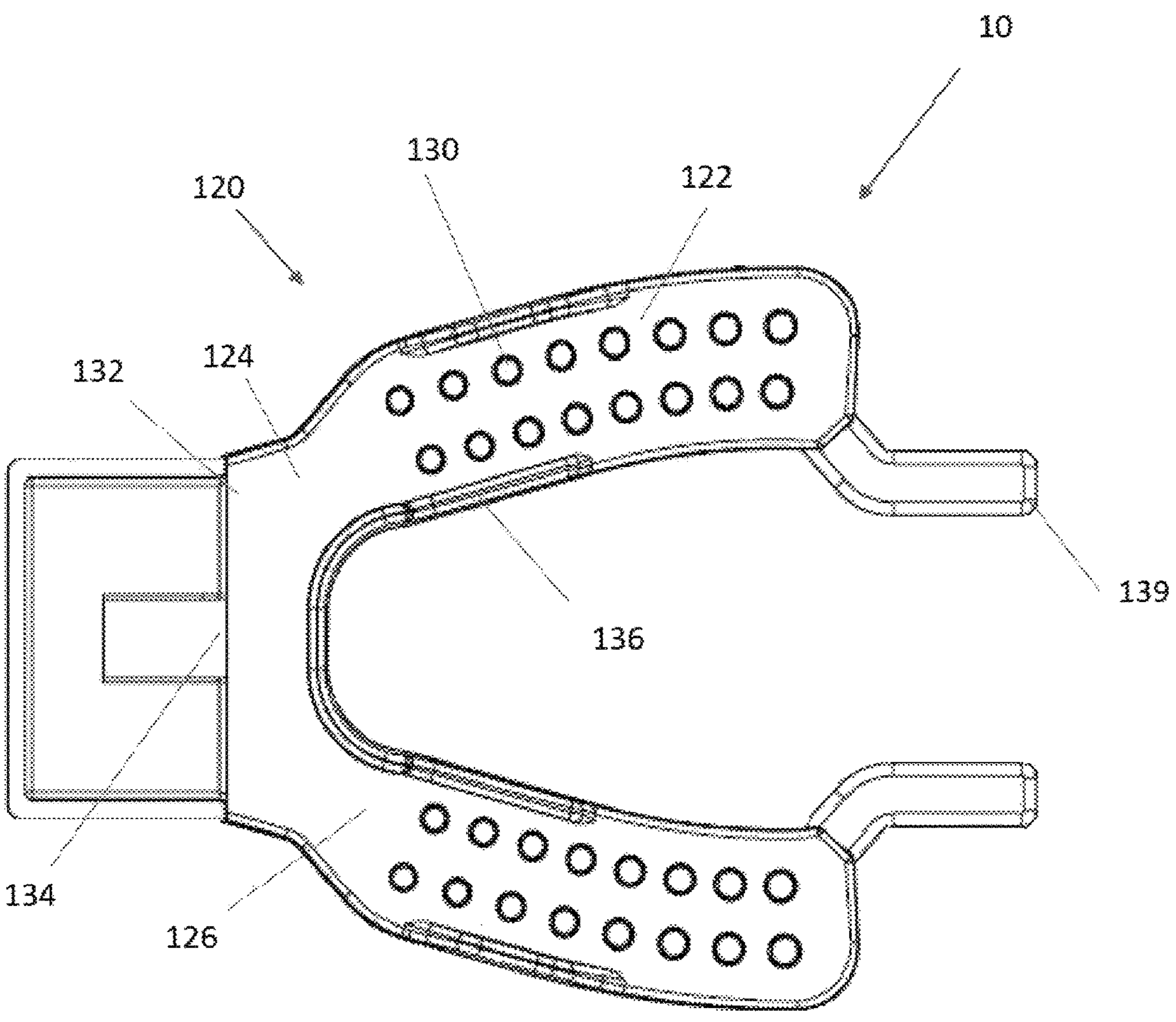
FIG. 39 is a top view of the mouth insertion apparatus of FIG. 38.
Figure 40:
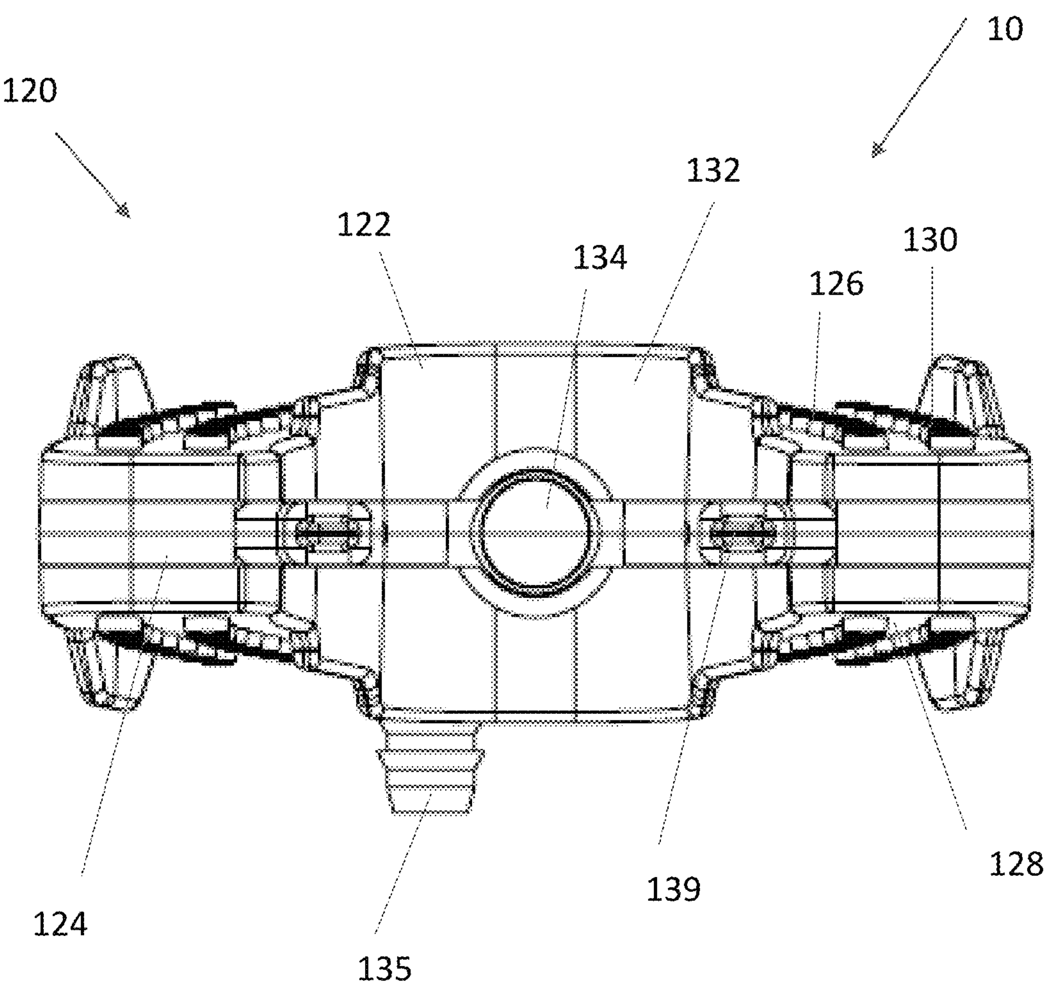
FIG. 40 is a rear view of the mouth insertion apparatus of FIG. 38.
Figure 41:
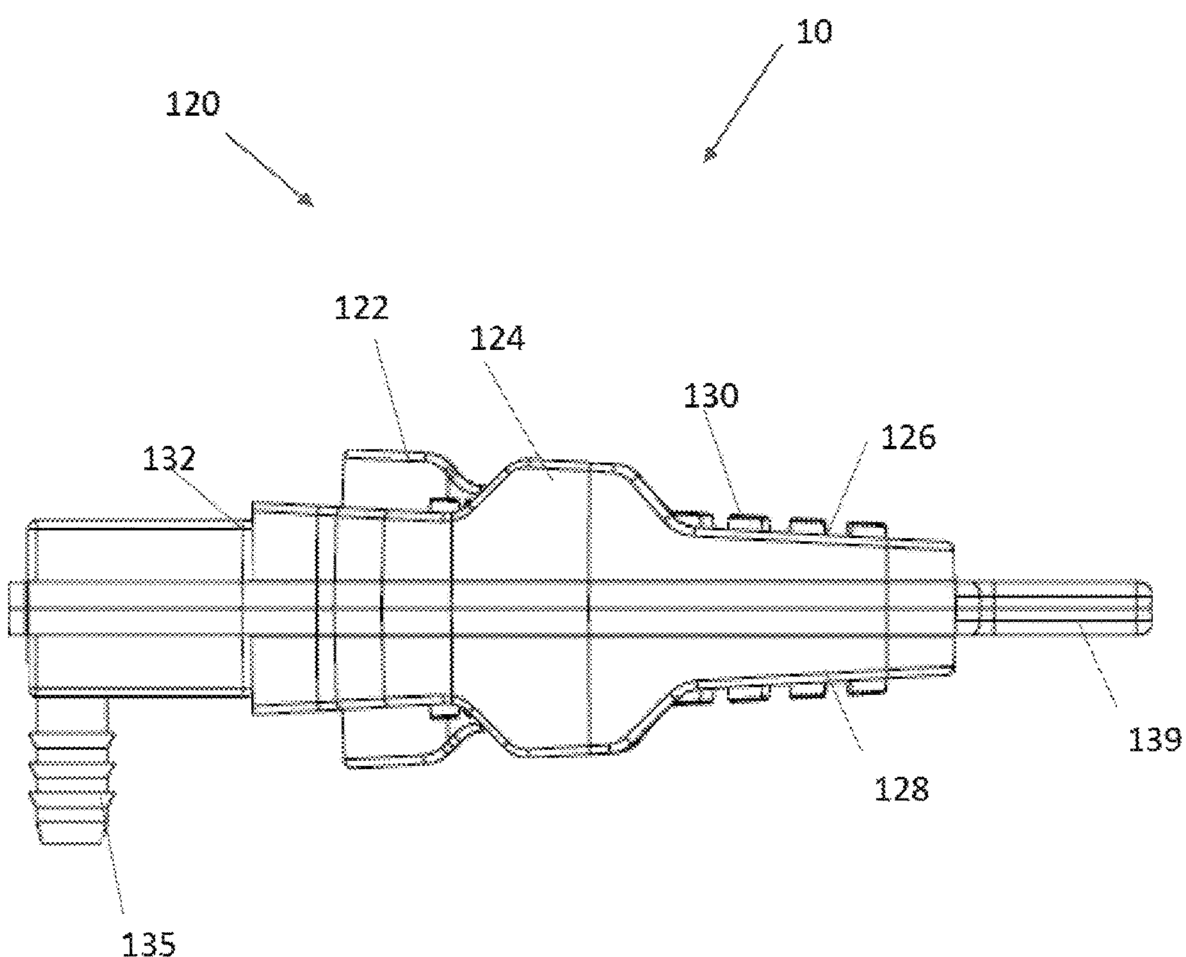
FIG. 41 is a side view of the mouth insertion apparatus of FIG. 38.
Figure 42:
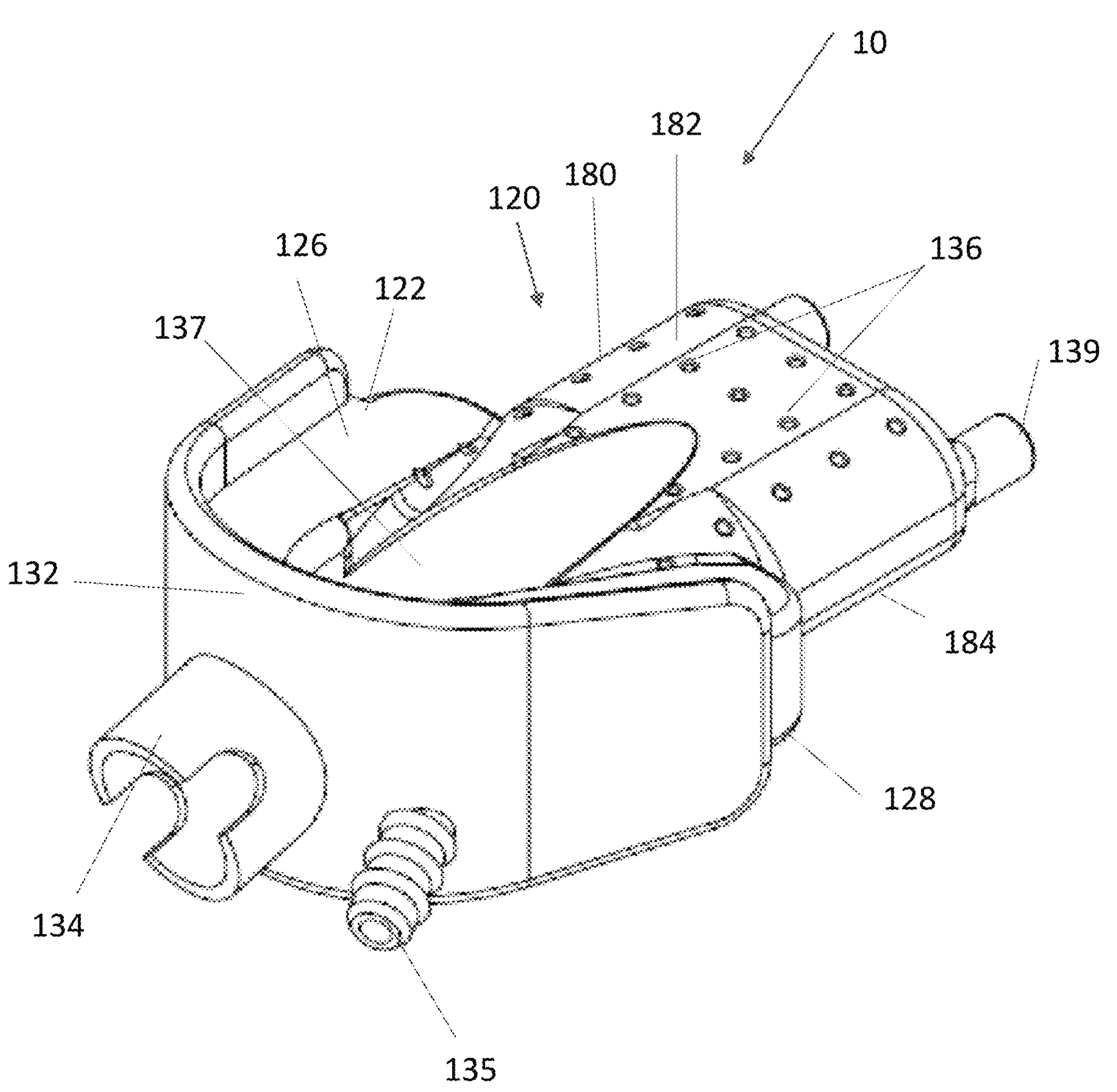
FIG. 42 is a front perspective view of a mouth insertion apparatus, according to certain embodiments of the present invention.
Figure 43:
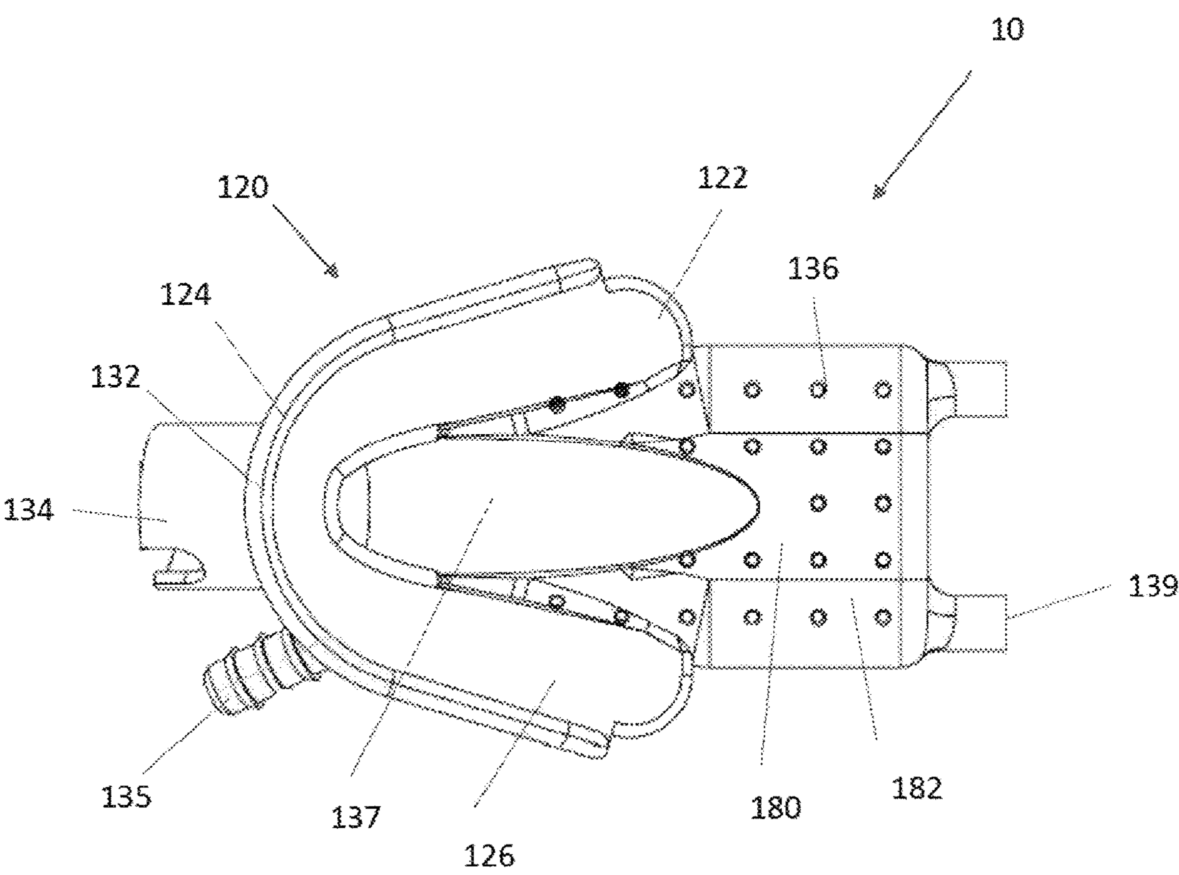
FIG. 43 is a top view of the mouth insertion apparatus of FIG. 42.
Figure 44:
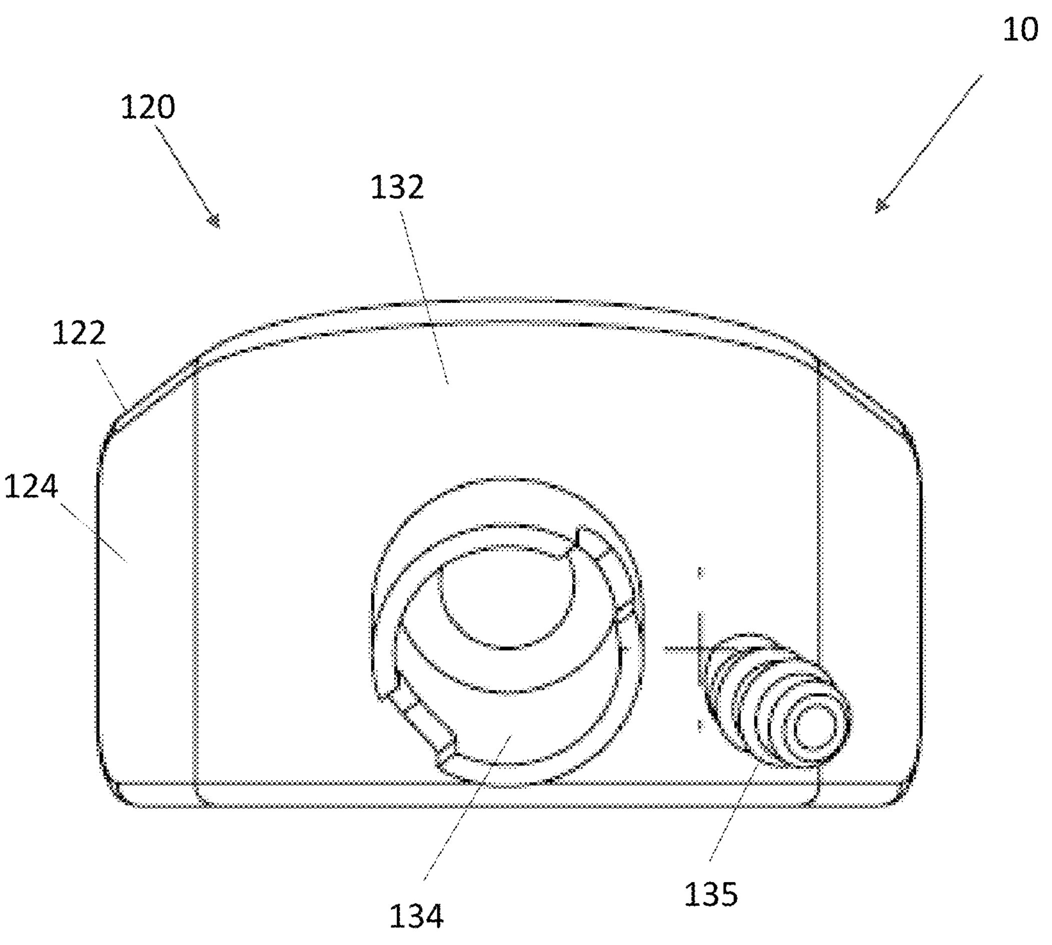
FIG. 44 is a front view of the mouth insertion apparatus of FIG. 42.
Figure 45:
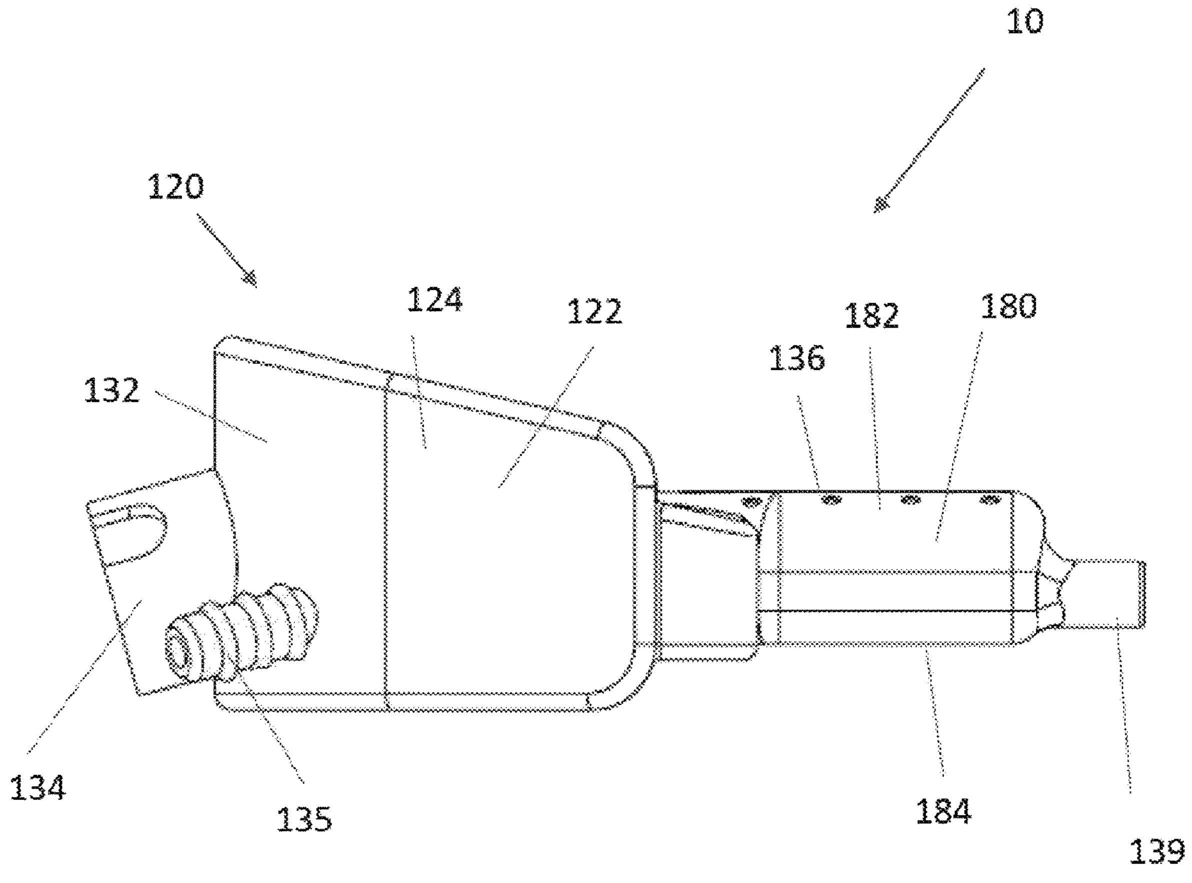
FIG. 45 is a side view of the mouth insertion apparatus of FIG. 42.
Figure 46:
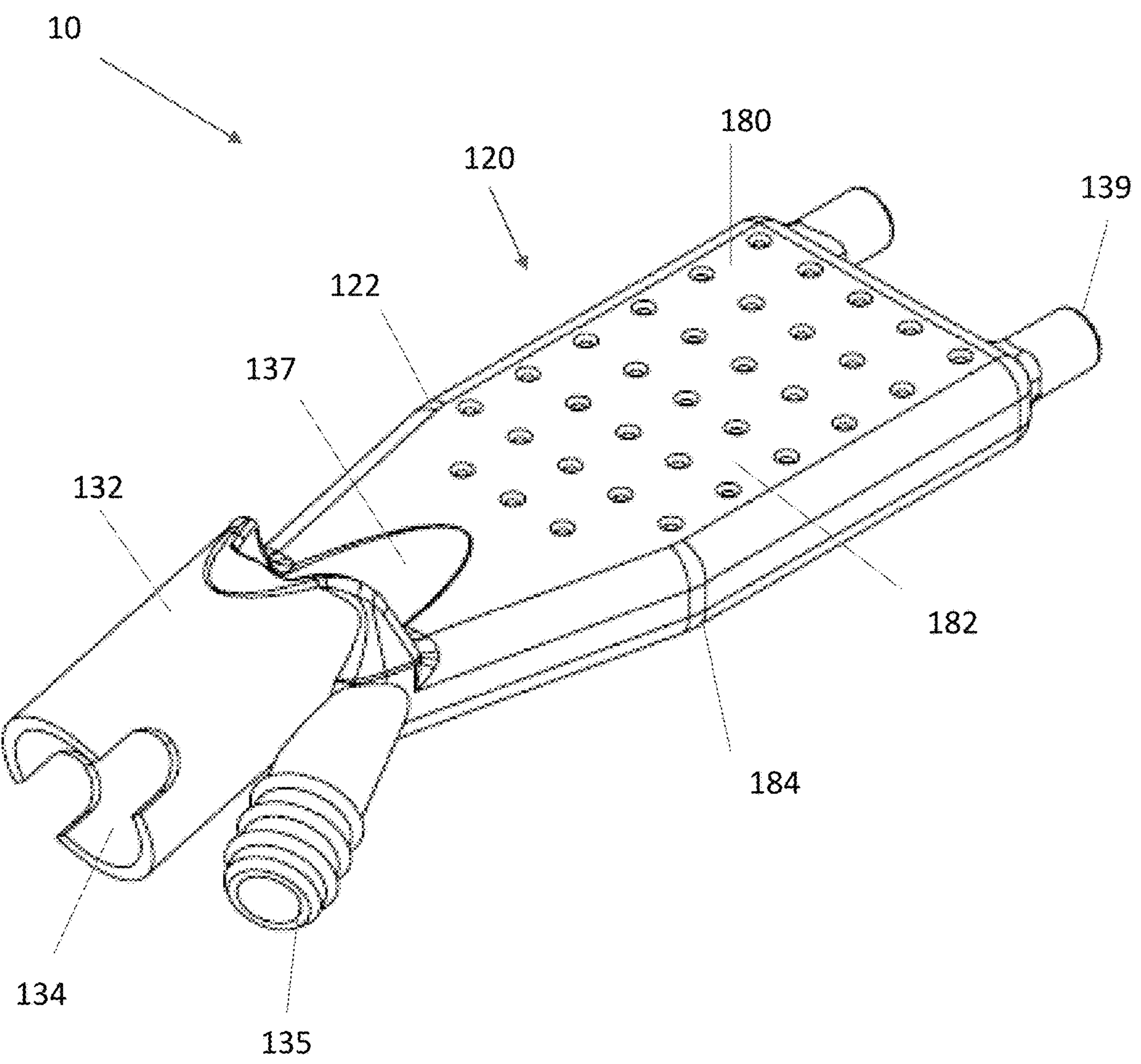
FIG. 46 is a front perspective view of a mouth insertion apparatus, according to certain embodiments of the present invention.
Figure 47:
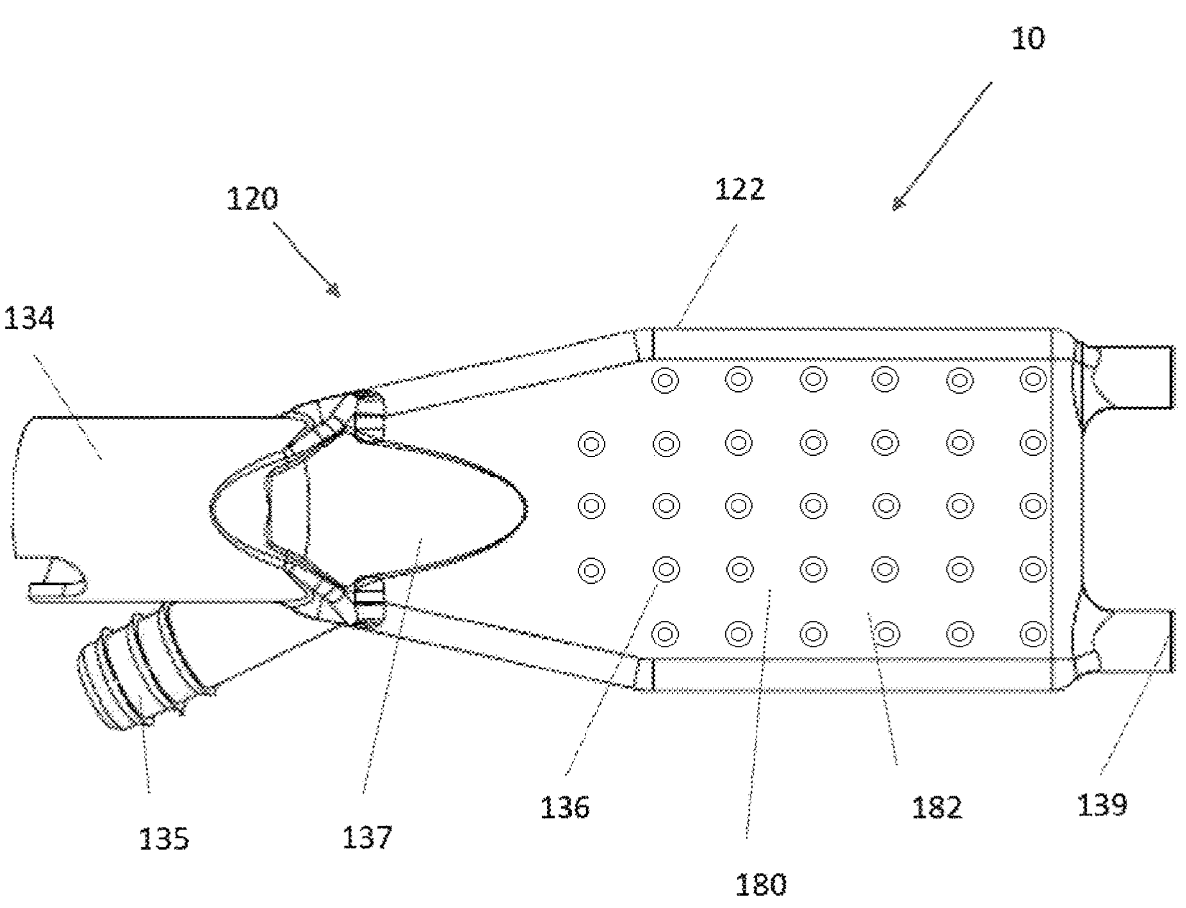
FIG. 47 is a top view of the mouth insertion apparatus of FIG. 42.
Figure 48:
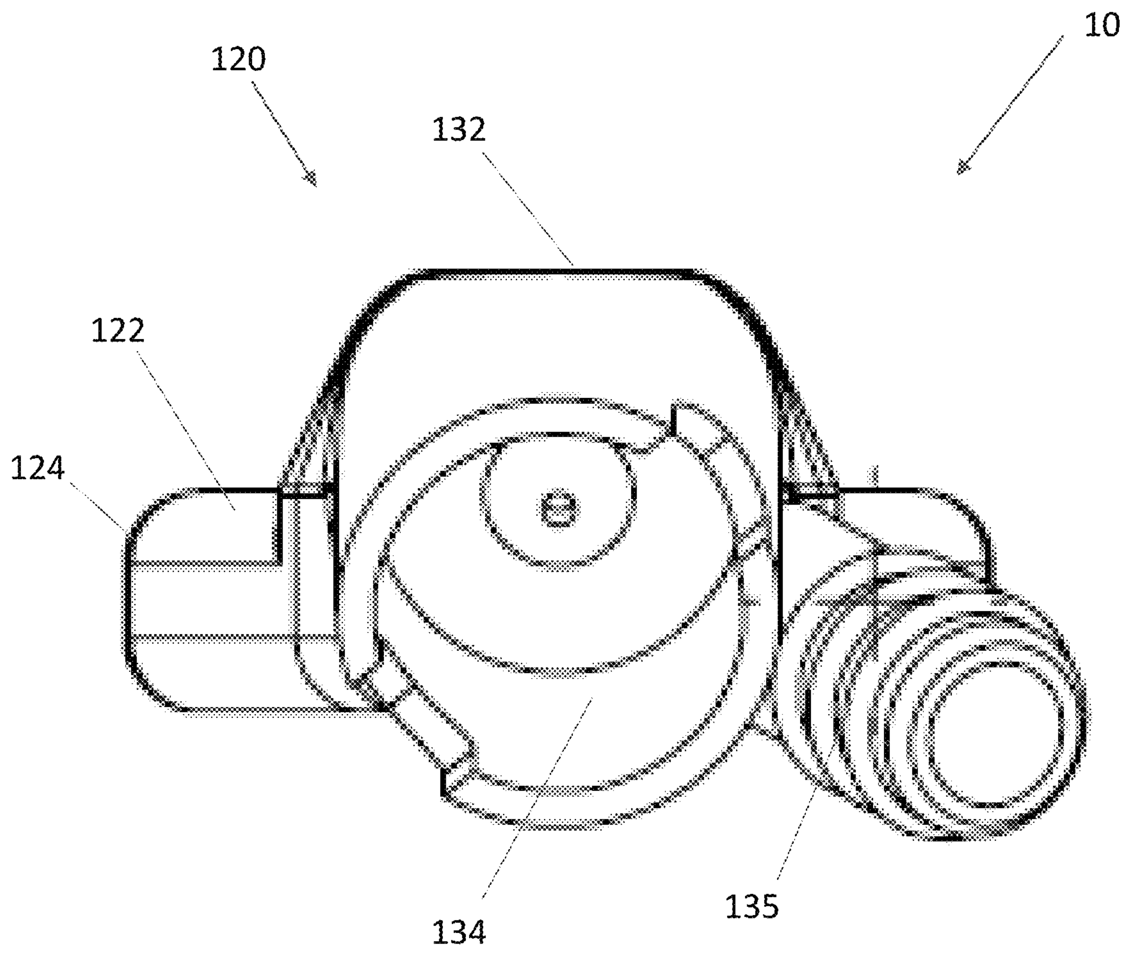
FIG. 48 is a front view of the mouth insertion apparatus of FIG. 42.
Figure 49:
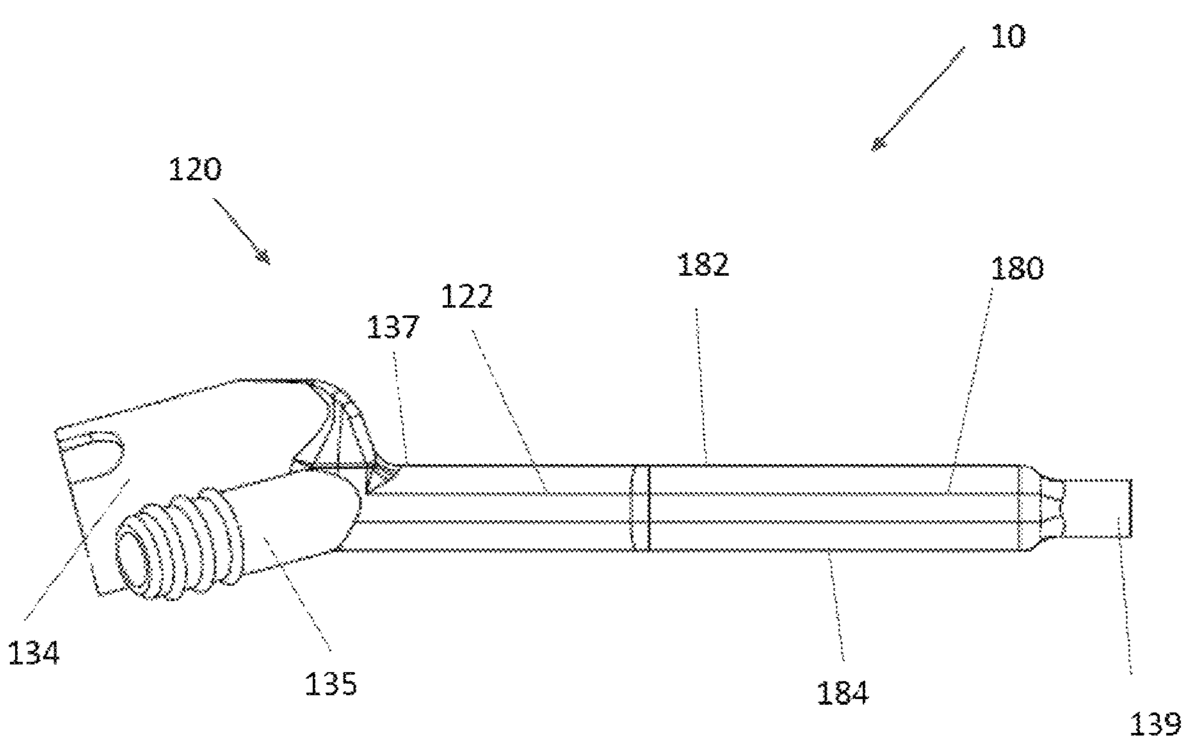
FIG. 49 is a side view of the mouth insertion apparatus of FIG. 42.
Figure 50:
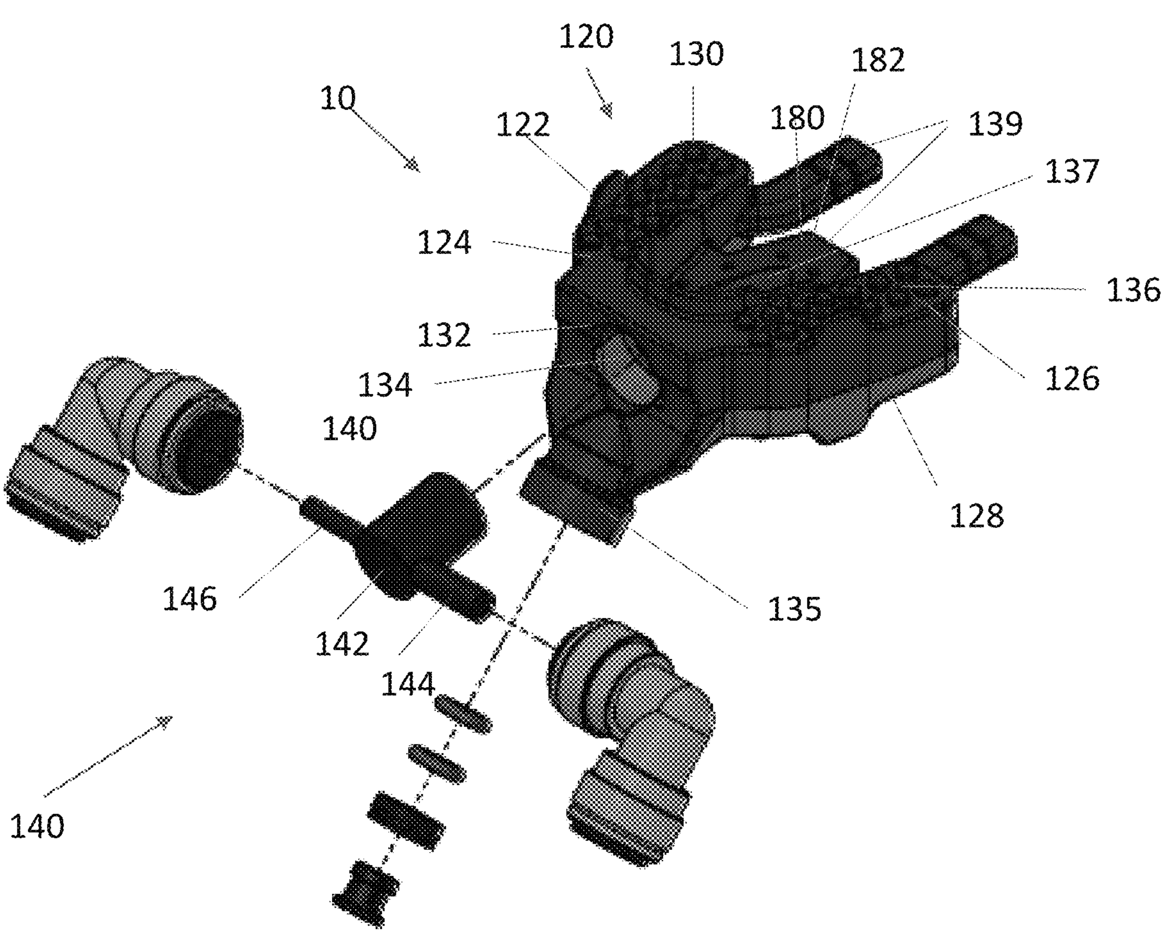
FIG. 50 is an exploded front perspective view of an oral phlegm extraction system comprising a mouth insertion apparatus and portions of a misting apparatus, according to certain embodiments of the present invention.
Figure 51:
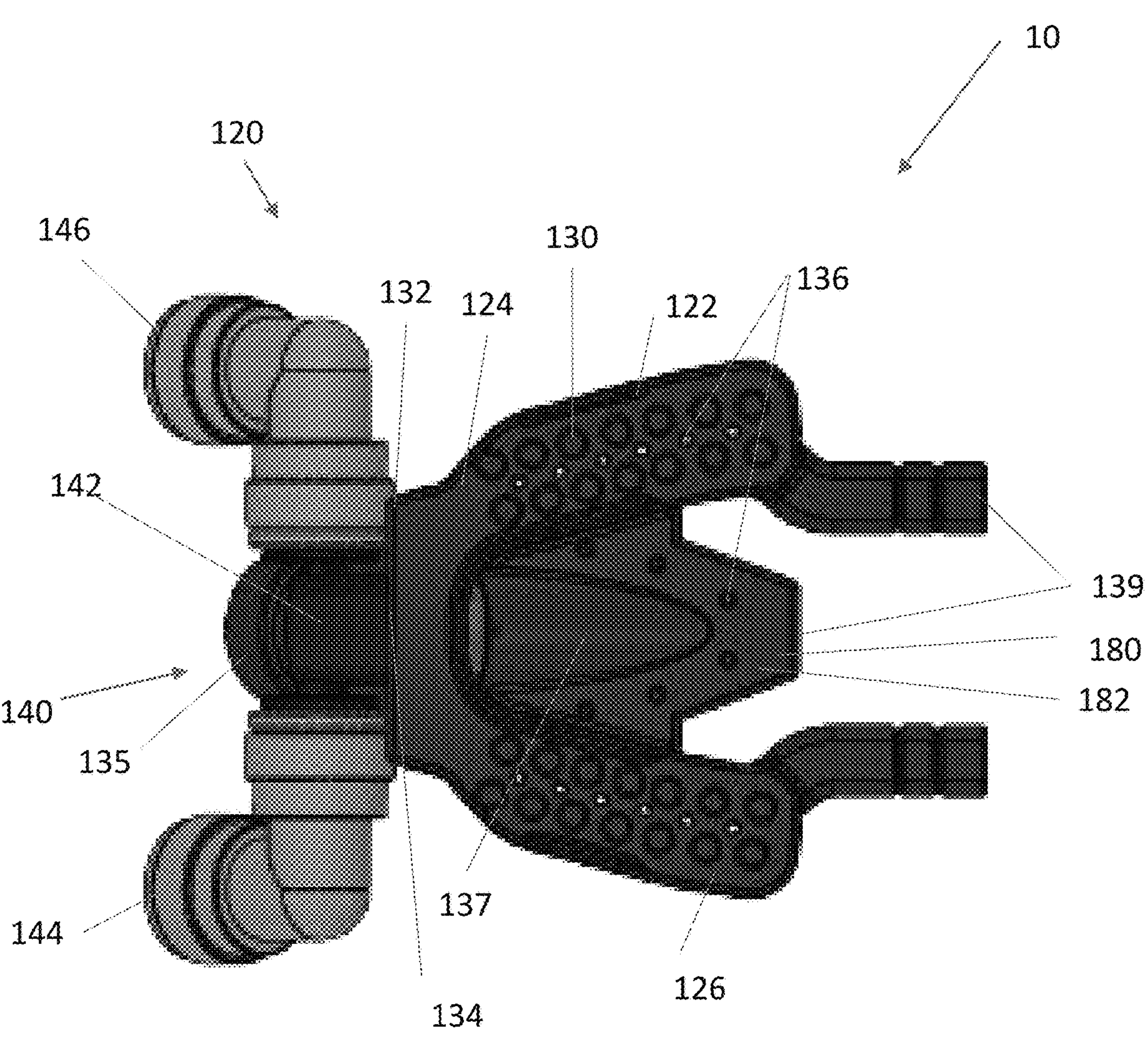
FIG. 51 is a top view of the oral phlegm extraction system of FIG. 50.
Figure 52:
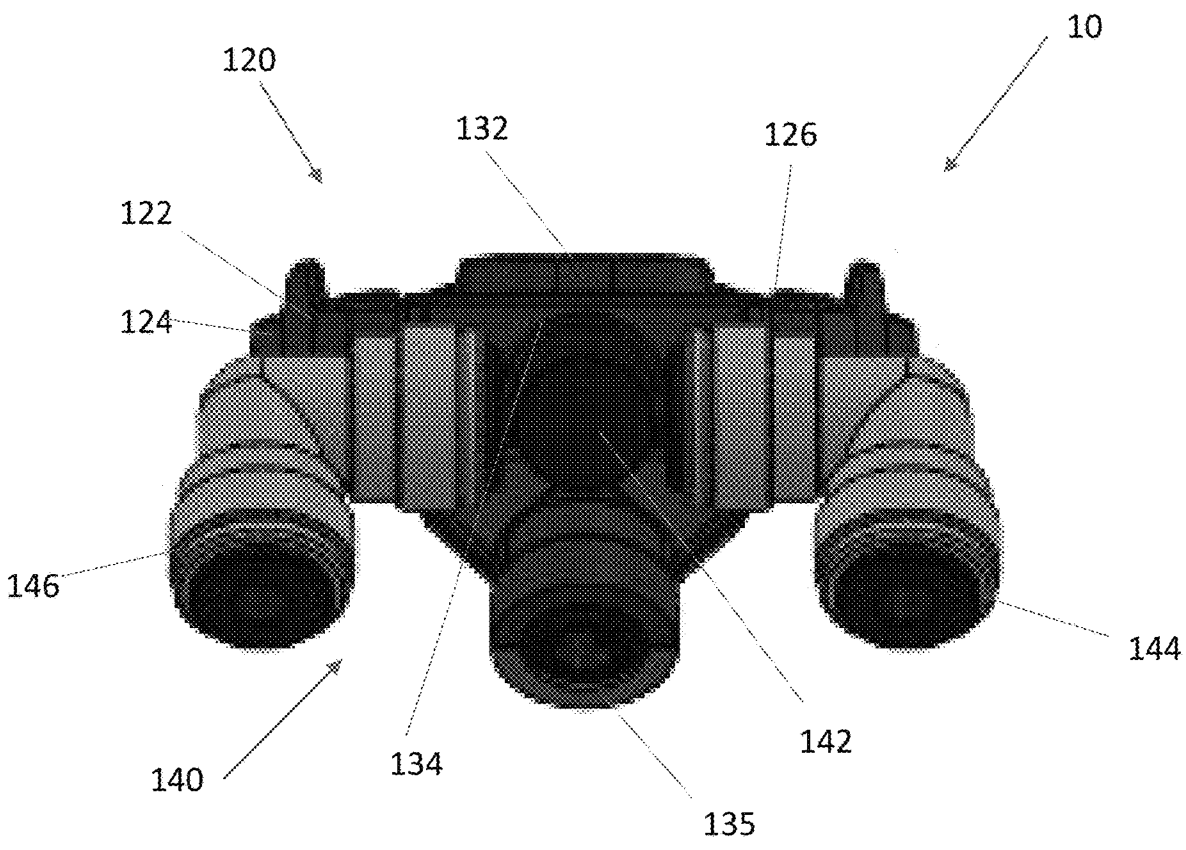
FIG. 52 is a front view of the oral phlegm extraction system of FIG. 50.
Figure 53:
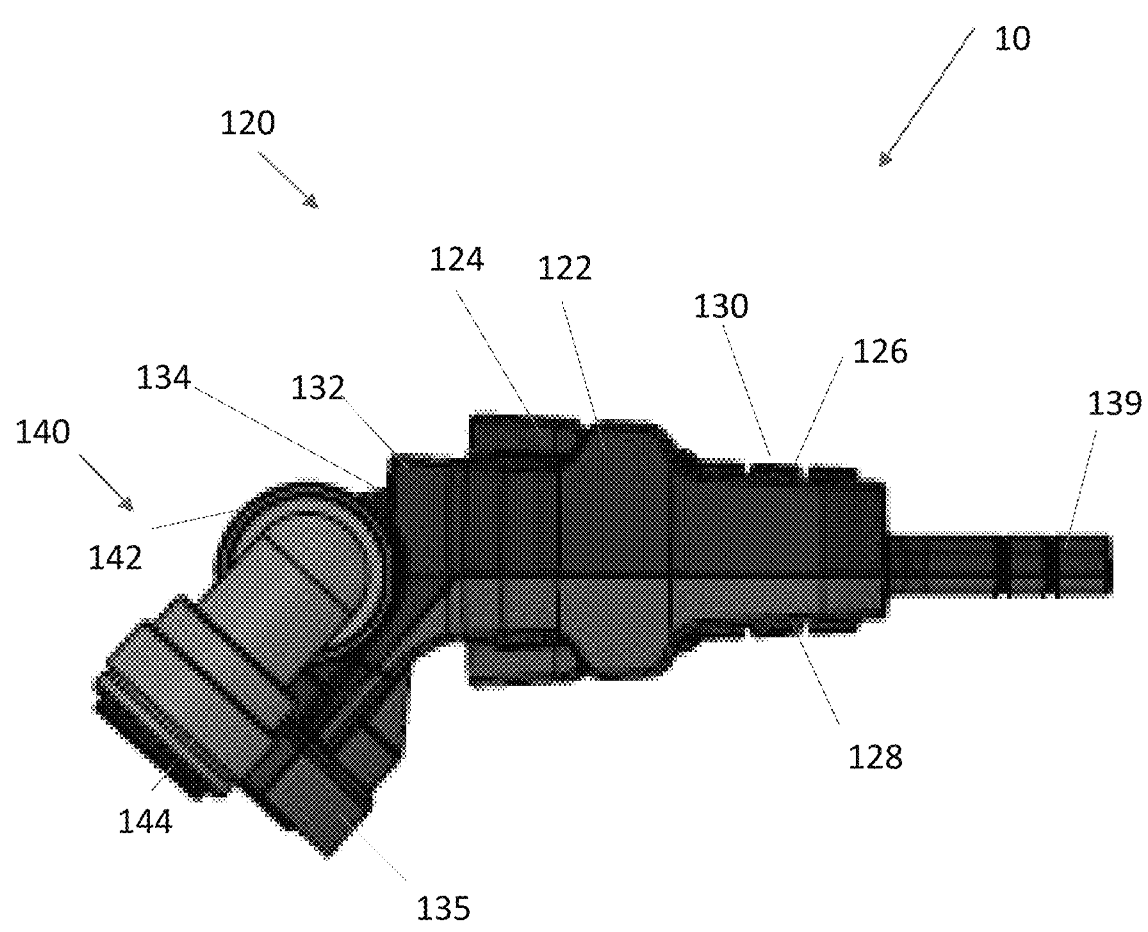
FIG. 53 is a side view of the oral phlegm extraction system of FIG. 50.
Figure 54:
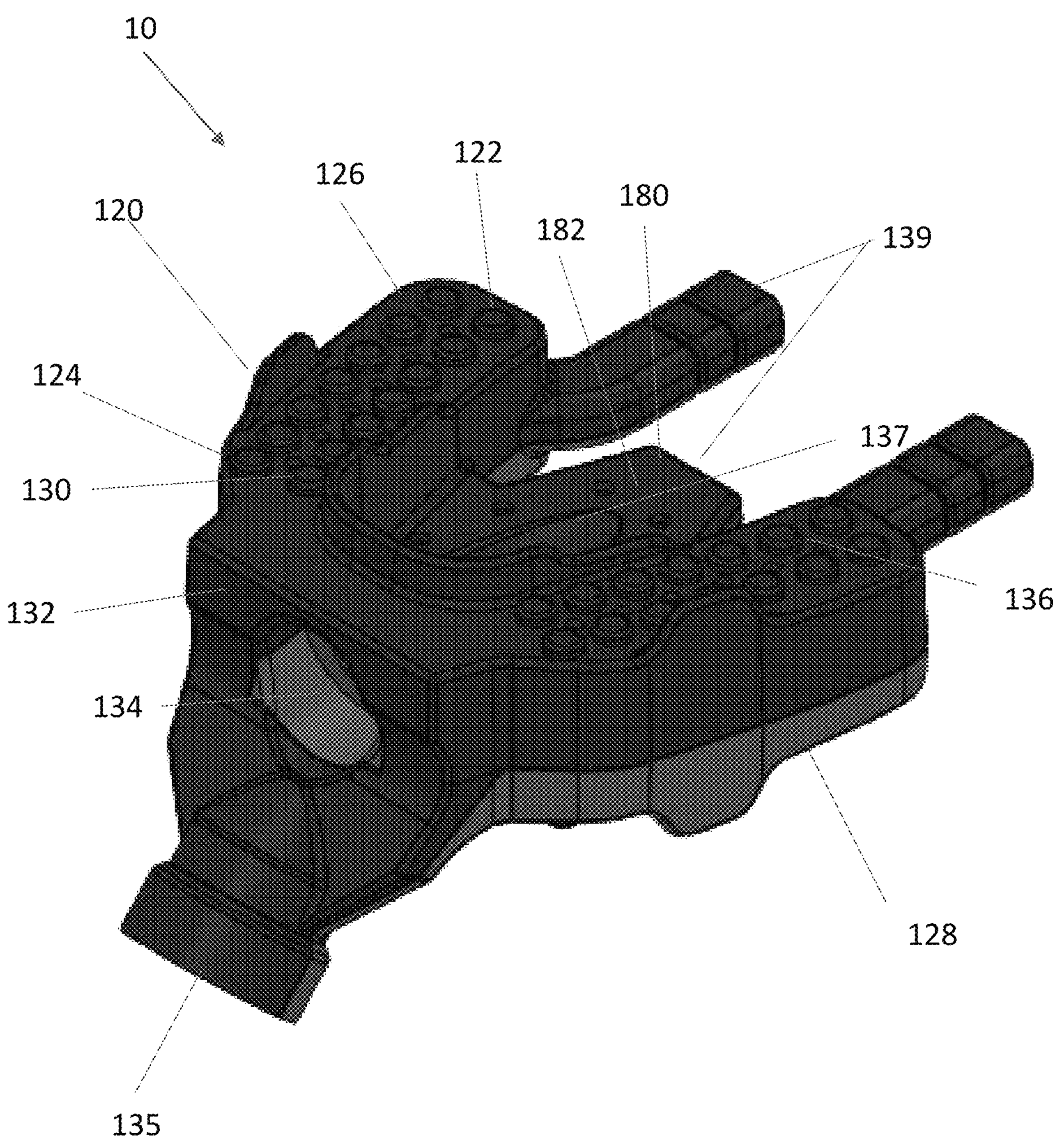
FIG. 54 is a front perspective view of the oral phlegm extraction system of FIG. 50 with the portions of the misting apparatus removed.
Figure 55:
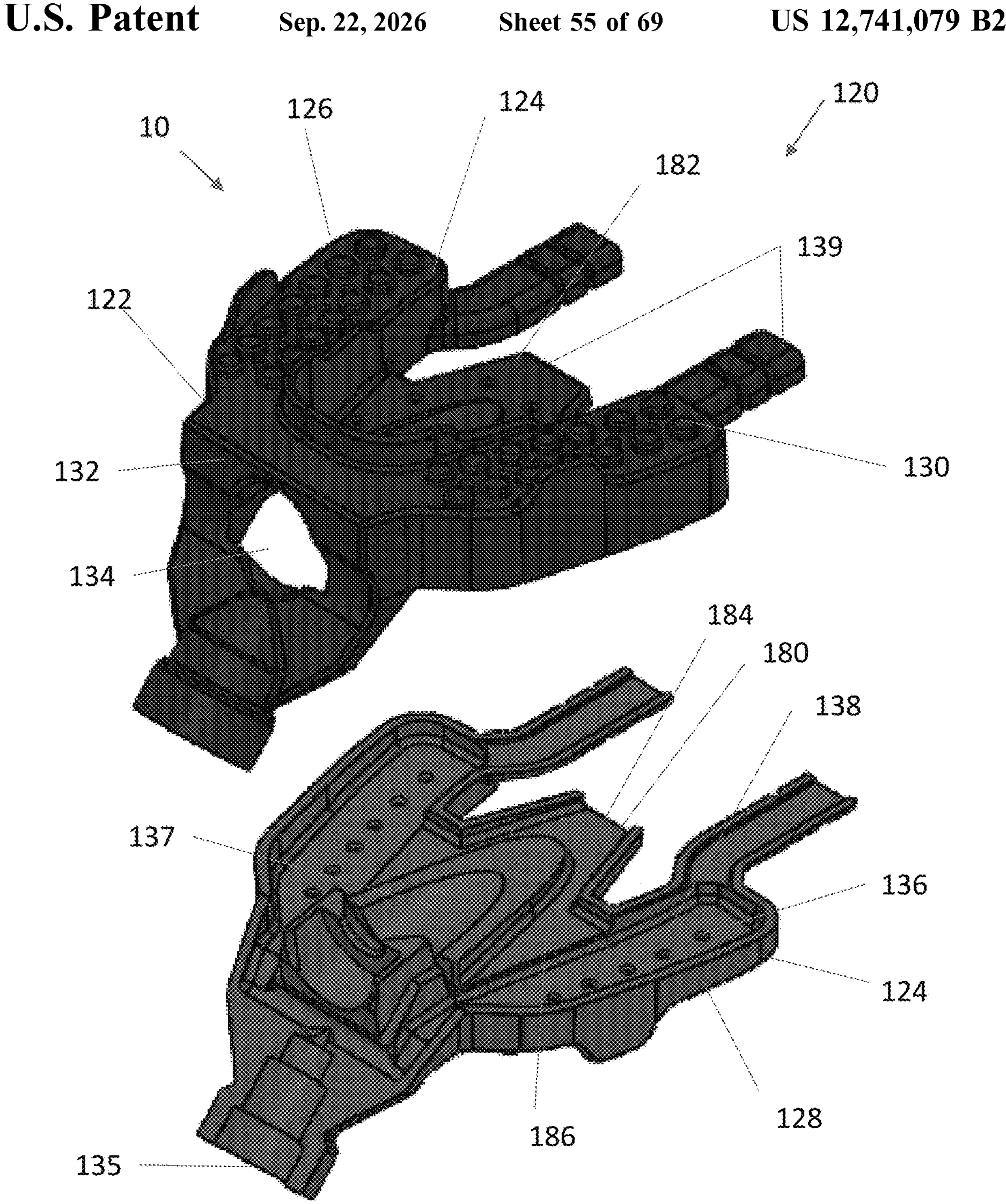
FIG. 55 is an exploded front perspective view of the oral phlegm extraction system of FIG. 50 with the portions of the misting apparatus removed.
Figure 56:
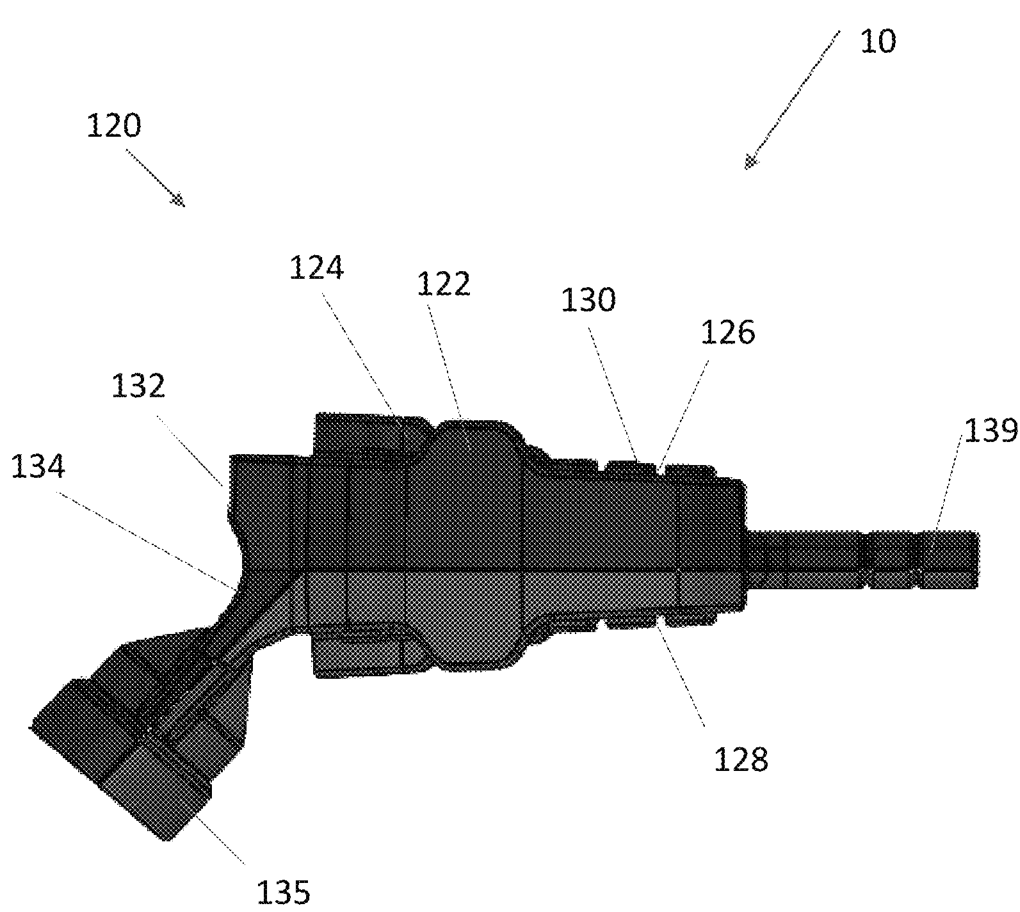
FIG. 56 is a side view of the oral phlegm extraction system of FIG. 50 with the portions of the misting apparatus removed.
Figure 57:
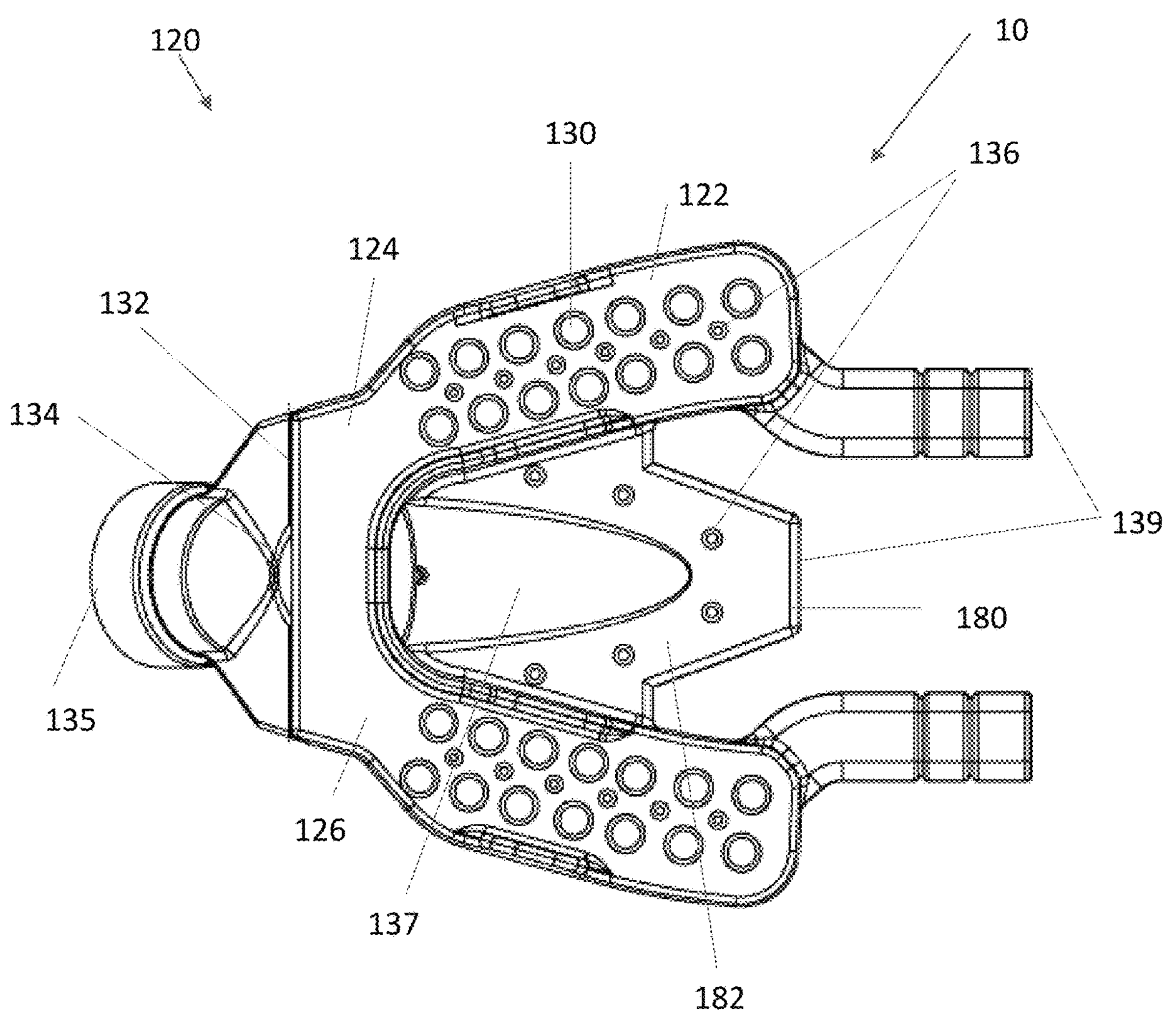
FIG. 57 is a top view of the oral phlegm extraction system of FIG. 50 with the portions of the misting apparatus removed.
Figure 58:
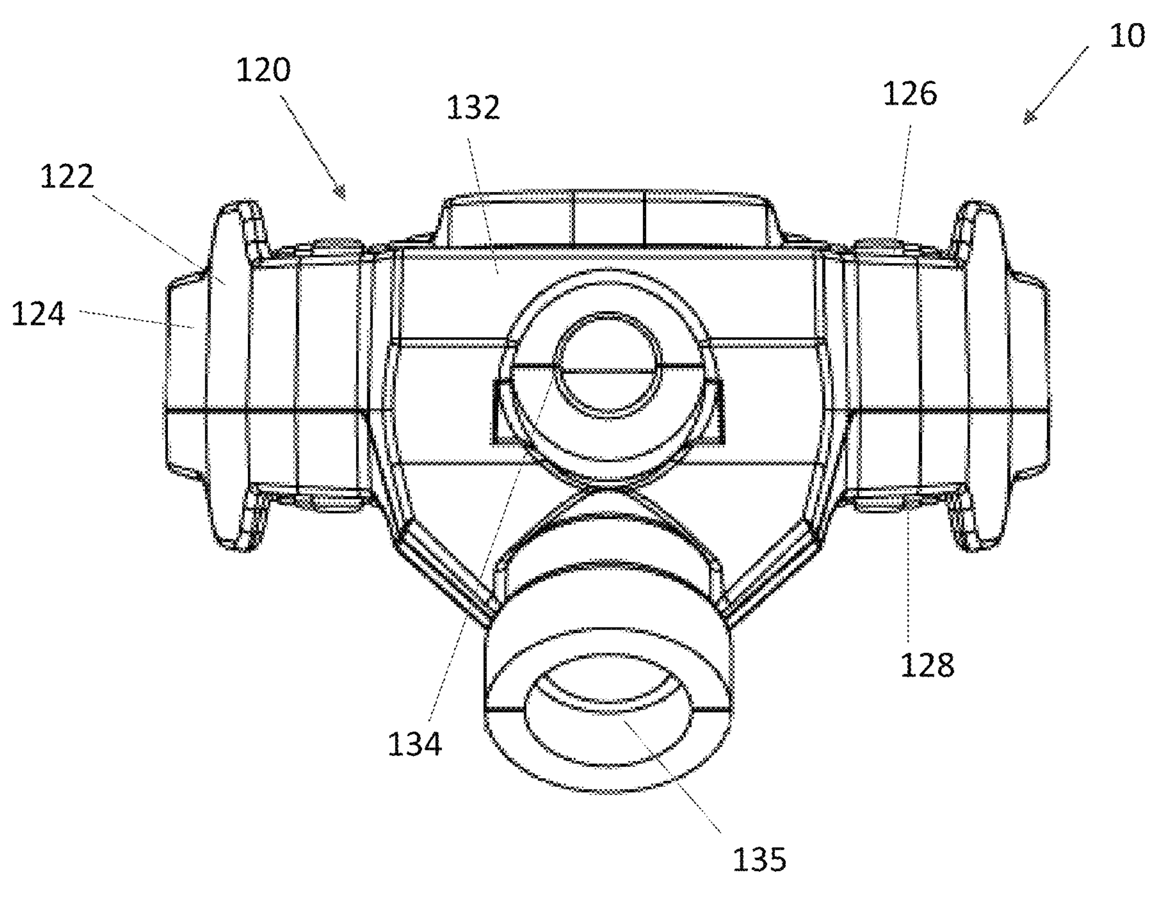
FIG. 58 is a front view of the oral phlegm extraction system of FIG. 50 with the portions of the misting apparatus removed.
Figure 59:
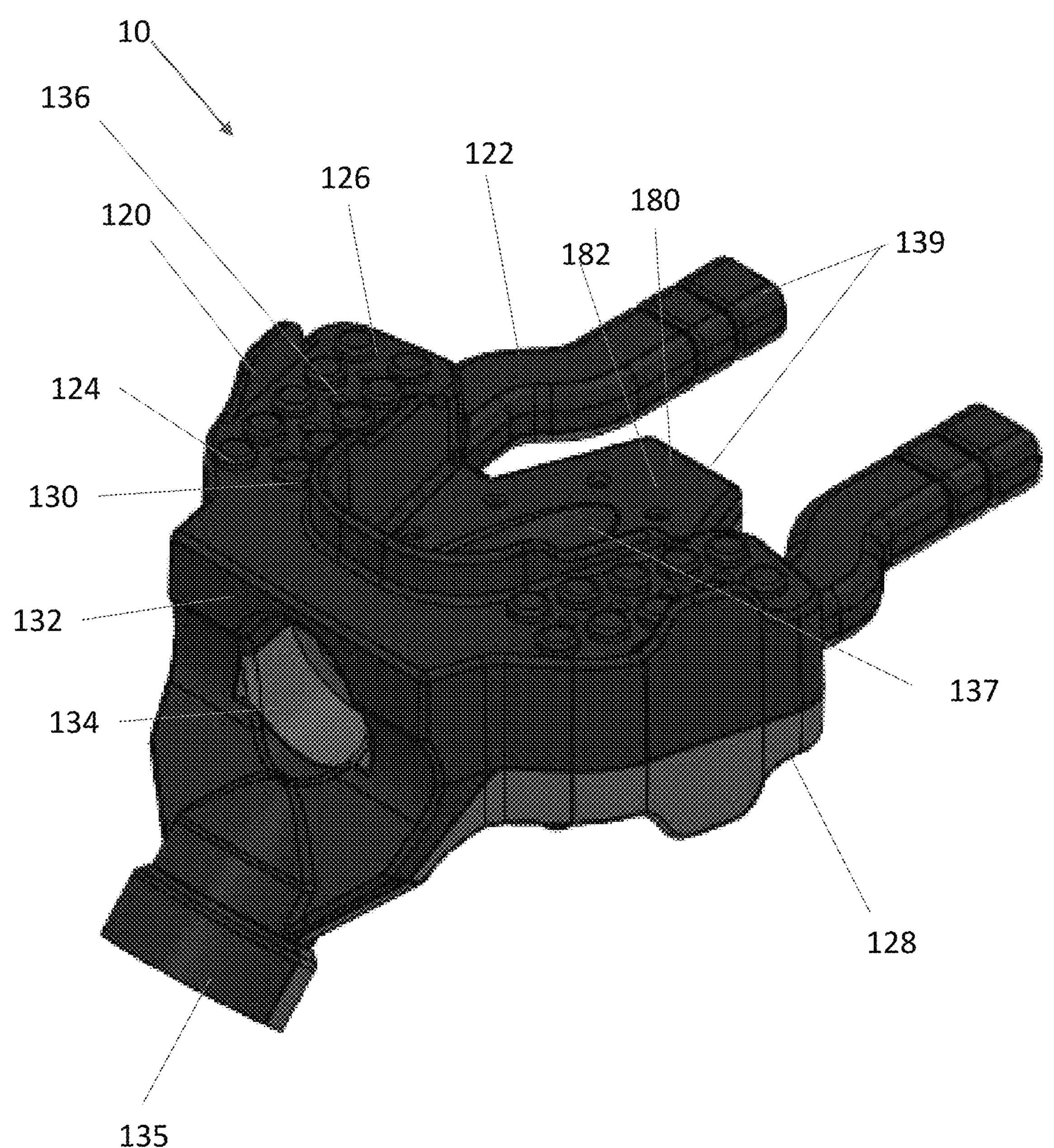
FIG. 59 is a front perspective view of an oral phlegm extraction system comprising a mouth insertion apparatus with a smaller base to accommodate patients with smaller mouths, according to certain embodiments of the present invention.
Figure 61:
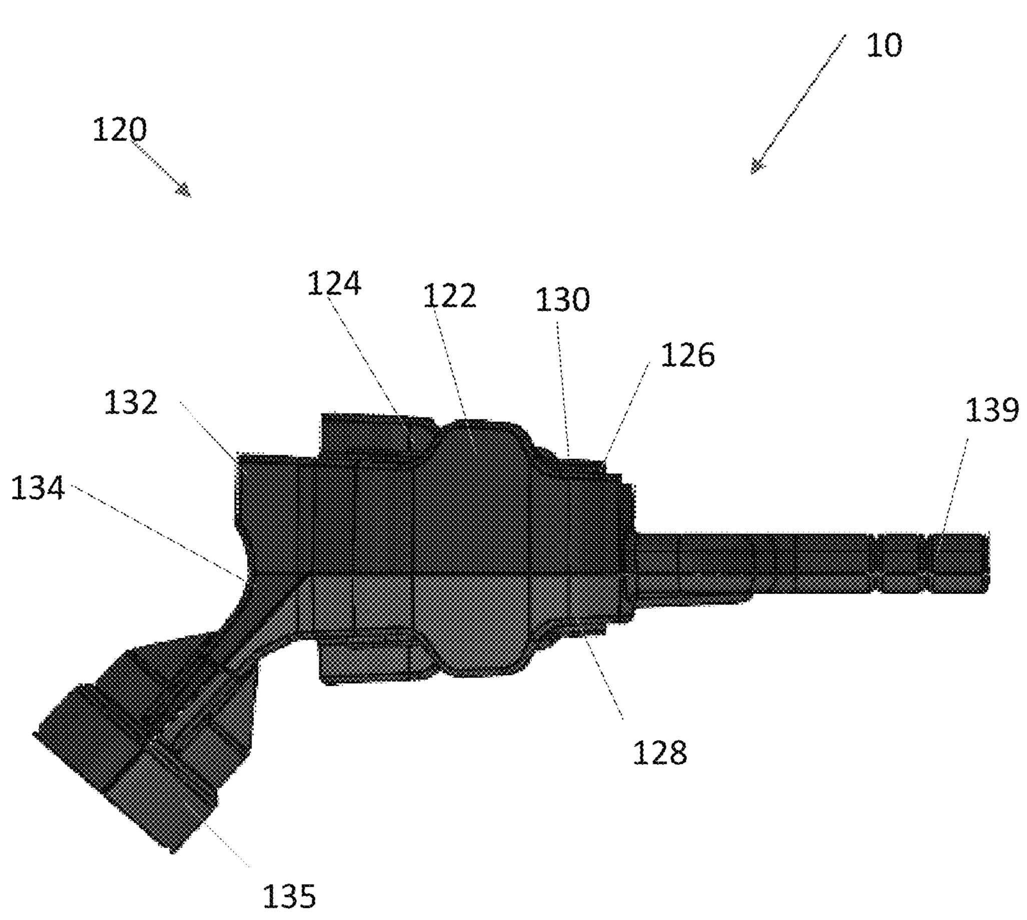
FIG. 61 is a side view of the oral phlegm extraction system of FIG. 59.
Figure 62:
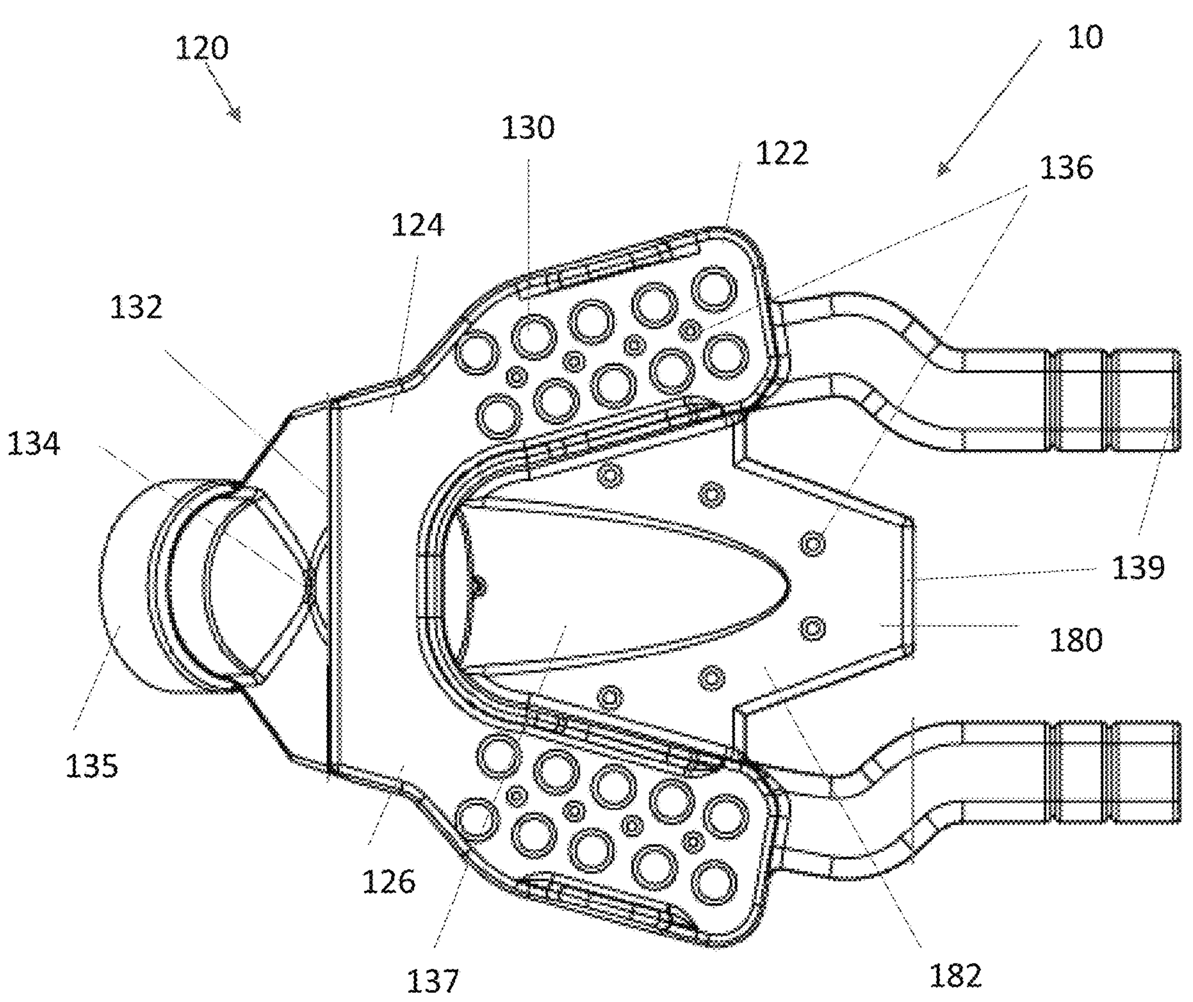
FIG. 62 is a top view of the oral phlegm extraction system of FIG. 59.
Figure 63:
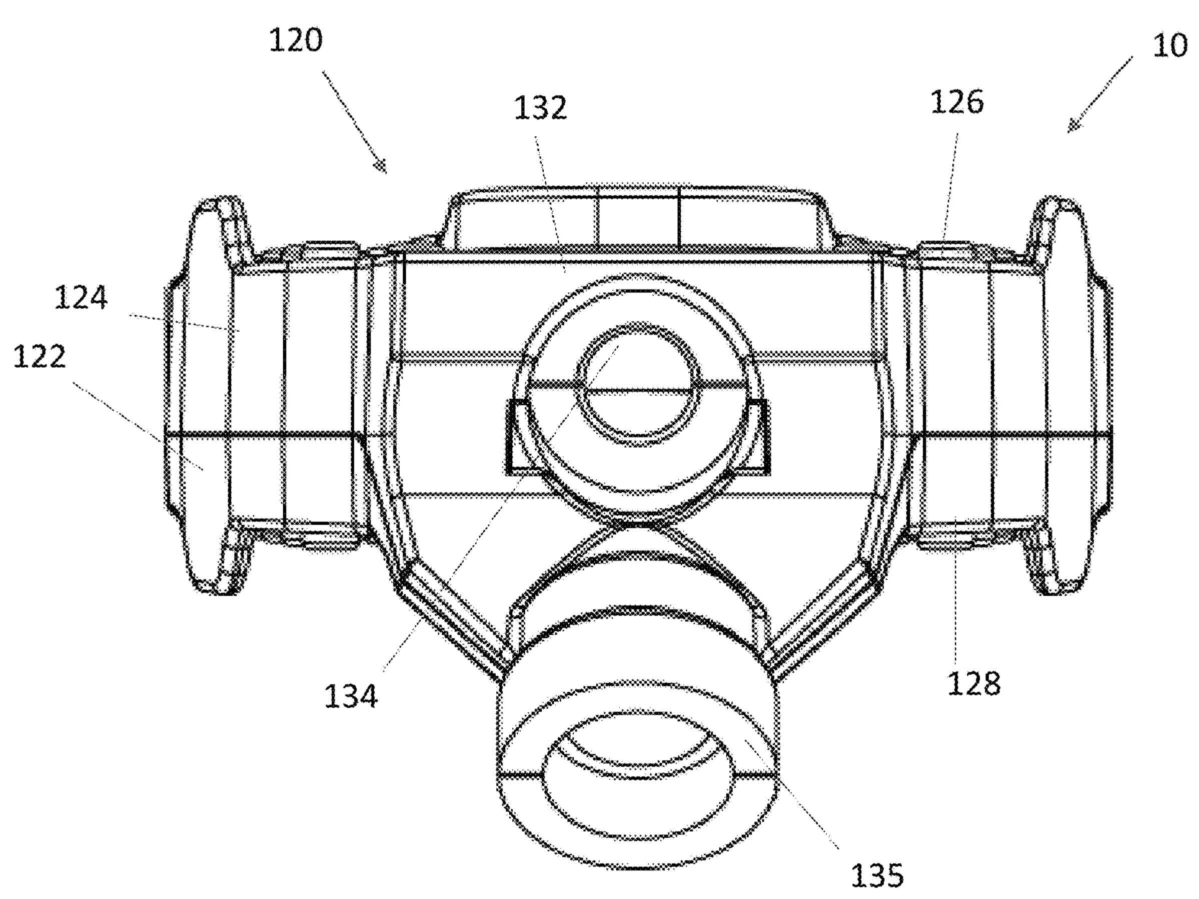
FIG. 63 is a front view of the oral phlegm extraction system of FIG. 59.
Figure 64:
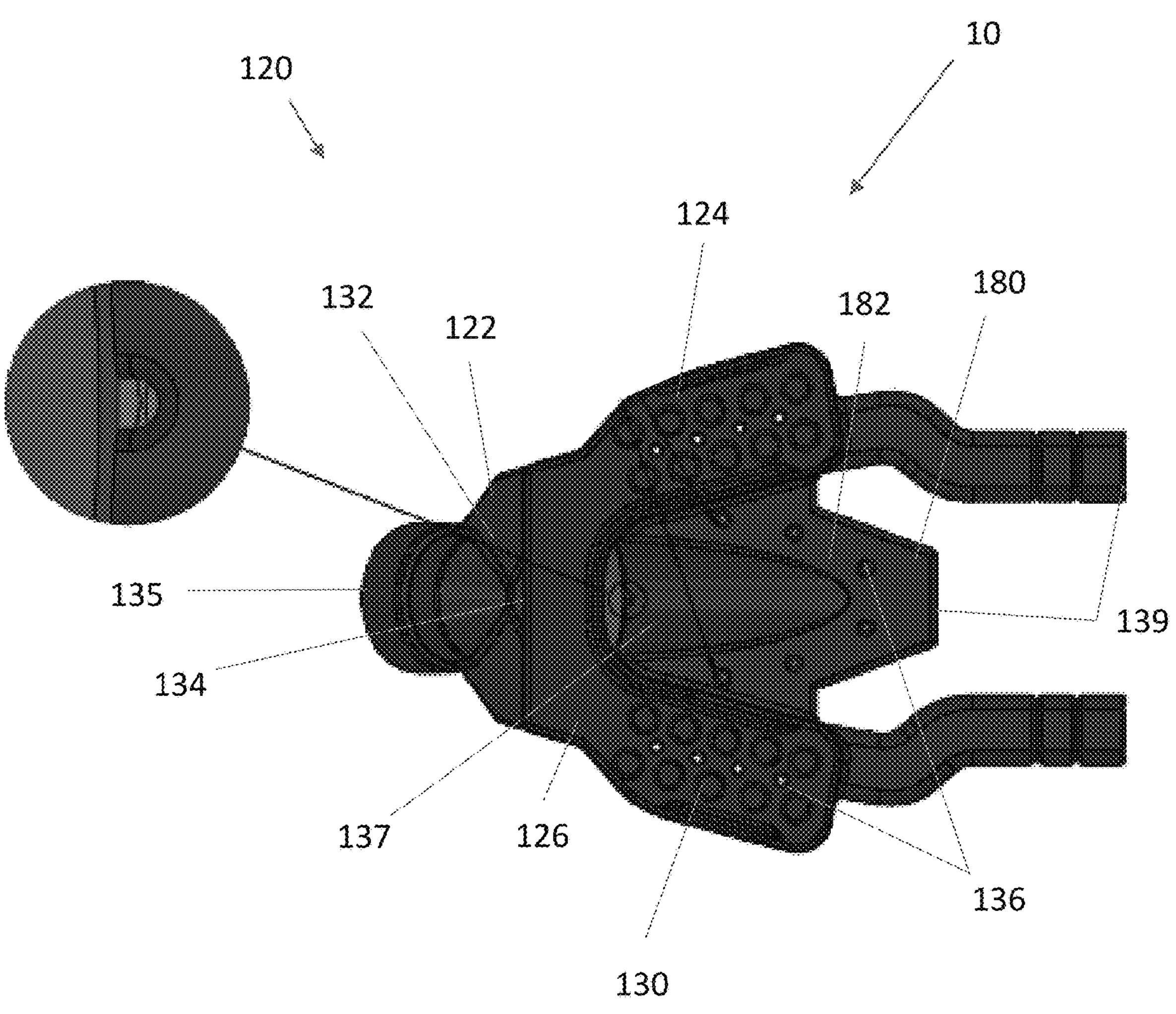
FIG. 64 is another top view of the oral phlegm extraction system of FIG. 59.
Figure 65:
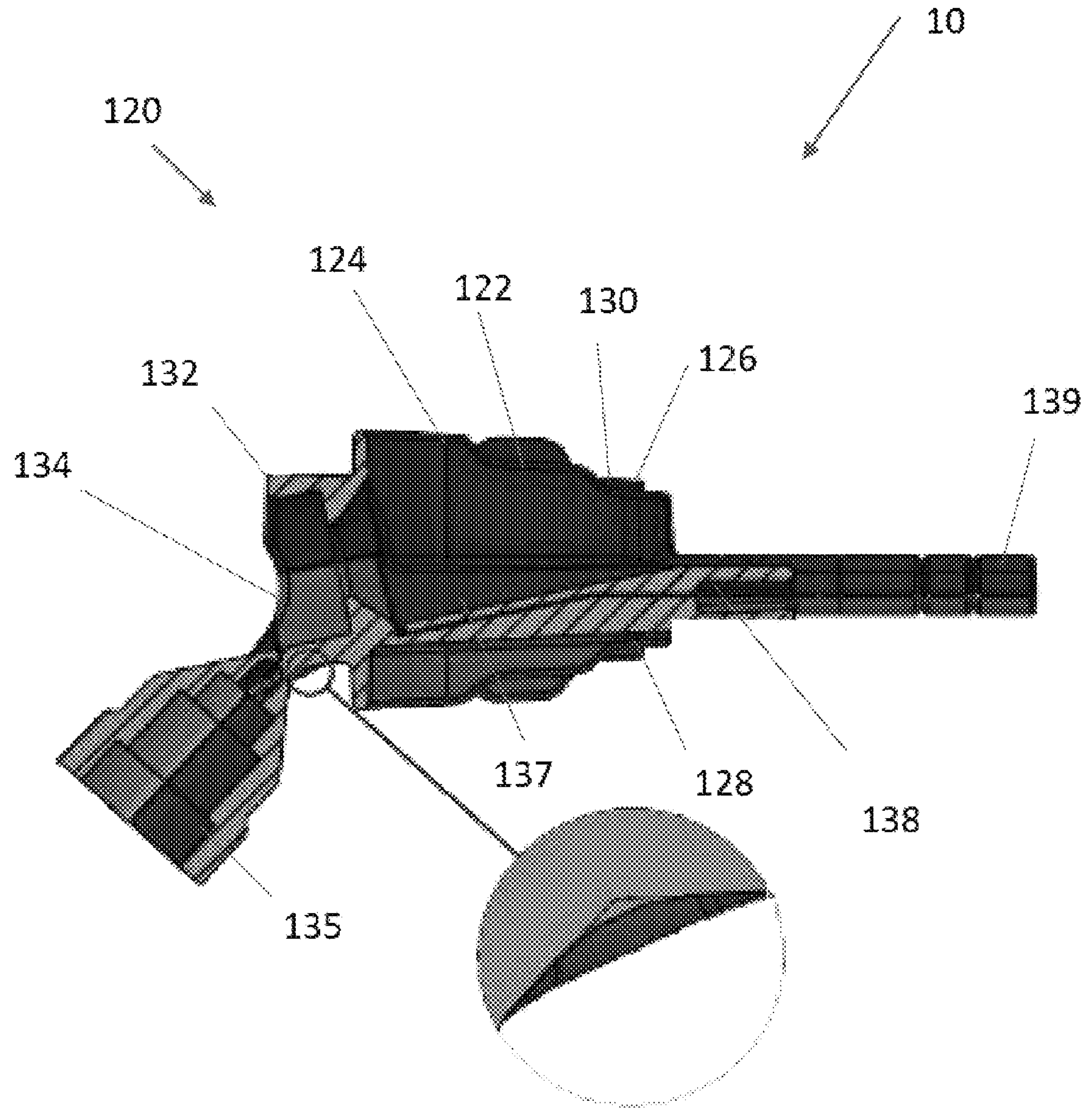
FIG. 65 is a side cross-sectional view of the oral phlegm extraction system of FIG. 59.

In some embodiments, as best illustrated in FIG. 16, a timer 153 may be coupled to the liquid pump 154 and/or the compressor 156 to control the frequency and duration of the liquid and gas flow into the nozzle 142. As an example, a timer 153 may comprise any timer that is capable of providing open/closed cycle intervals in the range of 5 seconds to 30 minutes.

III. Suction Apparatus

In some embodiments, as best illustrated in FIGS. 8, 11, and 14-15, the suction apparatus 160 may be joined to the outlet opening 135 via a hose 162 or other similar coupling item that allows the collected materials to be removed from the hollow interior regions 138, 186. The hose 162 in turn coupled to an inlet side 166 of a collection vessel 164. An outlet side 168 of the collection vessel 164 may be coupled to a vacuum pump 170, which creates a vacuum inside the collection vessel 164 to draw the collected material out of the hollow interior regions 138, 186.

IV. Upper-Body Postural Support and Alignment Apparatus

Figure 66:
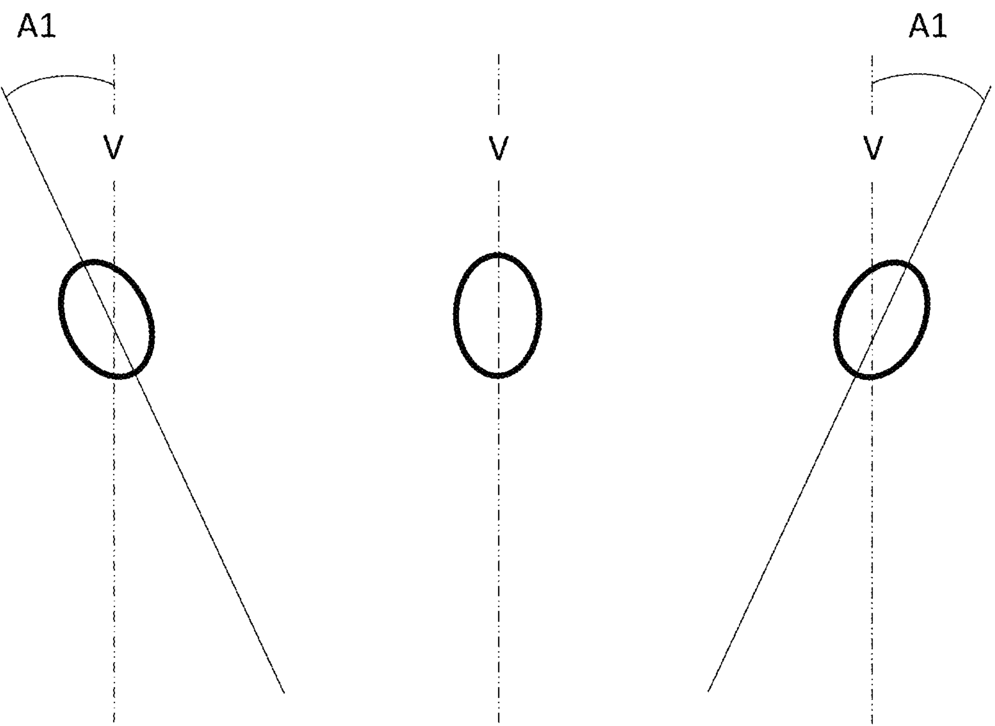
FIG. 66 is a side view of a sitting patient with the patient's head rotated backward, upright, and forward relative to a vertical axis V.
Figure 67:
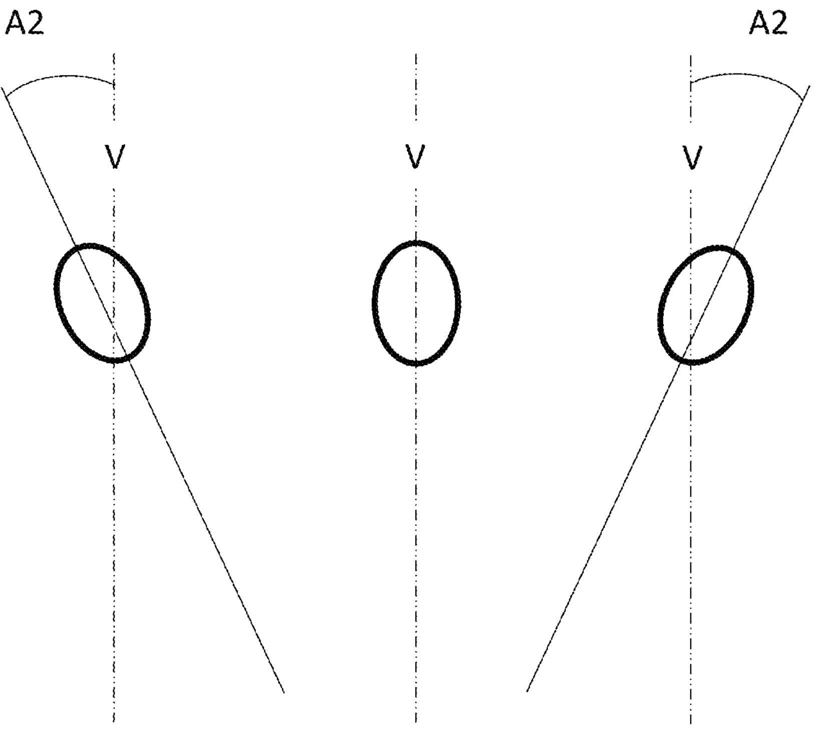
FIG. 67 is a front view of a sitting patient with the patient's head rotated to the right, upright, and left relative to a vertical axis V.
Figure 68:
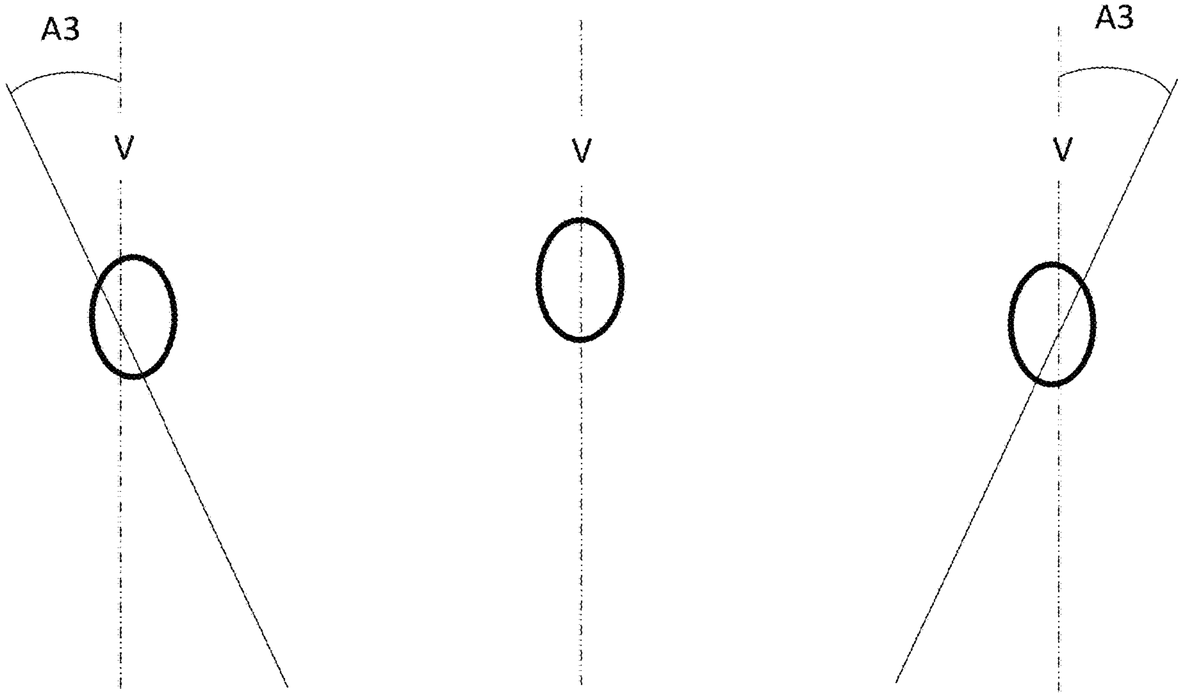
FIG. 68 is a side view of a sitting patient with the patient's upper torso rotated backward, upright, and forward relative to a vertical axis V.
Figure 69:
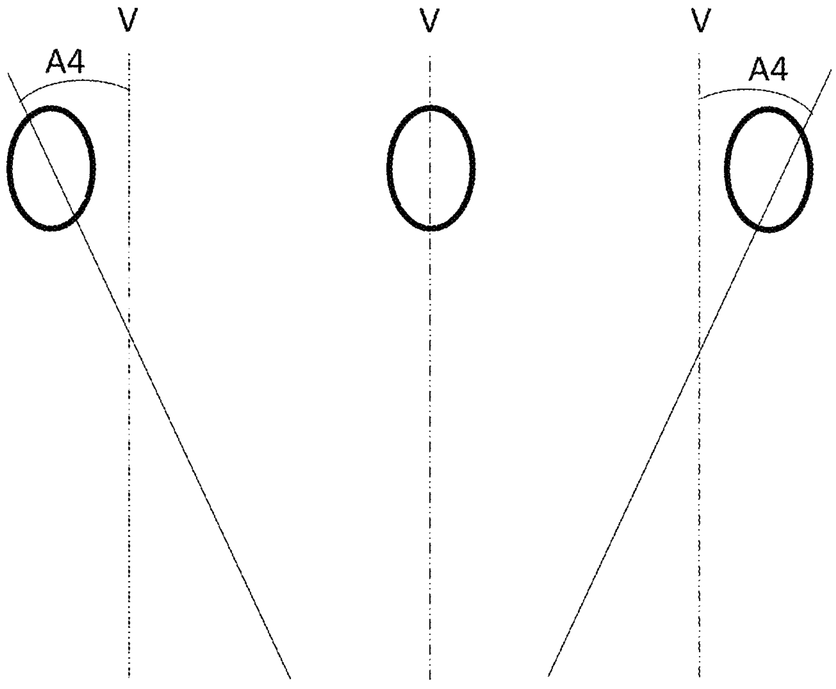
FIG. 69 is a front view of a sitting patient with the patient's upper torso rotated to the right, upright, and left relative to a vertical axis V.

In certain embodiments, it may be necessary to maintain a patient's head and/or upper torso in a desired position during the time that the patient is using the oral phlegm extraction system 10. In particular, the optimal position for a patient's head and/or upper torso may be defined based on four angles measured relative to a vertical axis V:

- forward/backward movement of a patient's head relative to a patient's upper torso, which forms an angle A1 with respect to the vertical axis V (FIG. 66);
- left/right movement of a patient's head relative to a patient's upper torso, which forms an angle A2 with respect to the vertical axis V (FIG. 67);
- forward/backward movement of a patient's upper torso relative a patient's lower torso, which forms an angle A3 with respect to the vertical axis V (FIG. 68); and
- left/right movement of a patient's upper torso relative to a patient's lower torso, which forms an angle A4 with respect to the vertical axis V (FIG. 69).

The range of angles for A1, A2, A3, and A4 may be between +25/−25 degrees relative to the vertical axis V, further may be between +25/−20 degrees relative to the vertical axis V, further may be between +25/−15 degrees relative to the vertical axis V, further may be between +25/−10 degrees relative to the vertical axis V, further may be between +25/−5 degrees relative to the vertical axis V, further may be between +25/0 degrees relative to the vertical axis V, further may be between +25/+5 degrees relative to the vertical axis V, further may be between +25/+10 degrees relative to the vertical axis V, further may be between +25/+15 degrees relative to the vertical axis V, further may be between +25/+20 degrees relative to the vertical axis V, further may be between +20/−25 degrees relative to the vertical axis V, further may be between +20/−20 degrees relative to the vertical axis V, further may be between +20/−15 degrees relative to the vertical axis V, further may be between +20/−10 degrees relative to the vertical axis V, further may be between +20/−5 degrees relative to the vertical axis V, further may be between +20/0 degrees relative to the vertical axis V, further may be between +20/+5 degrees relative to the vertical axis V, further may be between +20/+10 degrees relative to the vertical axis V, further may be between +20/+15 degrees relative to the vertical axis V, further may be between +15/−25 degrees relative to the vertical axis V, further may be between +15/−20 degrees relative to the vertical axis V, further may be between +15/−15 degrees relative to the vertical axis V, further may be between +15/−10 degrees relative to the vertical axis V, further may be between +15/−5 degrees relative to the vertical axis V, further may be between +15/0 degrees relative to the vertical axis V, further may be between +15/+5 degrees relative to the vertical axis V, further may be between +15/+10 degrees relative to the vertical axis V, further may be between +10/−25 degrees relative to the vertical axis V, further may be between +10/−20 degrees relative to the vertical axis V, further may be between +10/−15 degrees relative to the vertical axis V, further may be between +10/−10 degrees relative to the vertical axis V, further may be between +10/−5 degrees relative to the vertical axis V, further may be between +10/0 degrees relative to the vertical axis V, further may be between +10/+5 degrees relative to the vertical axis V, further may be between +5/−25 degrees relative to the vertical axis V, further may be between +5/−20 degrees relative to the vertical axis V, further may be between +5/−15 degrees relative to the vertical axis V, further may be between +5/−10 degrees relative to the vertical axis V, further may be between +5/−5 degrees relative to the vertical axis V, further may be between +5/0 degrees relative to the vertical axis V, further may be between +0/−25 degrees relative to the vertical axis V, further may be between +0/−20 degrees relative to the vertical axis V, further may be between +0/−15 degrees relative to the vertical axis V, further may be between +0/−10 degrees relative to the vertical axis V, and further may be between +0/−5 degrees relative to the vertical axis V. The ranges for each of A1, A2, A3, and A4 may be the same or different from one another, depending on a patient's particular physiology and surgical recovery needs. A person of ordinary skill in the relevant art will understand that any suitable range may be used for the A1, A2, A3, and A4 that results in the mouth insertion apparatus 120 being positioned within a patient's mouth at an angle relative to a vertical axis within a range of +/−20 degrees to +/−25 degrees. Maintaining the position of the mouth insertion apparatus 120 within these ranges provides the optimal recovery results and minimizes the risk of unwanted results for a particular patient.

For example, if the patient's head is reclined too far back, there is a risk of aspiration of the phlegm, mucus, blood, or other fluids into the patient's lungs. Conversely, if the patient's head is positioned too far upright, the moist gas may not reach the intended locations within the patient's mouth and throat. Thus, when a patient is sleeping in a reclining chair or in a seat that is able to maintain a patient's body within the desired ranges for A1, A2, A3, and/or A4, the patient can achieve optimal recovery results while also being able to rest without experiencing undue unwanted results.

In some embodiments, as best illustrated in FIGS. 17-20, a positioning apparatus 179 for a patient's head and upper body may be utilized to avoid these undesirable outcomes. The positioning apparatus 179 is designed to attach to most living room seats and recliners, as illustrated in FIGS. 17-20.

The positioning apparatus 179 may include a head rest 181, a head strap 183, upper torso straps 185, and leg supports 187. The positioning apparatus 179 positions the patient's head, chest, and shoulders in place and prevents the patient from leaning/slouching while sleeping. The head strap 183 prevents the patient's head from dropping forward.

Some or all of these items may comprise a gel or other similar cushioning, which minimizes the chance that the patient will develop bed sores from sitting in the chair for multiple weeks during recovery.

V. Carrying Case

As best illustrated in FIGS. 14-16, the misting apparatus 140 and the suction apparatus 160 components may be housed within a portable carrying case 190. The controls that need to be accessed by the patient/caregiver may be positioned on an outer surface of the carrying case 190. Likewise, the liquid reservoir 152 and/or the collection vessel 164 may be positioned outside of the carrying case 190 to allow the contents of the containers to be emptied/replaced without the need for the patient/caregiver to open the carrying case 190. Moreover, in some embodiments, a vinyl cover may be positioned over the foam 192 inside the carrying case 190 to prevent infection control and allow easy cleaning in the event the components within the carrying case 190 are re-used for future patients.

In the following, further examples are described to facilitate the understanding of the invention:

Example A. An oral phlegm extraction system comprising:
- a mouth insertion apparatus comprising:
  - a platform shaped to engage with a patient's teeth when worn and comprising at least one suction aperture positioned on a proximal end of the platform and directed toward an entrance to the patient's throat;
  - a tongue positioner joined to the platform, wherein the tongue positioner comprises:
    - at least one suction aperture positioned on a proximal end of the tongue positioner and directed toward an entrance to the patient's throat; and
    - a region shaped to direct a flow of moist gas toward the entrance to the patient's throat;
  - a hollow interior region in open communication with the at least one platform suction aperture and the at least one tongue positioner suction aperture;
- a misting apparatus comprising:
  - a nozzle coupled to a distal end of the platform that is programmable to control at least one of frequency, duration, or content of a moist gas stream that is introduced into the patient's mouth and throat;
  - wherein the nozzle is positioned so that the moist gas stream flows out of the nozzle and is directed toward the shaped region of the tongue positioner; and
- a suction apparatus comprising:
  - a vacuum pump coupled to the distal end of the platform and in open communication with the hollow interior region of the platform and tongue positioner to remove collected substances from the patient's mouth and throat.

Example B. The oral phlegm extraction system of any of the preceding or subsequent examples, further comprising a plurality of nubs positioned on at least one of an upper surface or a lower surface of the platform.

Example C. The oral phlegm extraction system of any of the preceding or subsequent examples, further comprising a plurality of suction apertures positioned on at least one of an upper surface or a lower surface of the platform.

Example D. The oral phlegm extraction system of any of the preceding or subsequent examples, further comprising a plurality of suction apertures positioned on at least one of an upper surface or a lower surface of the tongue positioner.

Example E. The oral phlegm extraction system of any of the preceding or subsequent examples, wherein the at least one suction aperture positioned on the proximal end of the platform and the at least one suction aperture positioned on the proximal end of the tongue positioner are larger than the plurality of suction apertures positioned on the at least one upper surface or lower surface of the platform and the plurality of suction apertures positioned on the at least one upper surface or lower surface of the tongue positioner.

Example F. The oral phlegm extraction system of any of the preceding or subsequent examples, wherein a patient's tongue is positionable above or below the tongue positioner.

Example G. The oral phlegm extraction system of any of the preceding or subsequent examples, further comprising a head positioning apparatus that utilizes at least one strap to immobilize the patient's head in a position that balances collection of the substances from the patient's mouth and throat with application of the moist gas to desired locations in the patient's mouth and throat.

Example H. The oral phlegm extraction system of any of the preceding or subsequent examples, further comprising upper torso straps and leg supports.

Example I. The oral phlegm extraction system of any of the preceding or subsequent examples, wherein the mouth insertion apparatus is positioned within the patient's mouth at an angle relative to a vertical axis within a range of +25 to −25 degrees.

Example J. An oral phlegm extraction system comprising:
- a mouth insertion apparatus comprising:
  - a platform shaped to engage with a patient's teeth when worn and comprising at least one suction aperture positioned on a proximal end of the platform and directed toward an entrance to the patient's throat;
  - a tongue positioner joined to the platform, wherein the tongue positioner comprises a region shaped to direct a flow of moist gas toward the entrance to the patient's throat;
  - a hollow interior region in open communication with the at least one platform suction aperture;
- a misting apparatus comprising:
  - a nozzle coupled to a distal end of the platform that is programmable to control at least one of frequency, duration, or content of a moist gas stream that is introduced into the patient's mouth and throat;
  - wherein the nozzle is positioned so that the moist gas stream flows out of the nozzle and is directed toward the shaped region of the tongue positioner; and a suction apparatus comprising:

a vacuum pump coupled to the distal end of the platform and in open communication with the hollow interior region of the platform to remove collected substances from the patient's mouth and throat; and a head positioning apparatus that utilizes at least one strap to immobilize the patient's head in a position that balances collection of the substances from the patient's mouth and throat with application of the moist gas to desired locations in the patient's mouth and throat.

Example K. The oral phlegm extraction system of any of the preceding or subsequent examples, further comprising a plurality of nubs positioned on at least one of an upper surface or a lower surface of the platform.

Example L. The oral phlegm extraction system of any of the preceding or subsequent examples, further comprising a plurality of suction apertures positioned on at least one of an upper surface or a lower surface of the platform.

Example M. The oral phlegm extraction system of any of the preceding or subsequent examples, further comprising a plurality of suction apertures positioned on at least one of an upper surface or a lower surface of the tongue positioner.

Example N. The oral phlegm extraction system of any of the preceding or subsequent examples, wherein the at least one suction aperture positioned on the proximal end of the platform and the at least one suction aperture positioned on the proximal end of the tongue positioner are larger than the plurality of suction apertures positioned on the at least one upper surface or lower surface of the platform and the plurality of suction apertures positioned on the at least one upper surface or lower surface of the tongue positioner.

Example O. The oral phlegm extraction system of any of the preceding or subsequent examples, wherein the mouth insertion apparatus is positioned within the patient's mouth at an angle relative to a vertical axis within a range of +25 to −25 degrees.

Example P. A method of using an oral phlegm extraction system, the oral phlegm extraction system comprising a mouth insertion apparatus, a misting apparatus comprising a nozzle with a timer, a liquid supply system, and a gas supply system, and a suction apparatus, the method comprising:

selecting a frequency for the timer to open the nozzle;

selecting a duration for the timer to keep the nozzle open;

selecting a flowrate of liquid to be provided to the nozzle via the liquid supply system when the nozzle is open;

selecting a flowrate of moist gas to be provided to the nozzle via the gas supply system when the nozzle is open;

positioning the mouth insertion apparatus into a patient's mouth;

actuating the misting apparatus to begin operation; and actuating the suction apparatus to begin operation.

Example Q. The method of any of the preceding or subsequent examples, further comprising attaching at least one strap to the patient's head to immobilize the patient's head at a desired angle.

Example R. The method of any of the preceding or subsequent examples, wherein the desired angle of the patient's head is one that balances collection of substances from the patient's mouth and throat with application of the moist gas to desired locations in the patient's mouth and throat.

Example S. The method of any of the preceding or subsequent examples, further comprising attaching at least one strap to the patient's upper torso to immobilize the patient's upper torso posture.

Example T. The method of any of the preceding or subsequent examples, further comprising placing the patient's legs onto leg supports.

Example U. The method of any of the preceding or subsequent examples, wherein the head and body positioning devices are combined into a unitary apparatus.

Example V. The method of any of the preceding or subsequent examples, wherein the step of positioning the mouth insertion apparatus into a patient's mouth is performed by positioning the mouth insertion apparatus into a patient's mouth at an angle relative to a vertical axis within a range of +25 to −25 degrees.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. An oral phlegm extraction system comprising:

a mouth insertion apparatus comprising:

a platform shaped to engage with a patient's teeth when worn and comprising at least one platform suction aperture positioned on a proximal end of the platform and directed toward an entrance to a patient's throat;

a tongue positioner joined to the platform, wherein the tongue positioner comprises:

at least one tongue positioner suction aperture positioned on a proximal end of the tongue positioner and directed toward the entrance to the patient's throat; and a region shaped to direct a moist gas stream toward the entrance to the patient's throat;

a hollow interior region in open communication with the at least one platform suction aperture and the at least one tongue positioner suction aperture;

a misting apparatus comprising:

a nozzle coupled to a distal end of the platform that is programmable to control at least one of frequency, duration, or content of the moist gas stream that is introduced into the patient's throat and a patient's mouth;

wherein the nozzle is positioned so that the moist gas stream flows out of the nozzle and is directed toward the shaped region of the tongue positioner; and a suction apparatus comprising:

a vacuum pump coupled to the distal end of the platform and in open communication with the hollow interior region to remove substances collected from the patient's throat and the patient's mouth.

2. The oral phlegm extraction system of claim 1, wherein the platform further comprises an upper platform surface and a lower platform surface, and a plurality of nubs positioned on at least one of the upper platform surface or the lower platform surface.

3. The oral phlegm extraction system of claim 2, wherein the platform further comprises a first plurality of suction apertures positioned on at least one of the upper platform surface or the lower platform surface.

4. The oral phlegm extraction system of claim 3, wherein the tongue positioner further comprises an upper tongue positioner surface and a lower tongue positioner surface, and a second plurality of suction apertures positioned on at least one of the upper tongue positioner surface or the lower tongue positioner surface.

5. The oral phlegm extraction system of claim 4, wherein the at least one platform suction aperture and the at least one tongue positioner suction aperture are larger than the first plurality of suction apertures and the second plurality of suction apertures.

6. The oral phlegm extraction system of claim 1, wherein a patient's tongue is positionable above or below the tongue positioner.

7. The oral phlegm extraction system of claim 1, further comprising a head positioning apparatus that utilizes at least one strap to immobilize a patient's head in a position that balances collection of the substances from the patient's throat and the patient's mouth with application of the moist gas stream to desired locations in the patient's throat and the patient's mouth.

8. The oral phlegm extraction system of claim 7, further comprising upper torso straps and leg supports.

9. The oral phlegm extraction system of claim 8, wherein the mouth insertion apparatus is positioned within the patient's mouth at an angle relative to a vertical axis within a range of +25 to −25 degrees.

10. An oral phlegm extraction system comprising:

a mouth insertion apparatus comprising:

a platform shaped to engage with a patient's teeth when worn and comprising at least one platform suction aperture positioned on a proximal end of the platform and directed toward an entrance to a patient's throat;

a tongue positioner joined to the platform, wherein the tongue positioner comprises a region shaped to direct a moist gas stream toward the entrance to the patient's throat;

a hollow interior region in open communication with the at least one platform suction aperture;

a misting apparatus comprising:

a nozzle coupled to a distal end of the platform that is programmable to control at least one of frequency, duration, or content of the moist gas stream that is introduced into the patient's throat and a patient's mouth;

wherein the nozzle is positioned so that the moist gas stream flows out of the nozzle and is directed toward the shaped region of the tongue positioner; and a suction apparatus comprising:

a vacuum pump coupled to the distal end of the platform and in open communication with the hollow interior region to remove substances collected from the patient's throat and the patient's mouth; and a head positioning apparatus that utilizes at least one strap to immobilize a patient's head in a position that balances collection of the substances from the patient's throat and the patient's mouth with application of the moist gas stream to desired locations in the patient's throat and the patient's mouth.

11. The oral phlegm extraction system of claim 10, wherein the platform further comprises an upper platform surface and a lower platform surface, and a plurality of nubs positioned on at least one of the upper platform surface or the lower platform surface.

12. The oral phlegm extraction system of claim 11, wherein the platform further comprises a first plurality of suction apertures positioned on at least one of the upper platform surface or the lower platform surface.

13. The oral phlegm extraction system of claim 12, wherein the tongue positioner further comprises an upper tongue positioner surface and a lower tongue positioner surface, and a second plurality of suction apertures positioned on at least one of the upper tongue positioner surface or the lower tongue positioner surface.

14. The oral phlegm extraction system of claim 13, wherein the at least one platform suction aperture is larger than the first plurality of suction apertures and the second plurality of suction apertures.

15. The oral phlegm extraction system of claim 10, wherein the mouth insertion apparatus is positioned within the patient's mouth at an angle relative to a vertical axis within a range of +25 to −25 degrees.

* * * * *